(12) United States Patent
Shankar et al.

(10) Patent No.: US 12,131,399 B2
(45) Date of Patent: Oct. 29, 2024

(54) SYSTEM AND METHOD FOR AUTOMATED REAGENT VERIFICATION

(71) Applicant: LIFE TECHNOLOGIES CORPORATION, Carlsbad, CA (US)

(72) Inventors: Shanti Shankar, Cheshire, CT (US); Sean Zimmerman, Encinitas, CA (US); Mark Beauchemin, Glastonbury, CT (US); John Thompson, Trumbull, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 1312 days.

(21) Appl. No.: 16/543,475

(22) Filed: Aug. 16, 2019

(65) Prior Publication Data

US 2020/0075130 A1 Mar. 5, 2020

Related U.S. Application Data

(60) Provisional application No. 62/855,643, filed on May 31, 2019, provisional application No. 62/719,085, filed on Aug. 16, 2018.

(51) Int. Cl.
*G16B 45/00* (2019.01)
*G01N 1/28* (2006.01)
*G06T 1/00* (2006.01)
*G16B 30/10* (2019.01)
*G01N 35/00* (2006.01)

(52) U.S. Cl.
CPC .. *G06T 1/0014* (2013.01); *G01N 2035/00801* (2013.01)

(58) Field of Classification Search
CPC .................................................. G01T 1/0014
See application file for complete search history.

(56) References Cited

U.S. PATENT DOCUMENTS

| | | | |
|---|---|---|---|
| 2002/0097396 A1* | 7/2002 | Schafer | B07C 5/10 356/240.1 |
| 2006/0173575 A1* | 8/2006 | Lefebvre | G01N 1/312 700/231 |
| 2008/0072664 A1* | 3/2008 | Hansen | G01N 1/38 422/63 |
| 2010/0291619 A1 | 11/2010 | Robinson et al. | |
| 2011/0143947 A1 | 6/2011 | Chamberlin et al. | |
| 2013/0065797 A1* | 3/2013 | Silbert | G01N 35/1016 73/304 C |

(Continued)

FOREIGN PATENT DOCUMENTS

| | | |
|---|---|---|
| EP | 2913042 | 9/2015 |
| WO | WO-2019094524 | 5/2019 |

OTHER PUBLICATIONS

Biomek NX and NXP Laboratory Automation Stations; Version 3.3 Tutorial; Beckman Coulter PNA40145, Revision AB, Mar. 2010.*

(Continued)

*Primary Examiner* — P. Kathryn Wright

(57) ABSTRACT

A method for user guided initiating of an instrument includes receiving a run plan via a user interface of the instrument; indicating on the user interface, based on the run plan, a consumable to be provided to the instrument; detecting the presence of the consumable using a vision system; and indicating the presence of the consumable via the user interface.

13 Claims, 52 Drawing Sheets

(56) References Cited

U.S. PATENT DOCUMENTS

| | | | |
|---|---|---|---|
| 2013/0288873 A1* | 10/2013 | Barbee | B04B 13/00 494/9 |
| 2013/0310726 A1 | 11/2013 | Miller et al. | |
| 2015/0051860 A1* | 2/2015 | Zuo | G01N 21/956 702/82 |
| 2015/0111236 A1* | 4/2015 | Dickopf | G06V 20/693 436/95 |
| 2015/0182966 A1* | 7/2015 | Coursey | G01N 21/6428 435/286.1 |
| 2015/0226759 A1* | 8/2015 | Connolly | G01N 35/00732 901/41 |
| 2015/0335531 A1* | 11/2015 | Yuyama | A61J 1/2096 141/18 |
| 2016/0238627 A1* | 8/2016 | Raicu | G01N 35/026 |
| 2016/0319329 A1* | 11/2016 | Natale | B01L 3/545 |
| 2018/0074082 A1* | 3/2018 | Glezer | G01N 35/00029 |
| 2018/0161244 A1 | 6/2018 | Lopez et al. | |
| 2018/0372766 A1* | 12/2018 | Bryant | B01L 3/52 |
| 2019/0361041 A1* | 11/2019 | Sasaki | B01L 9/543 |
| 2020/0319219 A1* | 10/2020 | Vansickler | G01N 35/04 |

OTHER PUBLICATIONS

PCT/US2019/046960, Search Report and Written Opinion, Jan. 13, 2020.

* cited by examiner

SYSTEM AND METHOD FOR AUTOMATED REAGENT VERIFICATION

CROSS-REFERENCE TO RELATED APPLICATION(S)

This application claims benefit of U.S. Provisional Application No. 62/719,085, filed Aug. 16, 2018, which is incorporated herein by reference in its entirety.

This application claims benefit of U.S. Provisional Application No. 62/855,643, filed May 31, 2019, which is incorporated herein by reference in its entirety.

FIELD OF THE DISCLOSURE

This disclosure, in general, relates to automated monitoring of preparation tasks and verification of appropriate reagents for a nucleic acid sequencing instrument to generate a sequencing run.

BACKGROUND

As medical science advances, new tests are developed to ascertain the root cause of disease, efficacies in medicines, and advanced immunology. In particular, tests involving genetic sequencing are providing more sophisticated answers to such questions. However, such tests tend to be complex and costly.

In contrast, there is increasing pressure to decrease the cost of medicine despite the demand for sophisticated costly testing. As such, there is an increased drive to provide integrated and automated instruments into clinical settings. However, the more complex the test, the more reagents and other consumables are supplied for testing within an instrument, increasing the chances of human error and costs associated with invalid tests.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an embodiment, a vision system is used within an instrument, such as a sequencing instrument, to assist the user in preparing the instrument to run a test. The vision system can assist the user in detecting the proper positioning and provisioning of consumables, such as reagent strips, pipette tips, microwell arrays, or other consumables associated with testing. In particular, the vision system can check to see that consumables are locked in place and identified as the correct consumable associated with a run plan of the test. Further, the vision system can detect used reagent containers and direct the user in removing such used containers as appropriate for a given run plan. The system can also include other consumable detection systems, such as a radio frequency identification (RFID) detection system. Such systems find particular use in integrated sequencing equipment.

Figure 1:
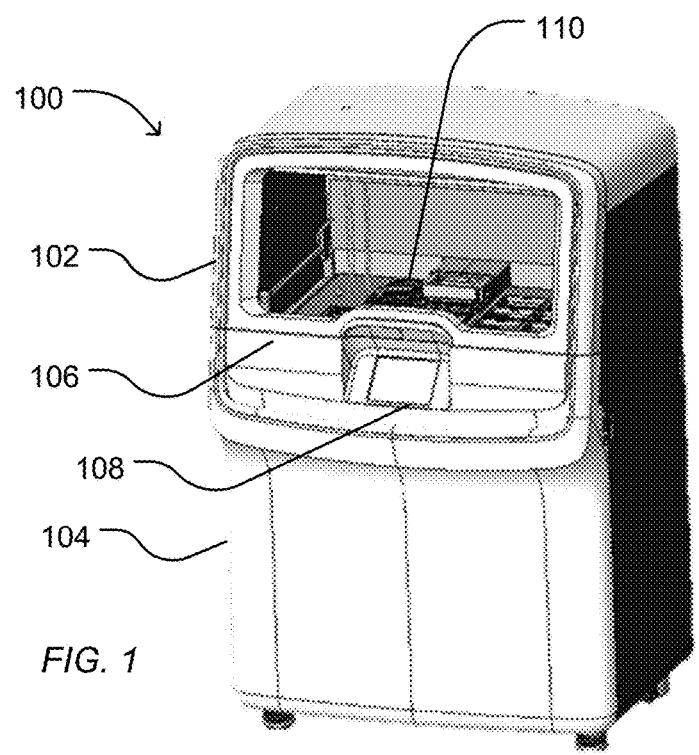
FIG. 1 includes an illustration of an example instrument.

FIG. 1 includes an illustration of an example instrument 100 incorporating a three-axis pipetting robot. In an example, the instrument 100 can be a sequencer incorporating a sample prep preparation platform. For example, the instrument 100 can include an upper portion 102 and a lower portion 104. The upper portion can include a door 106 to access a deck 110 on which samples, reagent containers, and other consumables are placed. The lower portion can include a cabinet for storing additional reagent solutions and other parts of the instrument 100. In addition, the instrument can include a user interface, such as a touchscreen display 108.

In a particular example, the instrument 100 can be a sequencing instrument. In some embodiments, the sequencing instrument includes a top section, a display screen and a bottom section. In some embodiments, the top section may include a deck supporting components of the sequencing instrument and consumables, including a sample preparation section, a sequencing chip and reagent strip tubes and carriers. In some embodiments, the bottom section may house reagent bottles used for sequencing and a waste container.

In some embodiments, one or more cameras mounted in a cabinet of the top section of the instrument is oriented towards the deck to monitor what items are in place in preparation for a sequencing run. The camera can acquire video or images at time intervals. For example, images may be acquired at 1-4 second intervals or any suitable interval.

In another example, frames of a video stream can be extracted at intervals such as in a range of 0.5 seconds to 4 seconds. A computer or processor analyses images to detect the completion of a task by the user. The computer or processor may provide feedback and instructions for the next task in the preparation via the display screen. The display screen may present graphical representations of the instrument components and consumables in order to illustrate instructions for the user.

Figure 2:
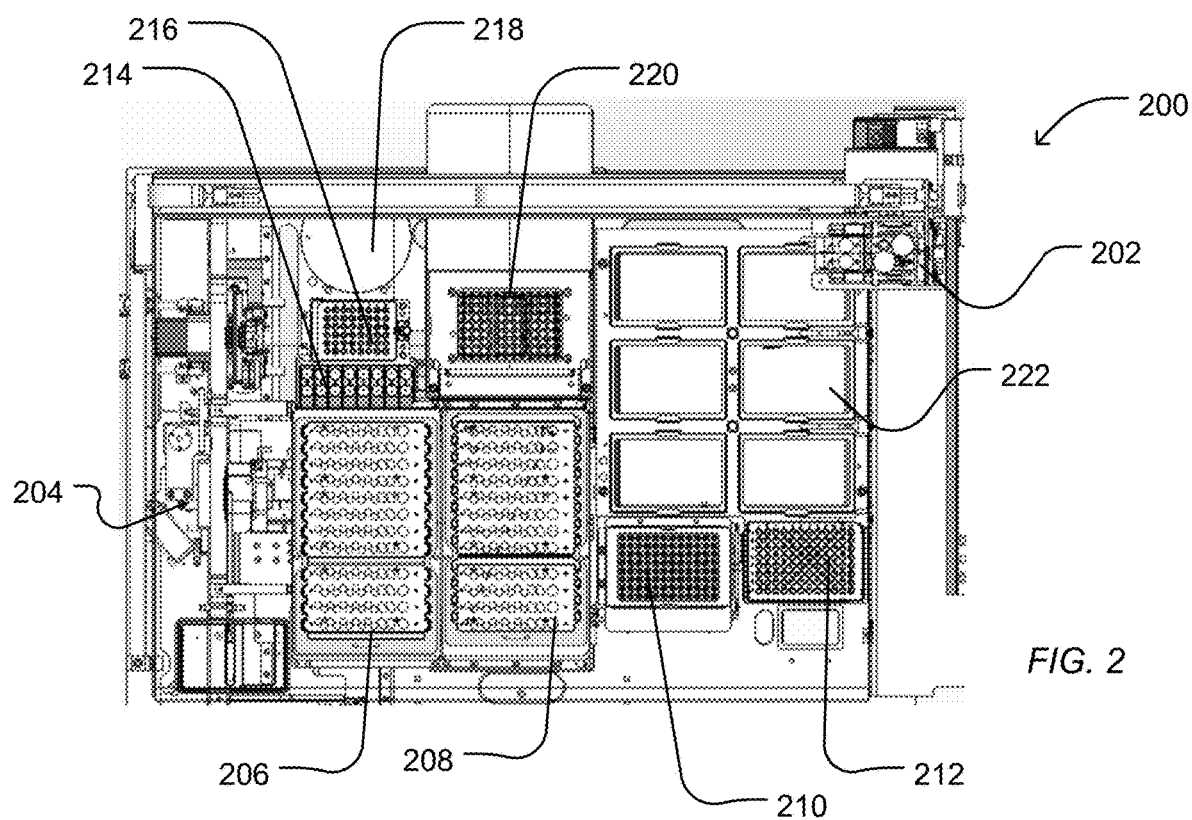
FIG. 2 includes an illustration of an example deck of an instrument.

An example instrument deck 110 is illustrated in FIG. 2 as instrument deck 200. The deck is housed in the top section of the instrument in the view of the camera or cameras. The sample preparation deck may include a plurality of locations configured to receive reagent strips, supplies, a sequencing chip, and other consumables. As used herein, consumables are components used by the instrument that are replaced periodically as they are used. For example, consumables include reagent and solution strips or containers, pipette tips, microwell arrays, and flowcells and associated sensors, among other disposable components not part of the permanent components of the instrument.

In an example, the system 200 includes a pipetting robot 202 that accesses various reagent strips and containers, pipette tips, microwell arrays, and other consumables to implement a test. Further, the system can include mechanisms 204 for carrying out testing. Example mechanisms 204 include mechanical conveyors or slides and fluidic systems.

In an example, the deck 200 includes trays 206 or 208 to receive solution or reagent strips of a particular configuration. In an example of a sequencing instrument, the tray 206 can be used for library and template solutions in appropriately configured strips, and the tray 208 can receive library and template reagents in the appropriate configuration.

Further, the instrument can be configured to receive microwell arrays 210 and 212 at particular locations on the deck. For example, a sample can be supplied in an array of wells, such as microwell array 212. In another example, the system can be configured to receive additional reagents 214 in a different strip configuration. In another example, reagent solutions can be provided in an array 216. In a further example, container arrays 220 can be provided in conjunction with instrumentation, such as a thermocycler. Further, the system can include other instrumentation, such as a centrifuge, that may be supplied with consumables, such as tubes. Further, trays can be provided to receive pipetting tips 222.

The appropriate provisioning of consumables in each of these locations can be monitored by a vision system including one or more cameras. The deck may be provided with one or more cameras to track provisioning and securing of reagents and other consumables. The user can be prompted through the user interface when a reagent is missing that is to be utilized to perform one plan or when a reagent consumable is present in a used state.

Figure 3:
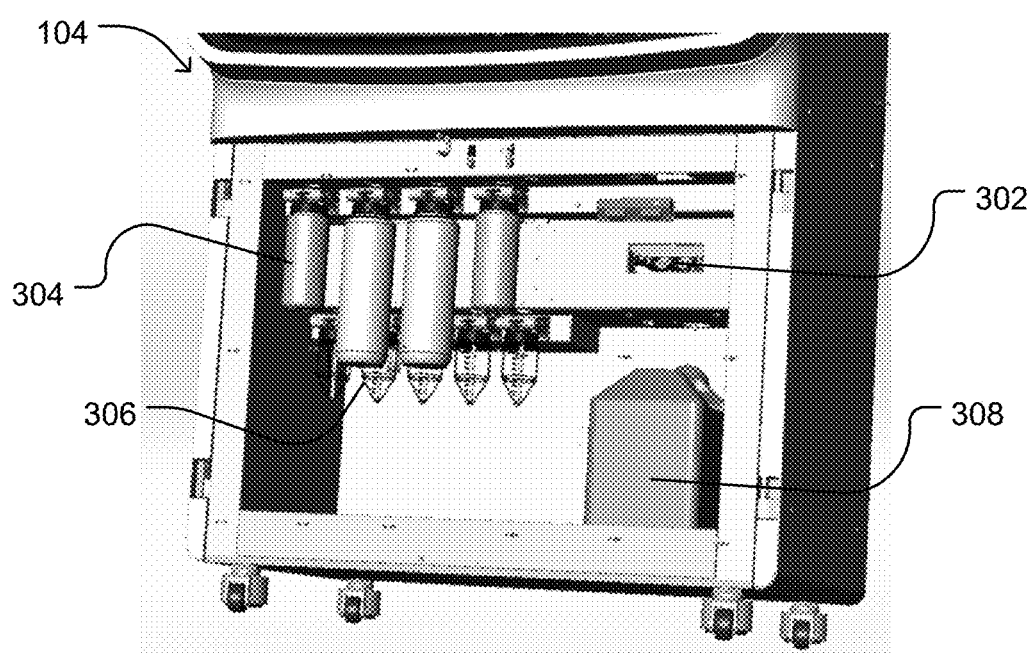
FIG. 3 includes an illustration of an example reagent storage for an instrument.

FIG. 3 includes an illustration of a reagent storage cabinet 104 to store larger volume reagent and solution containers. For example, the cabinet storage 104 includes an interface 302 to receive a reagent cartridge. In another example, the storage 104 can provide space for containers 304 or 306. In a further example, the storage 104 can include space for a waste container 308. As an alternative to the vision system, the reagent storage area 104 can utilize RFID tags and detectors to determine whether a reagent container is present.

Figure 4:
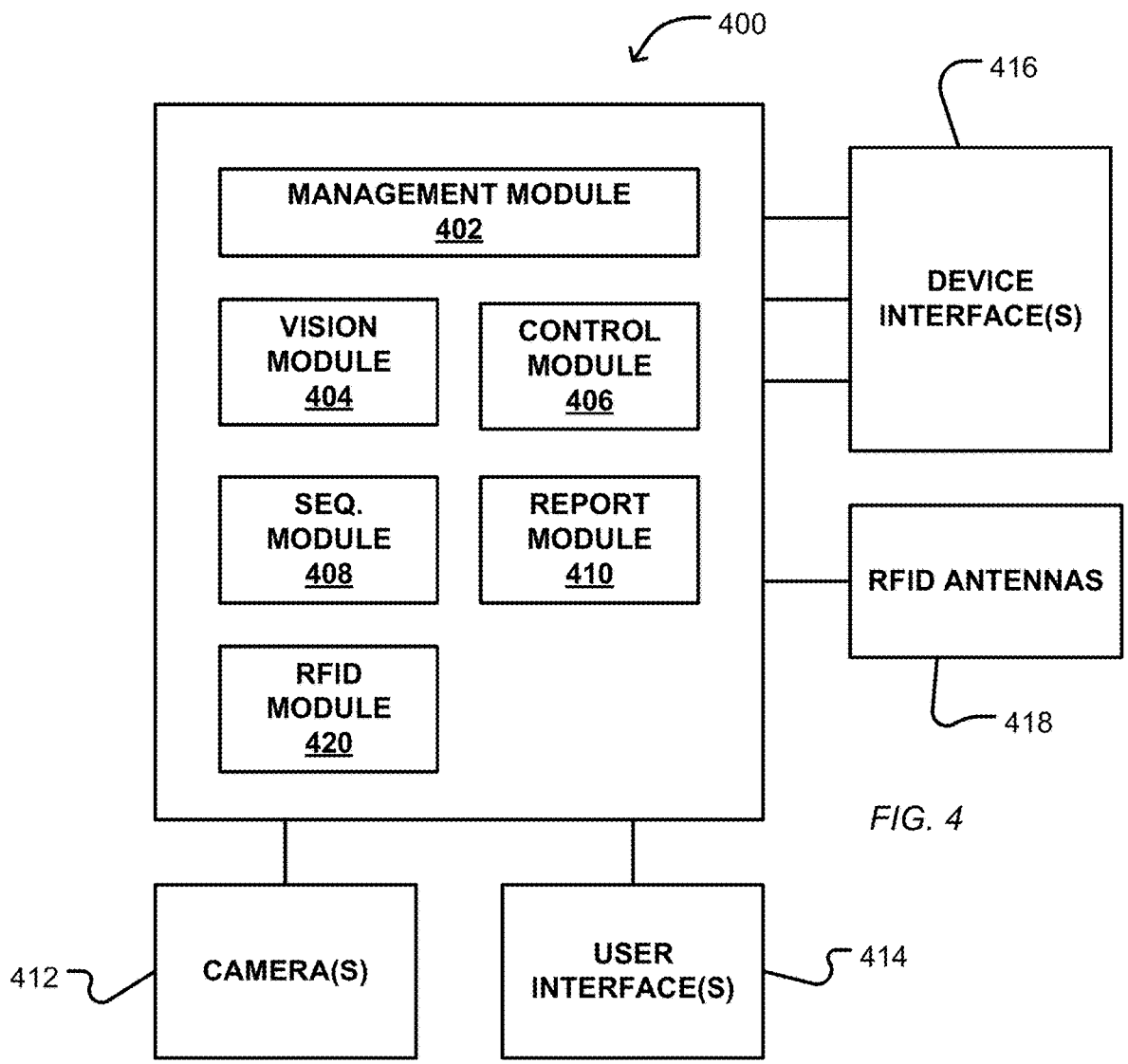
FIG. 4 includes an illustration of an example system for carrying out a test.

FIG. 4 includes an illustration of an exemplary system for interfacing with the instrumentation and devices of the instrument. In an example, FIG. 4 illustrates computational system 400. For example, the system 400 can include a management module 402 in communication with a vision module 404, a control module 406, sequencing module 408, a report module 410, and optionally, an RFID module 420. The management module 402 works with the various other modules 404, 406, 408, 410, or 420 to implement a run plan. A run plan includes an identification of one or more tests and associated parameters.

The vision module 404 can interact with cameras 412 to collect images that are analyzed to determine whether the instrument has been properly provisioned for a given run plan. In an example, the vision module 404 can collect pictures from the cameras 412. In another example, the vision module 404 collect frames of video taken by the cameras 412. In particular, frames can be extracted from a video stream at least every one second, two seconds, or five seconds. The vision module 404 can detect the presence of a consumable. Further, the vision system can detect whether the consumable has been used or is to be replaced.

The vision module 404 can use various techniques for determining the presence of a consumable and it state of use. For example, the vision module 404 can utilize heuristics to compare one or more pixels to expected values. In another example, the vision module 404 can utilize artificial intelligence, such as neural networks trained to detect features on the deck of an instrument.

The control module 406 can interact with various device interfaces 416 to implement testing in accordance with the run plan managed by the management module 402. For example, the control module 406 can interface with a three-axis pipetting robot to implement portions of a run plan. In another example, the control module can interact with other instruments associated with the instrument deck, such as a centrifuge, thermal cycling plate, magnetic separators, or microfluidic circuits.

The system 400 can further include an RFID module 420 that can interact with RFID antennas 418 to ascertain the presence of larger volume containers having an RFID tag. The system 400 may further track an amount of solution used from the container or sent to the container to determine whether remaining volumes are sufficient to complete a proposed run plan.

In the case of a sequencing instrument, the system 400 can further include a sequencing module 408 that interacts with the instrument to collect sequencing data. Further, the system can include a reporting module 410 to further process sequencing data and to provide a useful report, such as a variant call report, to a user.

To interact with users, system can further include user interfaces 414, such as computer screens, mice, keyboards, or touchscreens, among others, to interact with the user during run planning, instrument setup, and results reporting. In an example, the user interface interacts with the user to guide the user through provisioning and clearing of the instrument.

Figure 5:
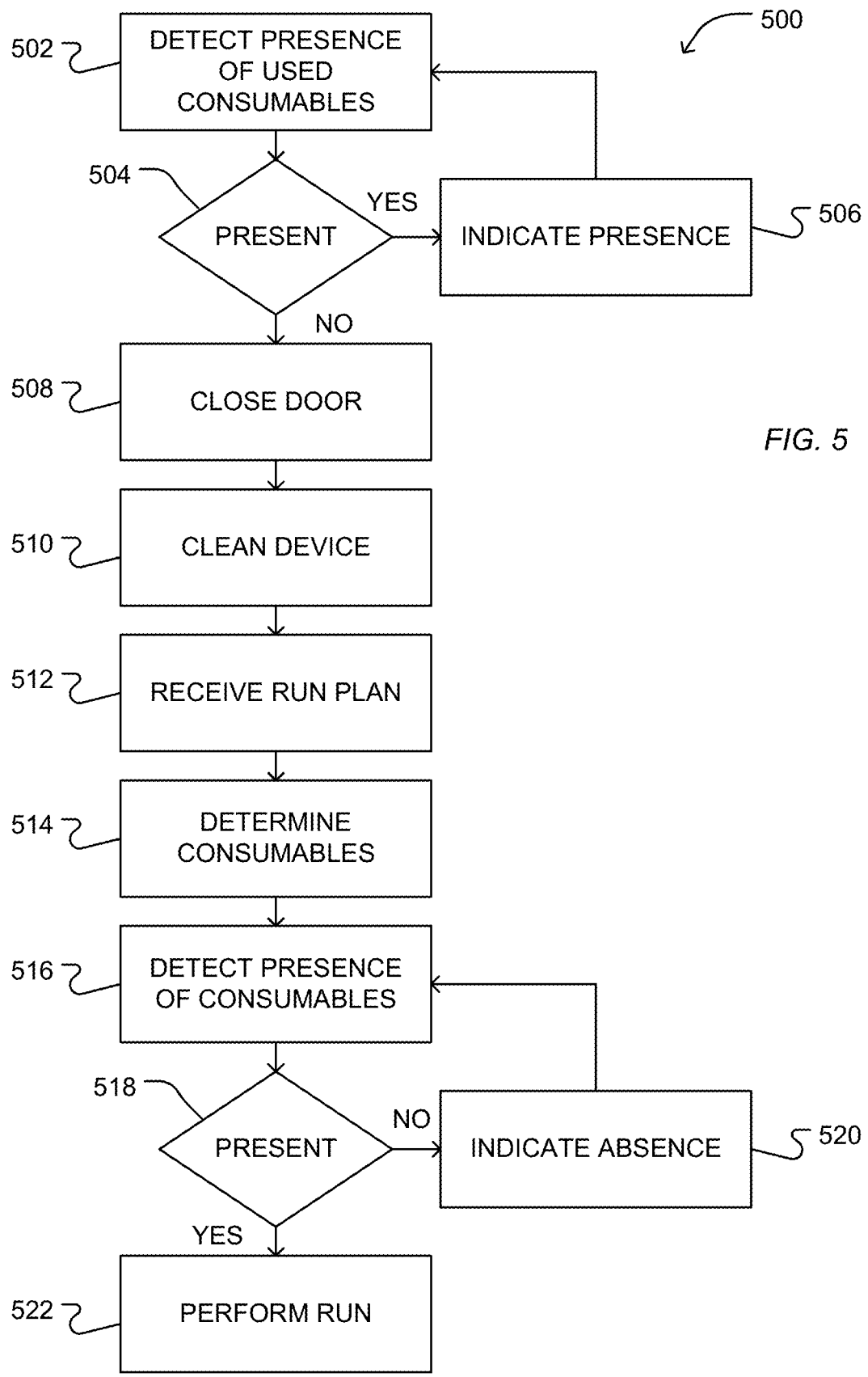
FIG. 5 includes illustration of an example method for initiating in instrument in preparation to run a test.

FIG. 5 includes an illustration of an example method 500 for initiating an instrument. For example, using a vision system, the system can detect the presence of used consumables, as illustrated at block 502. In particular, the vision system may detect that a foil has been punctured. In another example, the system can recognize a barcode of a sample and determine that the consumable has been used in a previous run. In another example, consumables can be detected with an RFID system and the consumables tracked to determine whether they have been used.

If the consumable is present, as illustrated at block 504, the presence can be indicated on the user interface, as illustrated at block 506. In particular, the presence can be indicated on a touchscreen. For example, a flashing icon over a background illustrating the deck of the instrument or the storage area can be used to indicate the presence of a used consumable to be removed. Alternatively, the presence can be indicated using sound or tactile indications. The process can be repeated until all of the used consumables have been removed from the device. At that time, the door to the instrument can be closed, as illustrated at block 508, and the instrument can initiate cleaning, as illustrated at block 510. For example, an internal deck can be exposed to ultraviolet light or cleaning solutions.

As illustrated at block 512, the system can receive a run plan for performing a particular test or tests. Alternatively, the system can receive the run plan prior to detecting the presence of used consumables. A given run plan or test utilizes a particular number and type of solutions and reagents, among other consumables. Accordingly, the system determines which consumables are to be provisioned for the run plan, as illustrated at block 514.

As illustrated at block 516, the presence of the consumables to be utilized for performing the run plan is detected. When the desired consumables are not present, as illustrated at block 518, the system can indicate their absence, as illustrated at block 520. For example, the system can prompt the user to locate a particular consumable and apply the consumable in a designated location on the instrument deck. In an example, the consumable to be supplied is named and illustrated over an illustration of the location at which the consumable is to be placed. For consumables below the deck, the system can alternatively detect their presence using RFID, and prompt the user to add the missing reagents or solutions. When all of the consumables to be used to perform the run plan are present, the instrument can perform the run, as illustrated at block 522.

Figure 6:
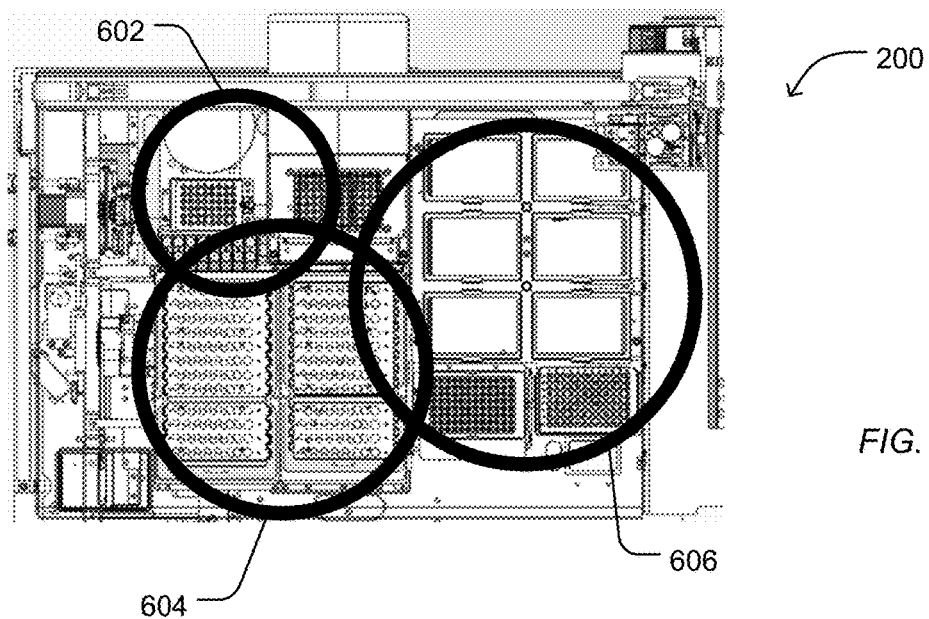
FIG. 6 includes an illustration of a coverage area of example cameras within a vision system.

In an example illustrated in FIG. 6, a vision system can include one or more cameras designated to observe portions of the deck 200. For example, a camera 602 can observed a certain portion of the deck for specific consumables. In another example, the camera 604 can observe reagent and solution trays. In a further example, a camera 606 can observe locations designated for providing unused pipetting tips and various microwell arrays. Further, an angle of the camera 606 can be angled in order to observe and read codes, such as barcodes or QR codes, displayed on an edge of a microwell array.

Figure 7:
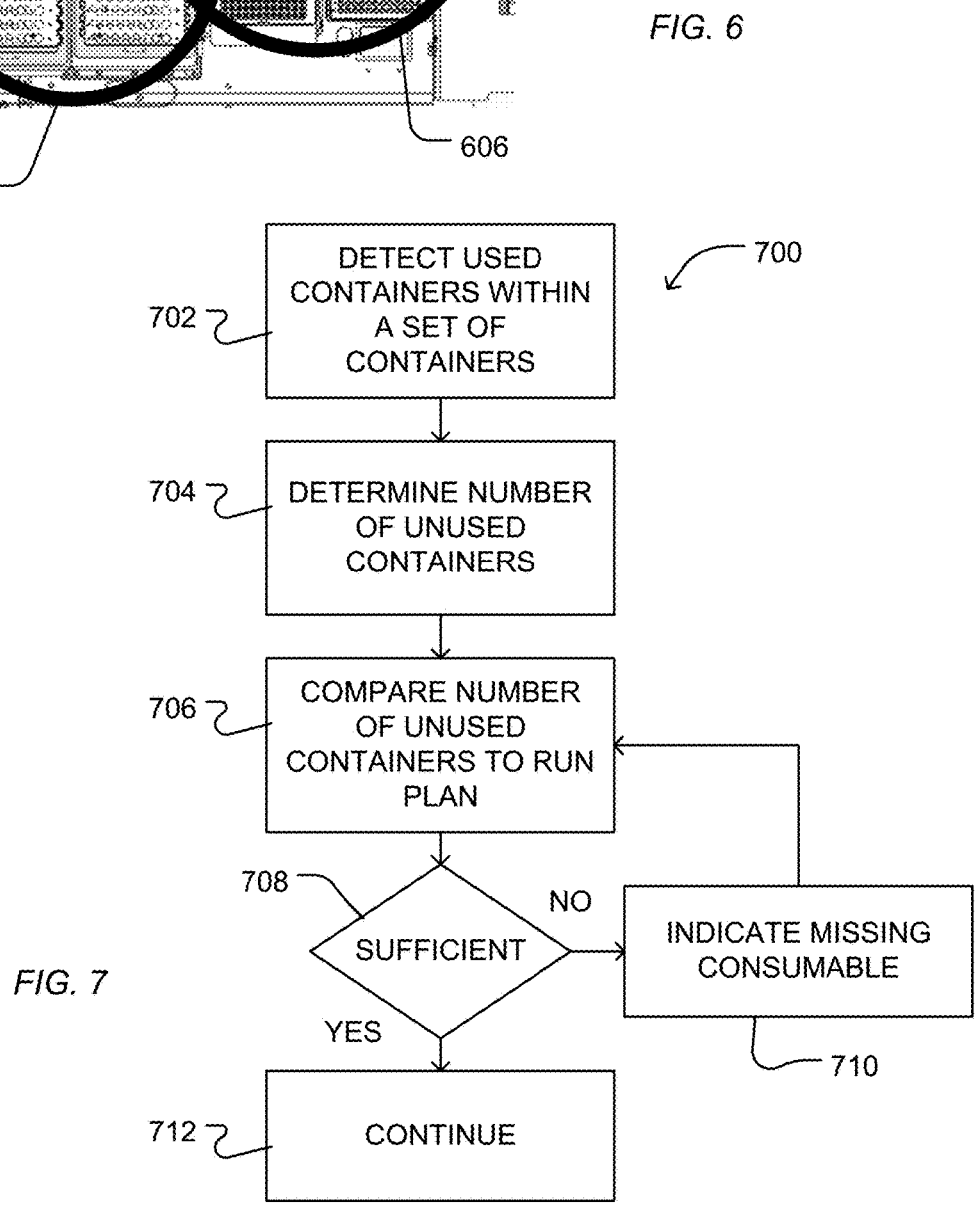
FIG. 7 includes a block flow diagram of an example method for initiating an instrument to run a test.

In an example, FIG. 7 illustrates a method 700 for initiating an instrument in preparation for runs. In particular, for consumables that can be used for multiple runs, the system detects whether or not a sufficient number of solution containers are available to complete a given run plan. For example, as illustrated at block 702, the system can detect used containers within a set of containers. The system can then determine a number of unused containers, as illustrated at block 704. The system can compare the number of unused containers to the run plan, as illustrated at block 706. If a sufficient number of containers is not found, as illustrated at block 708, the system can indicate the consumable as ready to be replaced, as illustrated at block 710. If there are a sufficient number of unused containers to run a given run plan, the system can continue along the initiating method, as illustrated at block 712.

In particular, detection of used containers can be performed using comparison of pixel values. In another example, the vision system can be trained to use artificial intelligent methods, such as neural networks, to determine or detect unused containers or used containers.

Figure 8:
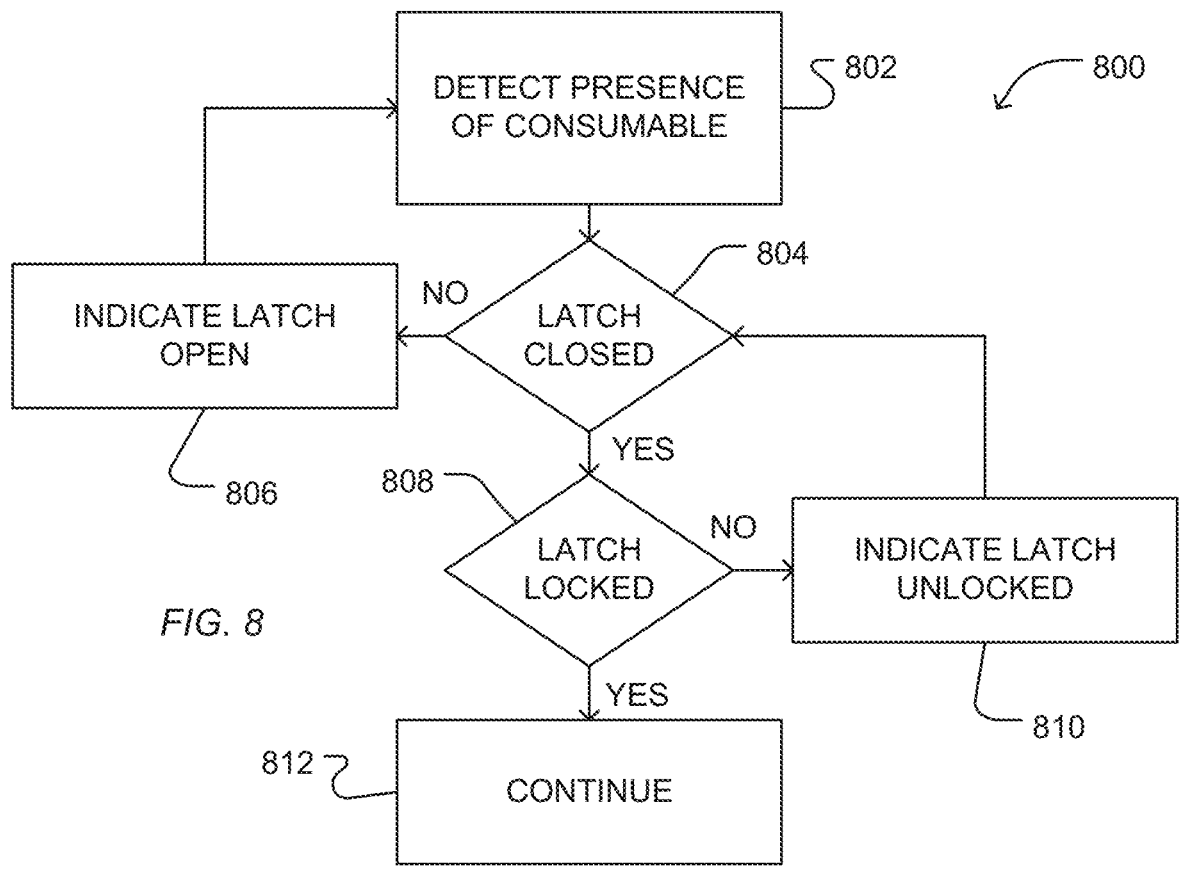
FIG. 8 includes a block flow diagram of an example method for initiating an instrument to run a test.

FIG. 8 includes an illustration of a method 800 for determining that a particular consumable is present and secured. For example, as illustrated at block 802, the system can detect the presence of the consumable. In an example, the consumable can have a code, such as a bar code or QR code, that can be read by the vision system to determine that the correct consumable is in place.

If the consumable has an associated latch to fold over the consumable to hold the consumable in place, the system can detect whether the latch is closed, as illustrated at block 804. In an example, the latch can include symbols, indicators, or dots printed on a top surface of the latch. Based on the presence of the symbols or their number, the system can determine whether the latch is closed or open. For example, the latch can have three indicators, such as dots, on a top surface of the latch. When the vision system detects the three dots, the latch is closed.

If the latch is not closed, the system can indicate to the user via the user interface that the latch is open, as illustrated at block 806. If the latch is closed, the system can determine whether the latch is locked, as illustrated at block 808. In an example, locking the latch may add a symbol or indicator for the vision system to detect. In another example, locking the latch hides a symbol or indicator. In the example of three dots, the lock may hide one of the dots. As such, if three dots are present, the latch is closed and unlocked. When two dots are present, the latch is closed and locked.

If the latch is not locked, the system can indicate that the latch is unlocked, as illustrated at block 810. If the latch is locked, the system can continue with initialization, as illustrated at block 812.

Figure 9:
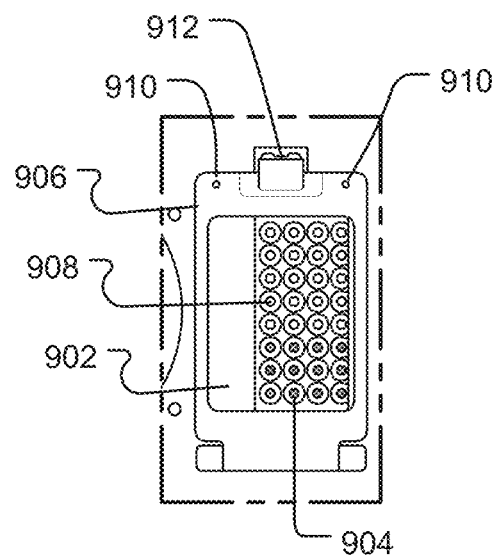
FIG. 9 and FIG. 10 include example images associated with initiating an instrument.

FIG. 9 includes an illustration of an example image taken in association with a consumable 902. For example, the consumable 902 has a set of containers. A subset of containers 904 has been used, while a different subset of containers 906 remain unused. For example, the system can detect that the foil has been pierced on the subset of containers 904 that have been used. When the latch 908 is positioned over the consumable 902, indicators can be present that are readable by the vision system to determine that the latch is closed. For example, the system may observe three dots 910 in a row indicating that the latch is in position or closed. In the absence of the latch being locked, three dots may appear. When the latch is both closed and locked, the clip 912 can block one of the indicators or dots 910. Accordingly, when the latch is not in position, no dots appear. When the latch is in position and not locked, three dots are present. When the latch is positioned and locked, two dots appear.

Figure 10:
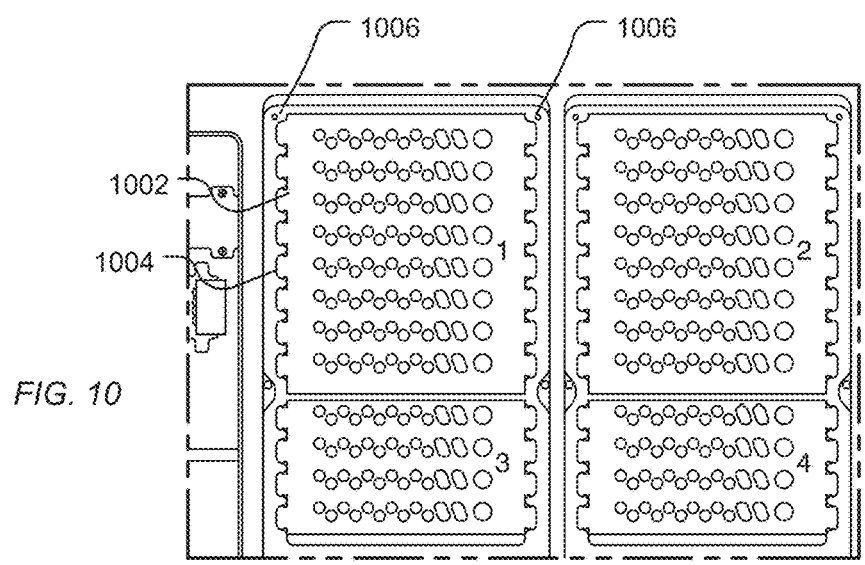

In another example illustrated in FIG. 10, slots 1002 for receiving a reagent strip are provided. A slidable lock 1004 can secure the reagent strips in place. The vision system can detect the location of indicators, such as indicator 1006 to determine whether the slide lock is in place or open.

Figure 11:
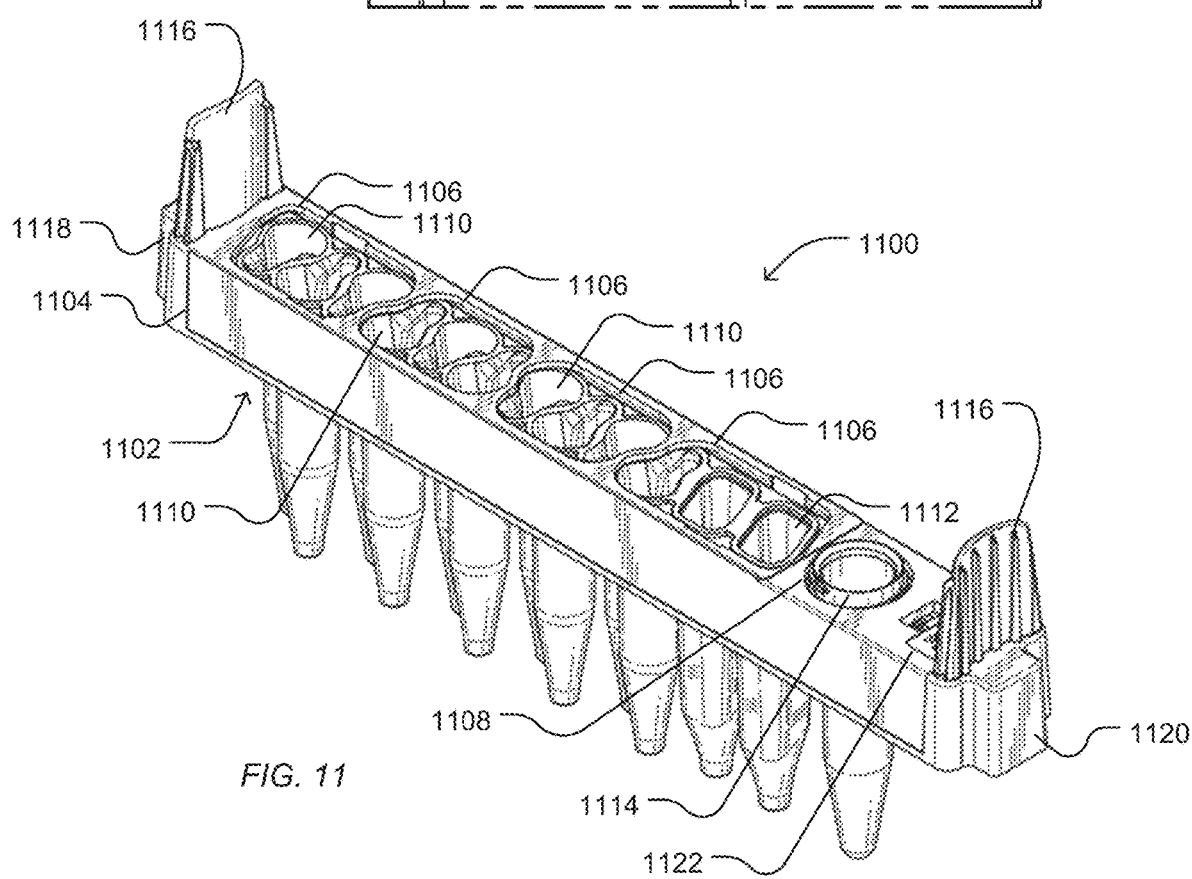
FIG. 11 includes an illustration of an example consumable.

An example consumable, such as a solution or reagent strip configured to fit in slot 1002 is illustrated in FIG. 11. In an example, the strip includes a base 1102 and a top 1104 coupled to the base 1102. The top 1104 includes windows 1106 that provide access to wells 1110 or 1112. Optionally, the top 1104 can provide a window 1108 to provide access to tube 1114 inserted into a tube receptacle of the base 1102.

The top can further include grips 1116. For example, the grips 1116 can be used to hold the reagent container 1100 when inserting or removing the reagent container 1100 from an analytical device. Further, the top 1104 can define end structures 1118 or 1120 configured to engage a complementary structure on the instrument and limit an orientation of the strip in relation to a position within the instrument. Further, a code 1122, such as a bar code or QR code, can be present on the top 1104.

Figure 12:
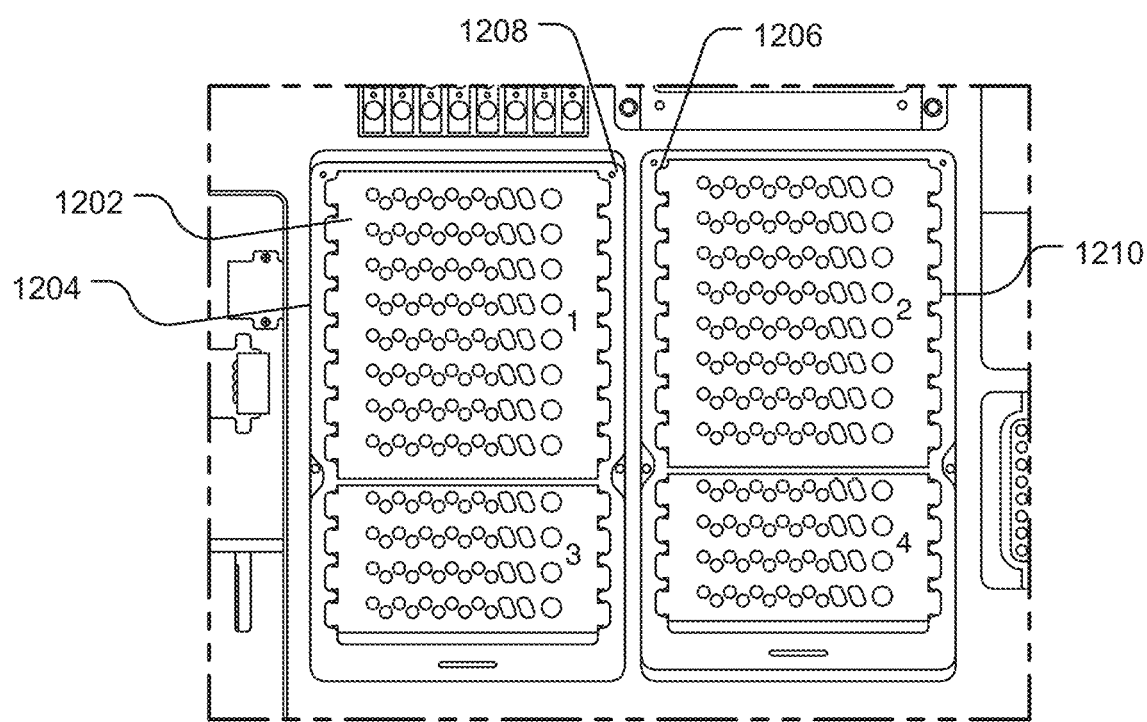
FIG. 12 includes an example picture of an instrument deck when initiating an instrument.

In particular, the vision system can detect the relevant relative position of indicators to determine whether the slide lock is open or closed. For example, as illustrated in FIG. 12, a slide lock 1204 is in the open position, while a slide lock 1210 is in the closed position. In the open position, a consumable, such as a solution or reagent strip, can be applied to the position 1202. As illustrated, an indicator such as a dot or symbol 1206 on the slide lock 1210 is positioned further into the instrument than a dot or symbol 1208 on the slide lock 1204, when the slide lock 1210 is in the locked position.

Figure 13:
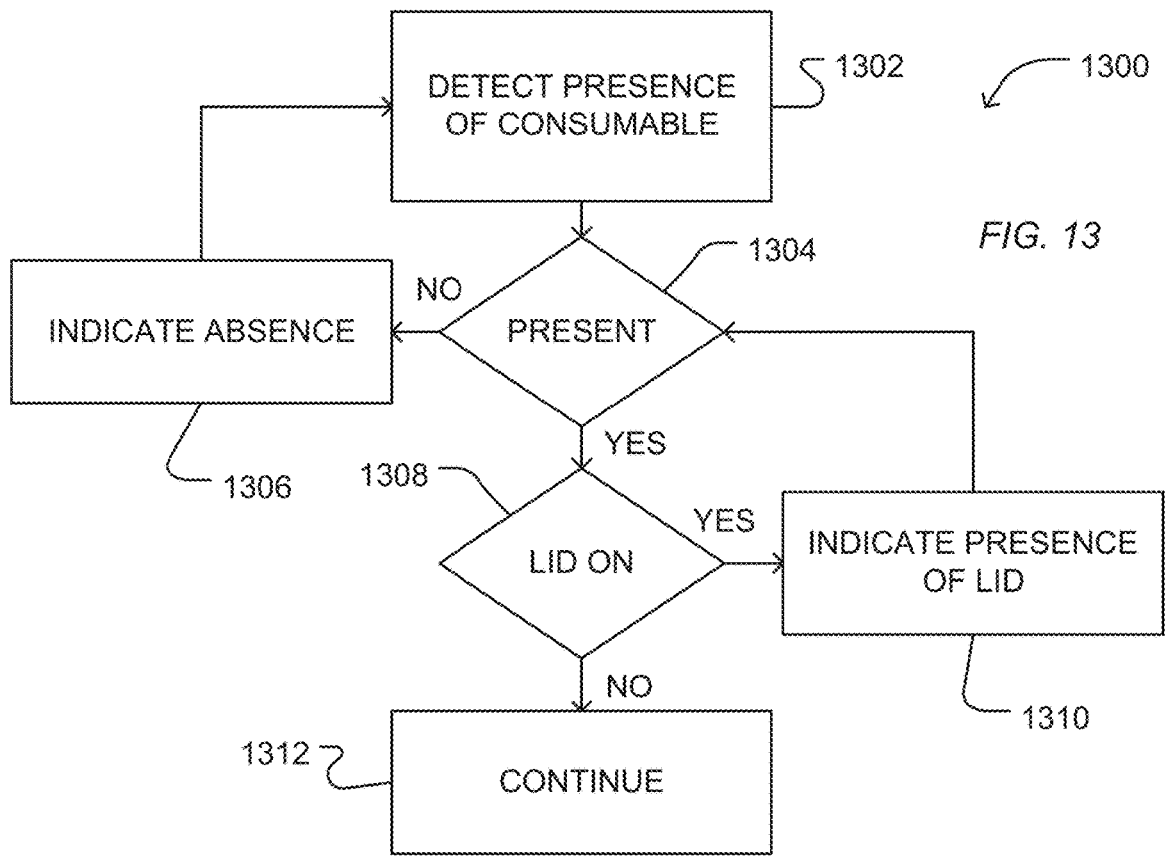
FIG. 13 includes a block flow diagram illustrating an example method for initiating an instrument.

As illustrated in FIG. 13, a method 1300 includes detecting the presence of the consumable, as illustrated at block 1302. When the consumable is not present, as illustrated at block 1304, the system can indicate through the user interface the absence of the consumable, as illustrated at block 1306. For example, the absence can be determined based on a feature that is detected by the vision system. The feature can include, for example, a symbol that would be covered in the presence of the consumable indicating the absence of the consumable. When the consumable is present, a different indicator symbol may be present, as well as a code, such as a barcode or QR code.

Particular consumables may further include or be supplied with a lid. As illustrated at block 1308, the system can determine whether the lid is on. If the lid is on, the system can indicate the presence of the lid, as illustrated at block 1310. If the lid is not on, the system can continue to initiate, as illustrated at block 1312.

Figure 14:
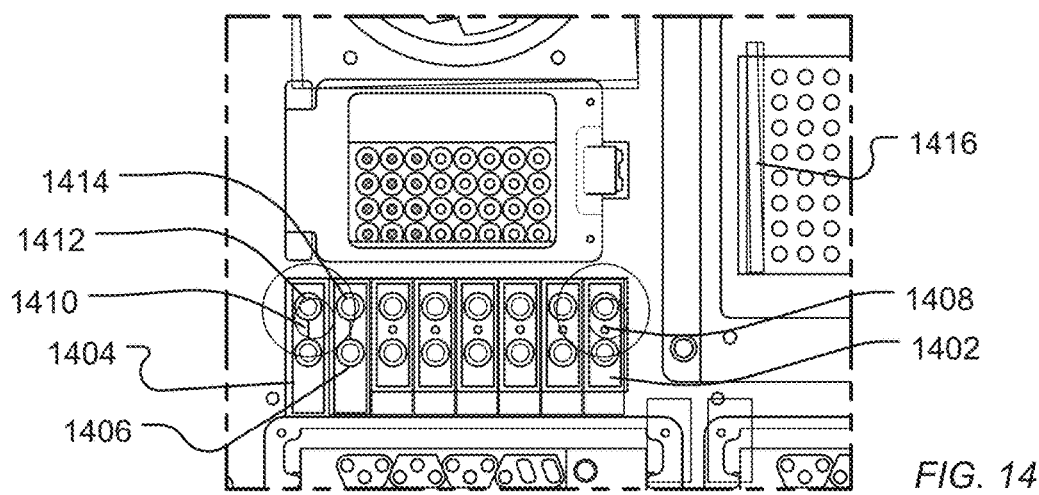
FIG. 14 includes an illustration of a portion of an instrument deck while initiating an instrument.

For example, as illustrated in FIG. 14, the deck may include slots 1402 to receive a consumable, such as a two-container consumable. In the absence of the consumable, a symbol or dot 1408 can be seen that would be covered in the presence of the consumable. For example, when the consumable is present, a consumable 1404 or a consumable 1406 block of the view of the symbol or dot 1408. A different symbol (e.g., a line) or the absence of a symbol, as illustrated at 1410, can indicate the presence of the consumable. The vision system can detect the presence of the symbols or dot or absence of such symbols or dots to determine whether a consumable is present.

When such a consumable is supplied with a lid 1412, the system can determine that a lid is on and direct the lid be removed. In particular, the lid may have a symbol on it that is readable by the vision system. In another example, pixel values can be compared to determine whether a lid is on or off. In a further example, the system can be trained with artificial intelligence to detect the presence 1412 of lid or the absence 1414 of the lid.

In a further example, the vision system can detect the presence of a consumable, such as an array, based on an ordered sequence of symbols, such as letters or number, as illustrated at 1416.

Figure 15:
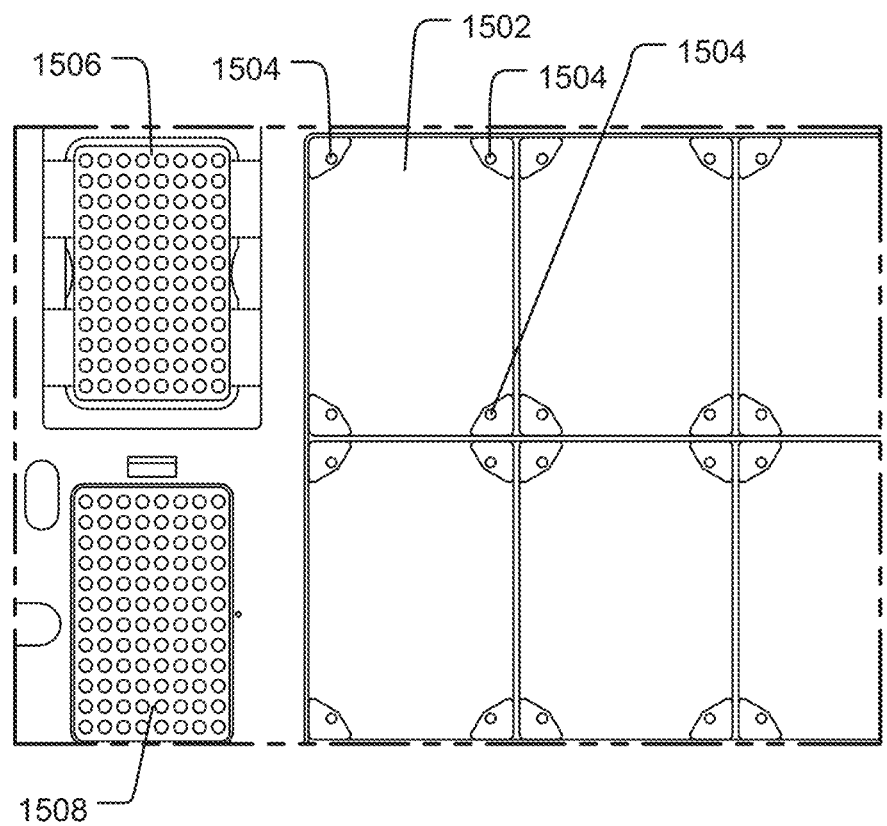
FIG. 15 and FIG. 16 include images of an example deck of an instrument.
Figure 16:
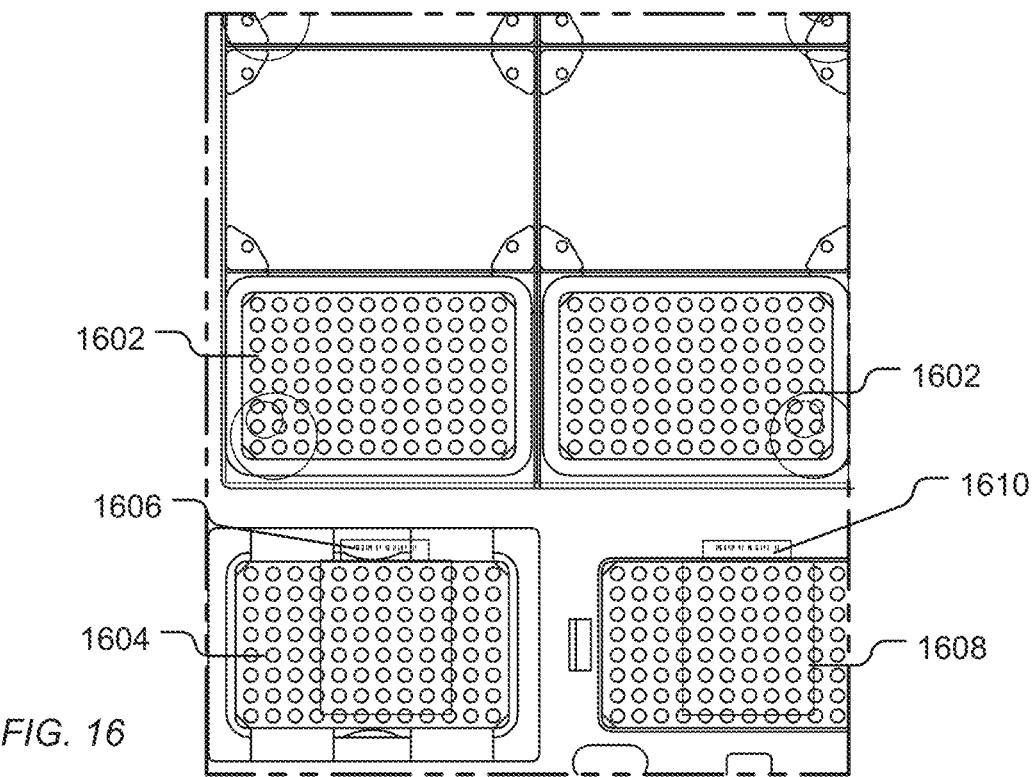

FIG. 15 and FIG. 16 include further illustrations for detecting the presence or absence of the consumable. For example, for a pipette tip tray, the location 1502 to receive the tray can include indicators 1504, such as dots or dark screws, detectable by the vision system. Similarly, empty receptacles 1506 and 1508 to receive microwell arrays can be detected based on the absence of a consumable, for example utilizing the presence of a symbol that would be blocked by the consumable or image processing or artificial intelligence to determine the absence of the consumable.

As illustrated in FIG. 16, when pipette tip trays 1602 are located in the appropriate location, the indicators 1504 are hidden. Similarly, when microwell arrays 1604 and 1608 are present, the system can both determine that presence based or the absence of markings associated with the receptacles 1506 or 1508. Further, the system may read codes, such as barcodes 1606 or 1610, to determine that the microwell array is in the correct location and is of the correct type.

Figure 17:
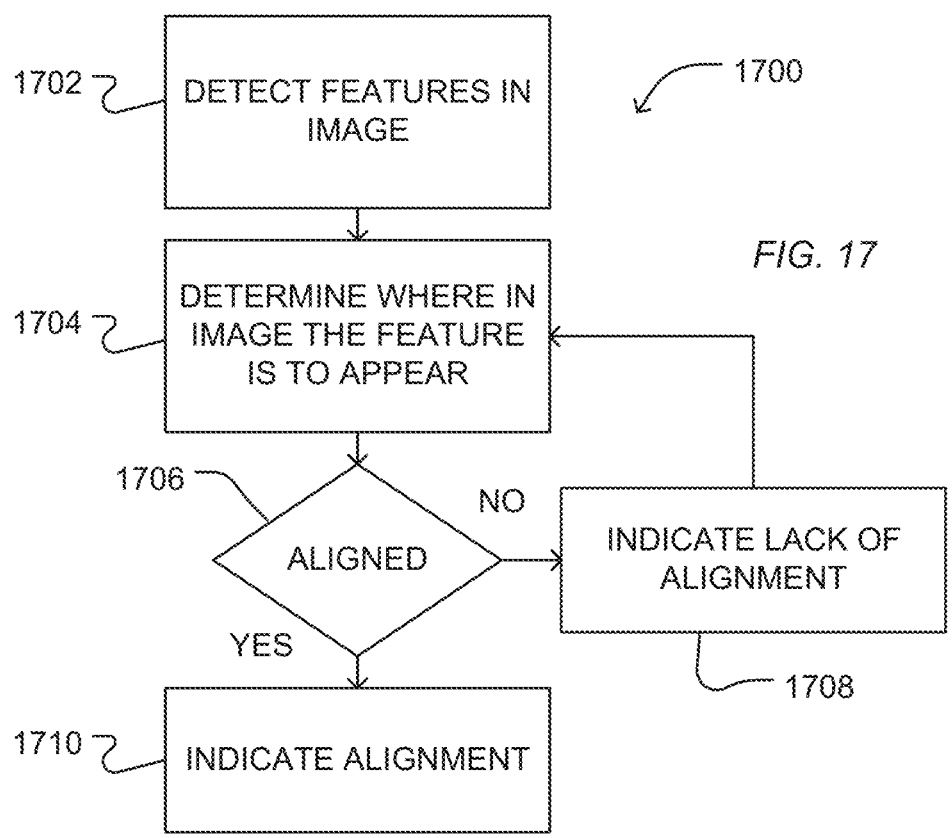
FIG. 17 includes a block flow diagram illustrating an example method for aligning cameras of the vision system.

FIG. 17 includes an illustration of an example method 1700 for aligning a camera system. The method 1700 includes detecting features in an image, as illustrated at block 1702. Such features can be indicators, symbols or dots, such as those described above. In another example, features may be various aspects or geometries of an instrument deck as imaged by cameras directed at the deck.

As illustrated at block 1704, the system can determine where in a given image the feature is to appear. In other words, the feature has an expected location within a given image and may be detected at a location other than the expected location. When the feature is not aligned with where the feature is to appear in a given image, as illustrated at block 1706, the system can indicate a lack of alignment, as illustrated at block 1708. The process can be repeated, for example, as a technician attempts to align the detected feature within an image and the expected location of that feature within the image, as illustrated at block 1710.

Figure 18:
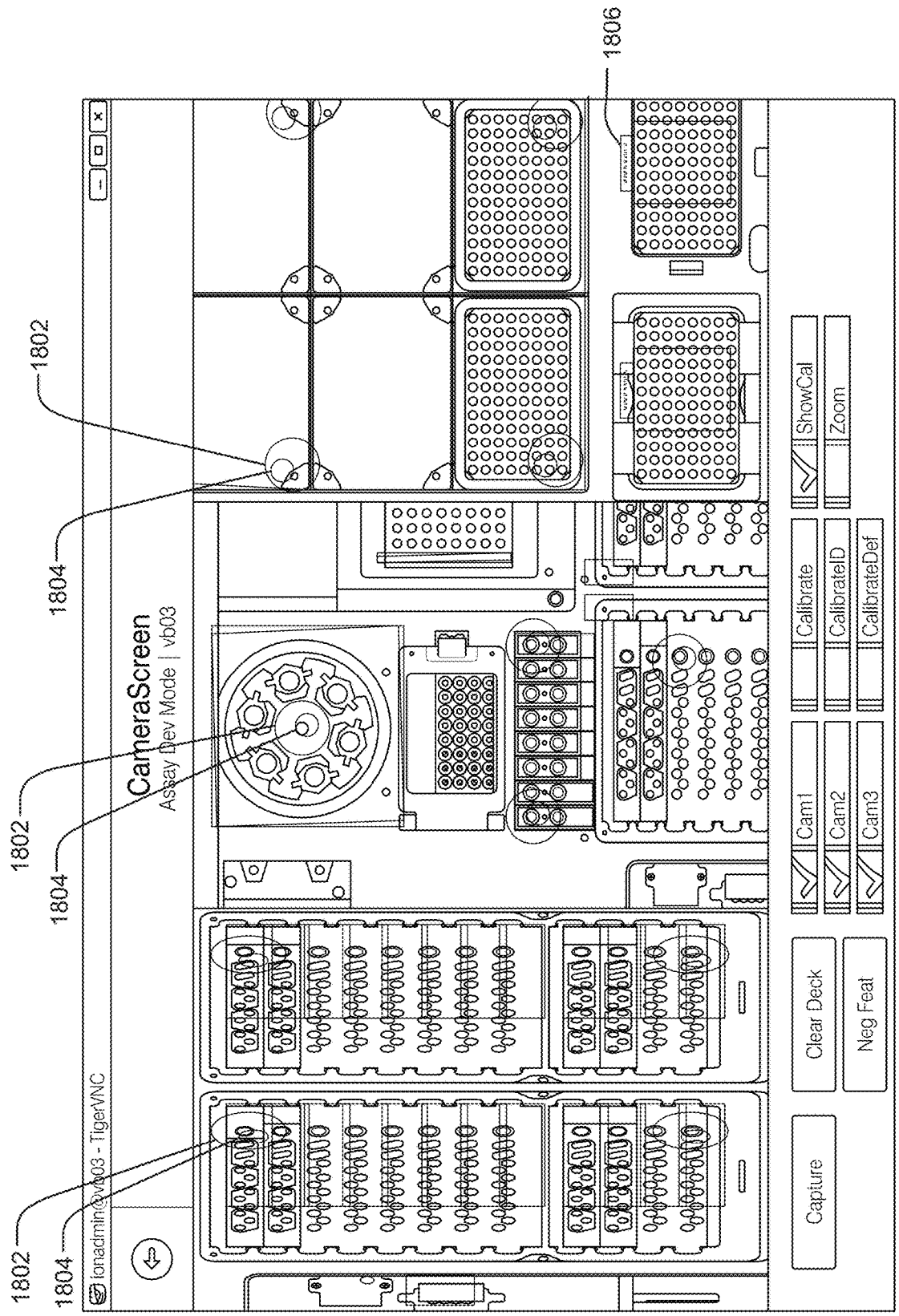
FIG. 18 includes a picture of an example video stream for aligning cameras with an instrument.

For example, as illustrated in FIG. 18, a feature can be identified and a region around the detected feature 1802 can be indicated on the user interface. The system can further draw the expected location 1804 of that feature within the image. In practice, frames can be extracted from real-time video or the real-time video can be displayed on a user interface with the overlying circles. Accordingly, a technician can align the cameras so that the feature location and its expected location within an image overlap. In another example, a camera can be adjusted based on whether it can read a code 1806 on the side of a consumable.

In some embodiments, radio frequency identification (RFID) tags may be attached to the reagent bottles and the nucleotide cartridge. An RFID sensor may be located in the bottom section in communication with the computer or processor. The RFID sensor may detect the presence of particular reagent bottles and the nucleotide cartridge. The computer or processor may analyze the detected information about the reagent bottles and nucleotide cartridge from the RFID sensor and provide feedback information to the user via the display screen.

Figure 19:
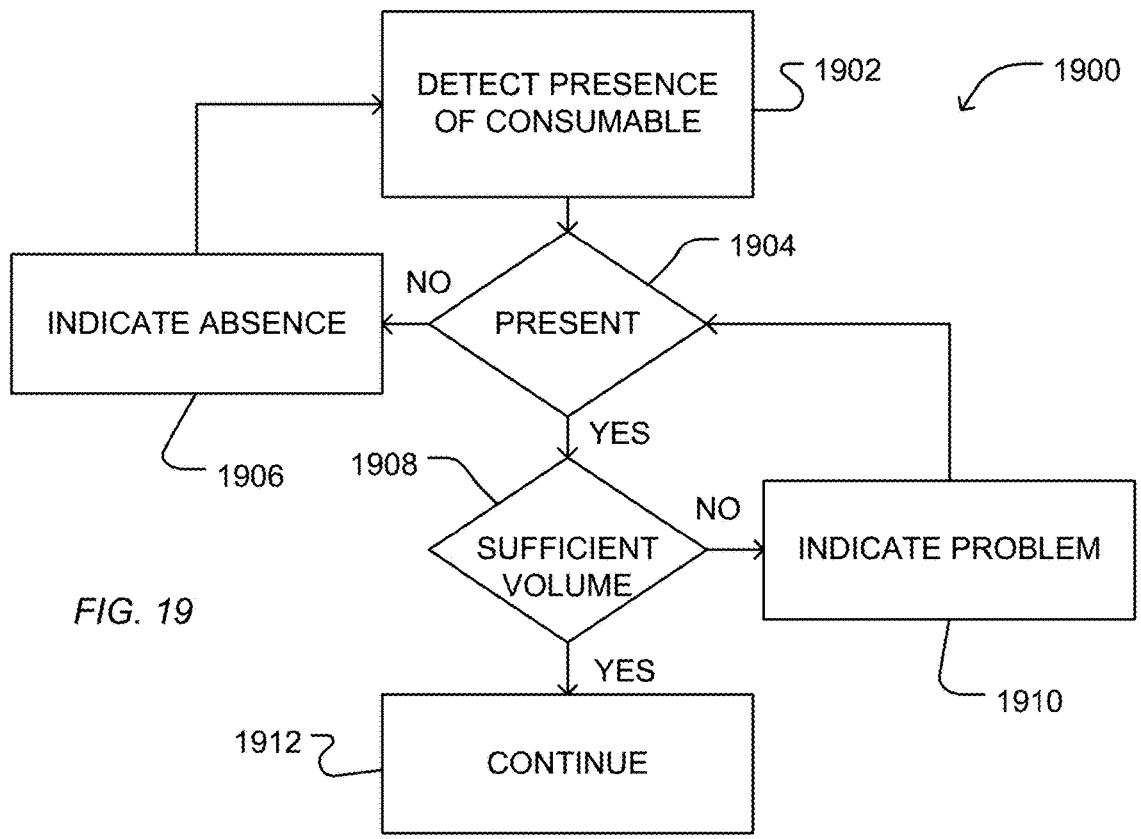
FIG. 19 includes an illustration for a block flow diagram illustrating an example method for initiating an instrument.

In a further example illustrated in FIG. 19, method 1900 for initiating an instrument includes detecting the presence of a consumable, as illustrated at block 1902. In particular, the consumable may be detected based on its RFID code. In the cases of larger volume containers useful for more than one run, the system can track its use and determine whether it is to be replaced. For example, the system can determine the presence of the consumable, as illustrated at block 1904. When the consumable is not present, the system can indicate its absence, for example, on a user interface using a flashing or alternatively colored icon, as illustrated at block 1906.

For the detected consumable, the system can determine whether the consumable has sufficient volume remaining following previous runs to meet the uses of the current run plan, as illustrated at block 1908. When there is not sufficient volume, the system can indicate a problem, as illustrated at block 1910, for example, to replace the consumable. If the consumable has sufficient volume, the system can continue its initiation, as illustrated at block 1912.

Figure 20:
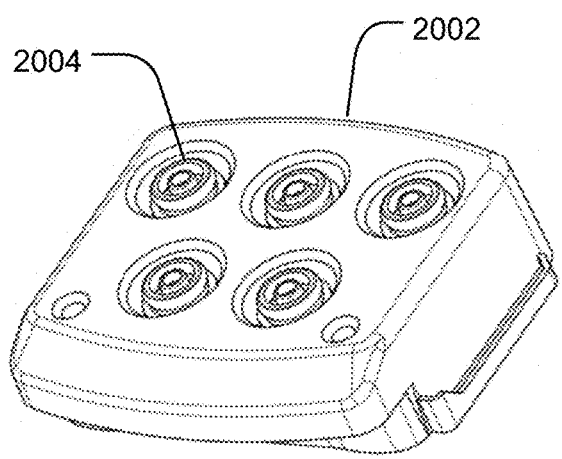
FIG. 20 and FIG. 21 include illustrations of example consumables associated with an instrument.
Figure 21:
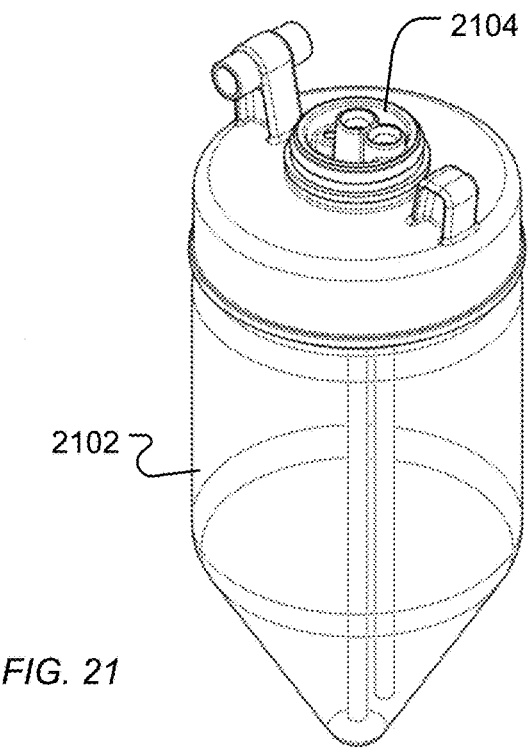

For example, FIG. 20 includes an illustration of an example consumable within a reagent storage of the instrument. For example, the cartridge 2002 includes various reagents containers 2004 useful in initiating a device. As illustrated in FIG. 21, a bottle 2102 includes a fluid interface 2104 to connect with an instrument. The system can track volumes of previous runs to determine whether sufficient volume remains within a container such as container 2102 or whether reagents of the cartridge 2002 are to be replaced.

Figure 22:
FIG. 22-FIG. 93 include illustrations of example screenshots associated with initiating instruments for running tests.
Figure 93:
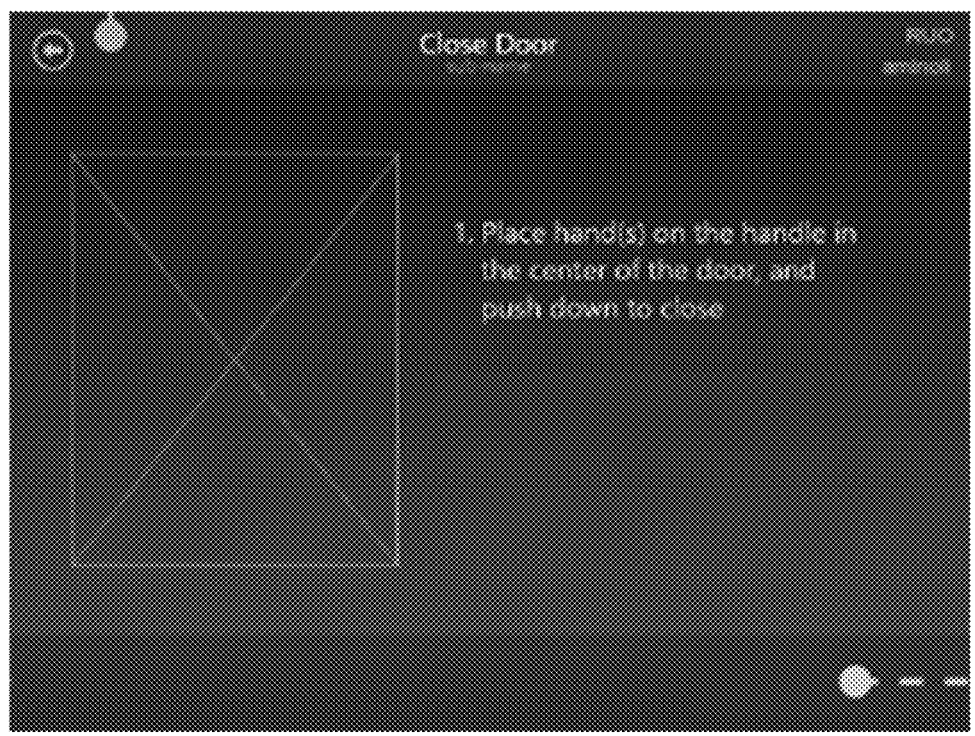

FIGS. 22 to 93 are examples of graphical displays that may be presented to the user on the display screen. These graphical displays guide the user through a series of steps to prepare the instrument, for example, for a sequencing run.

Figure 23:
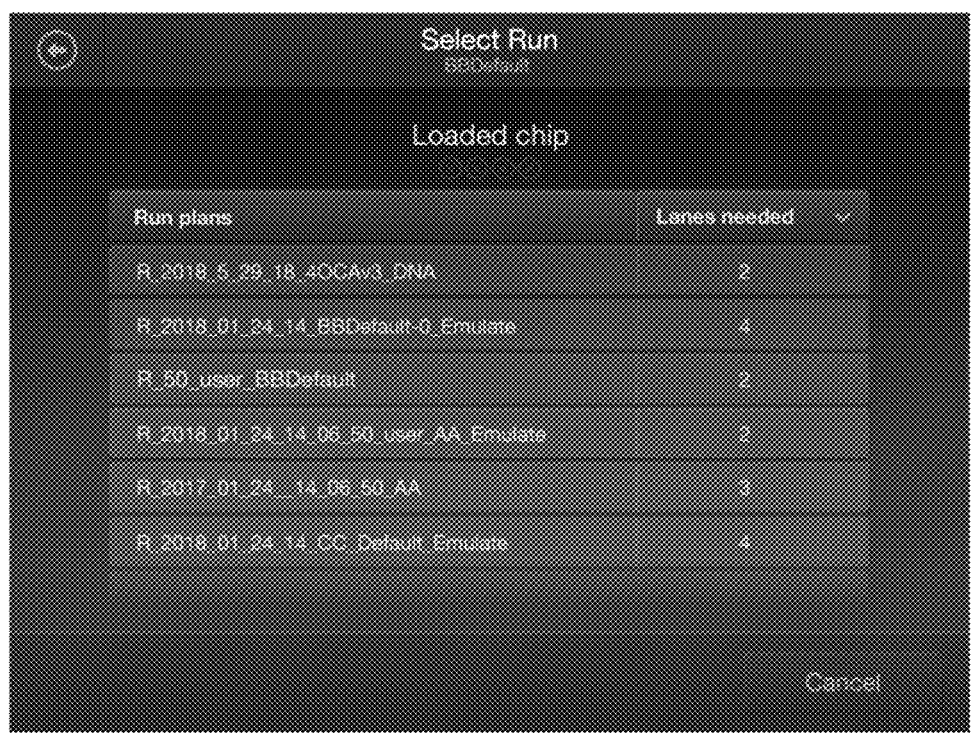
Figure 24:

FIGS. 22 to 24 illustrate examples of displays that pertain to the selection of the type of sequencing run to be prepared as part of proposing a run plan. FIG. 23 illustrates an example of several run plans that are selectable by the user.

Figure 25:
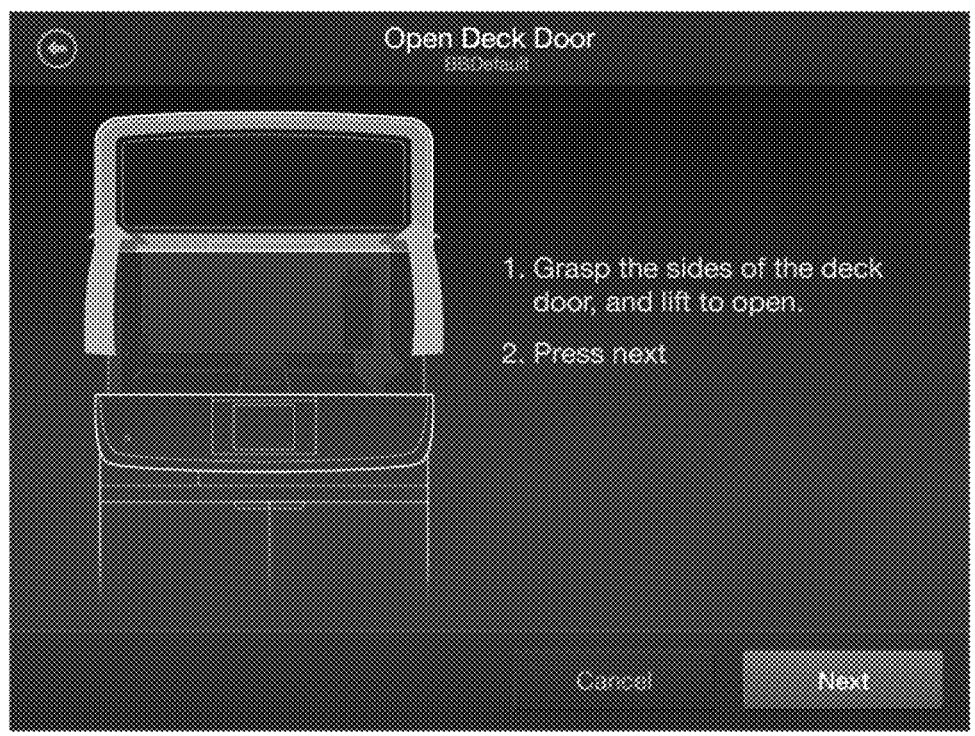

FIG. 25 illustrates an example of a graphical display that instructs the user to open the door of the deck located in the top section of the sequencing instrument, as shown in FIG. 1.

Figure 26:
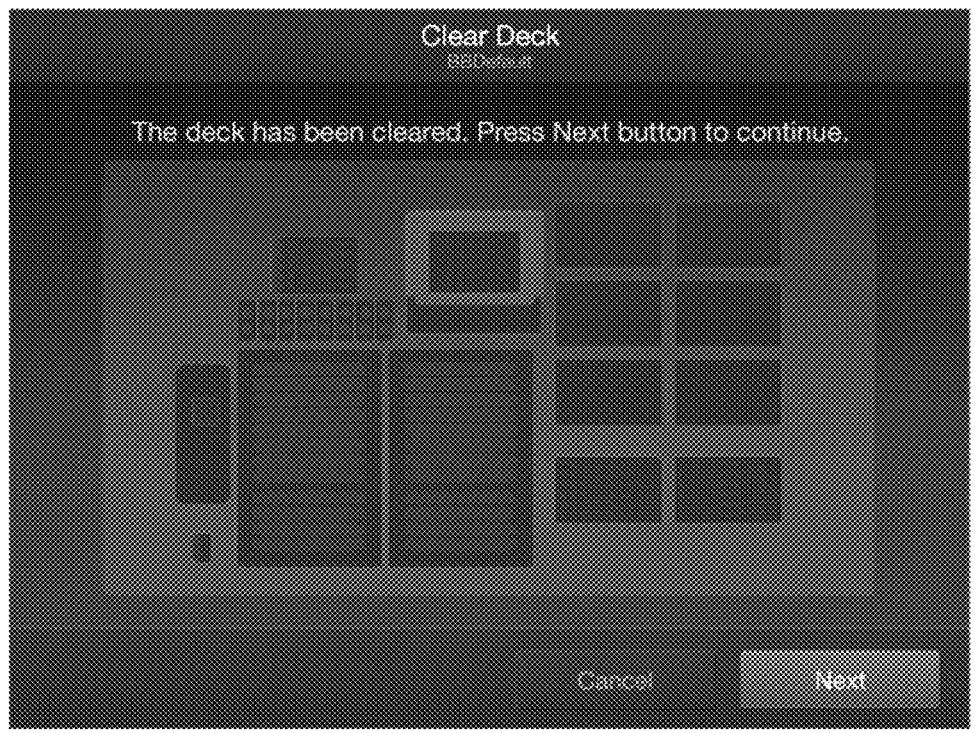
Figure 27:
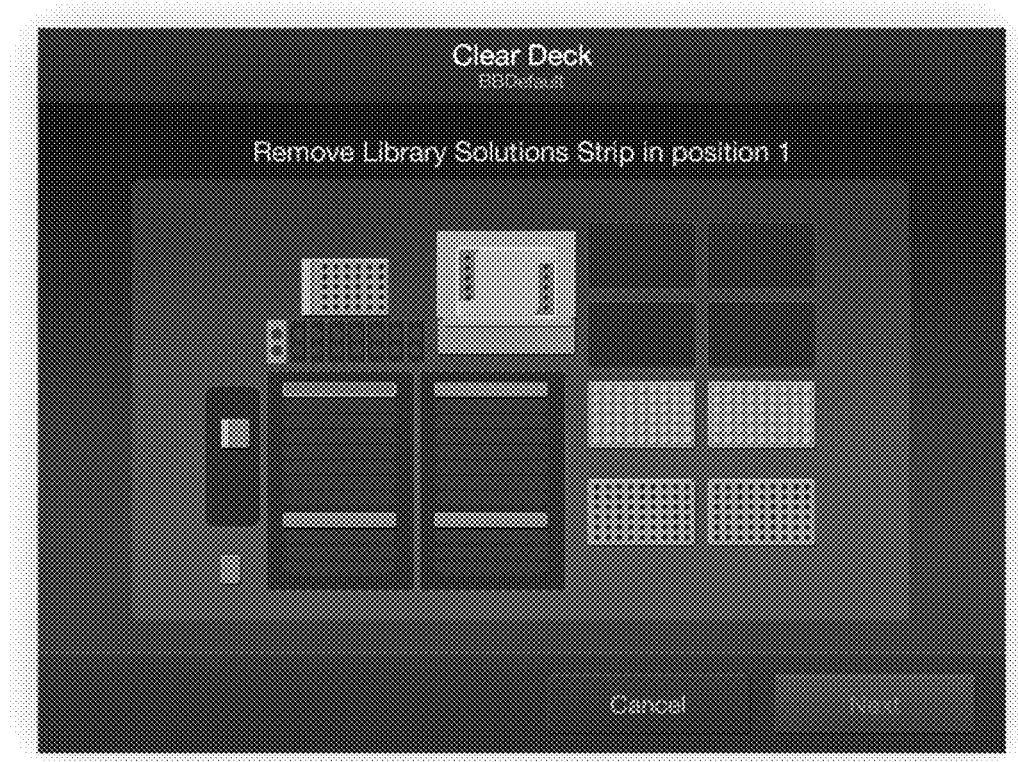
Figure 28:
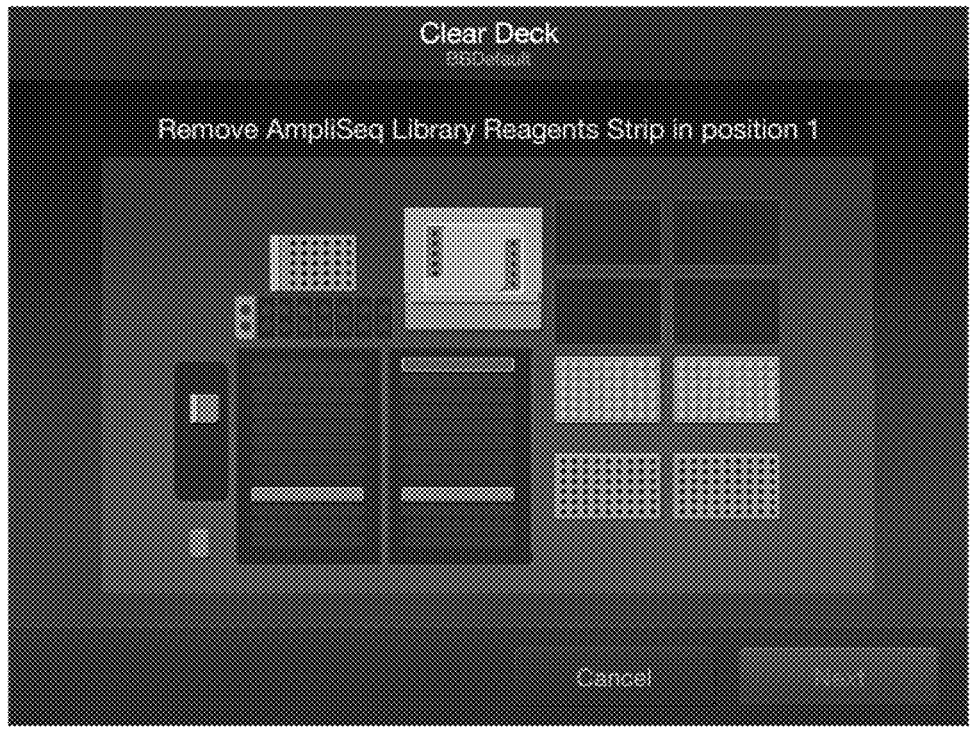
Figure 29:
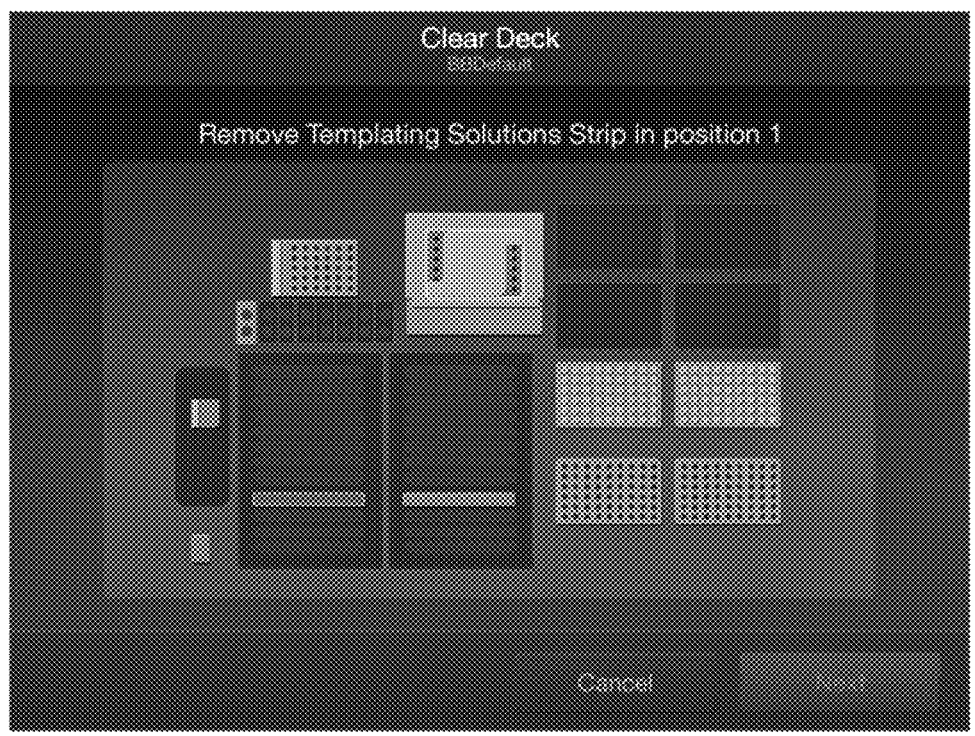
Figure 30:
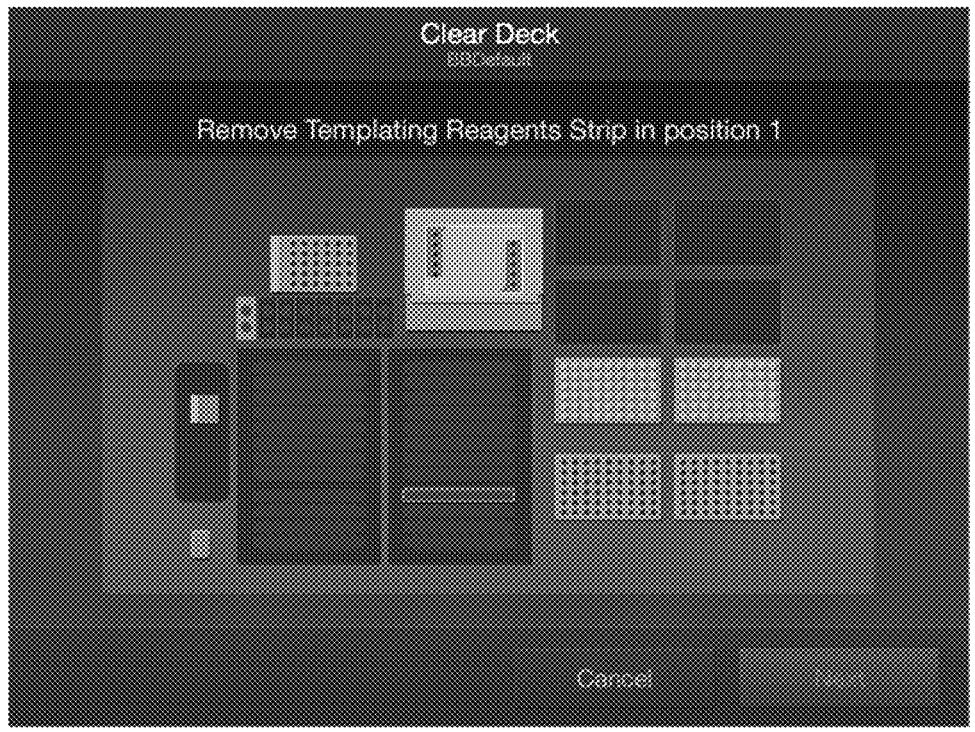
Figure 31:
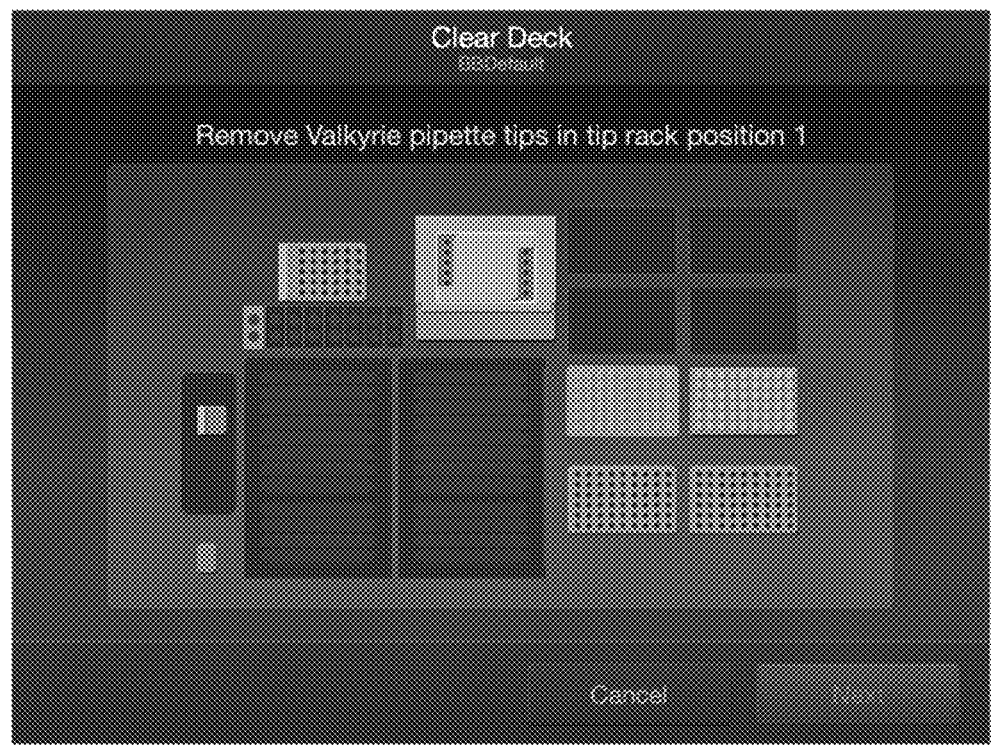
Figure 32:
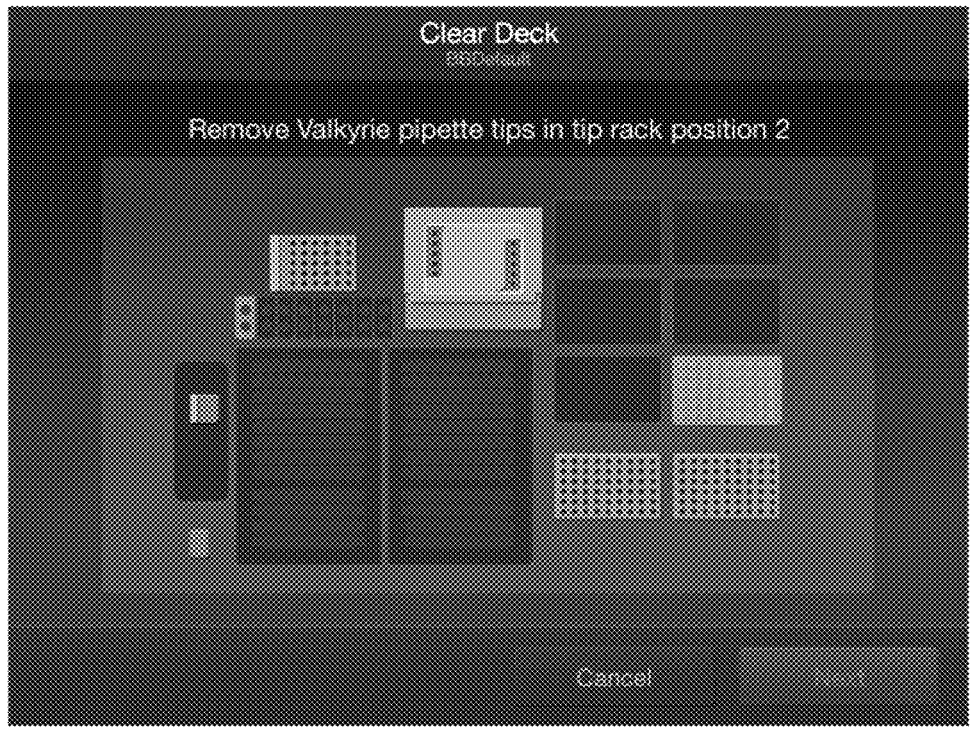
Figure 33:
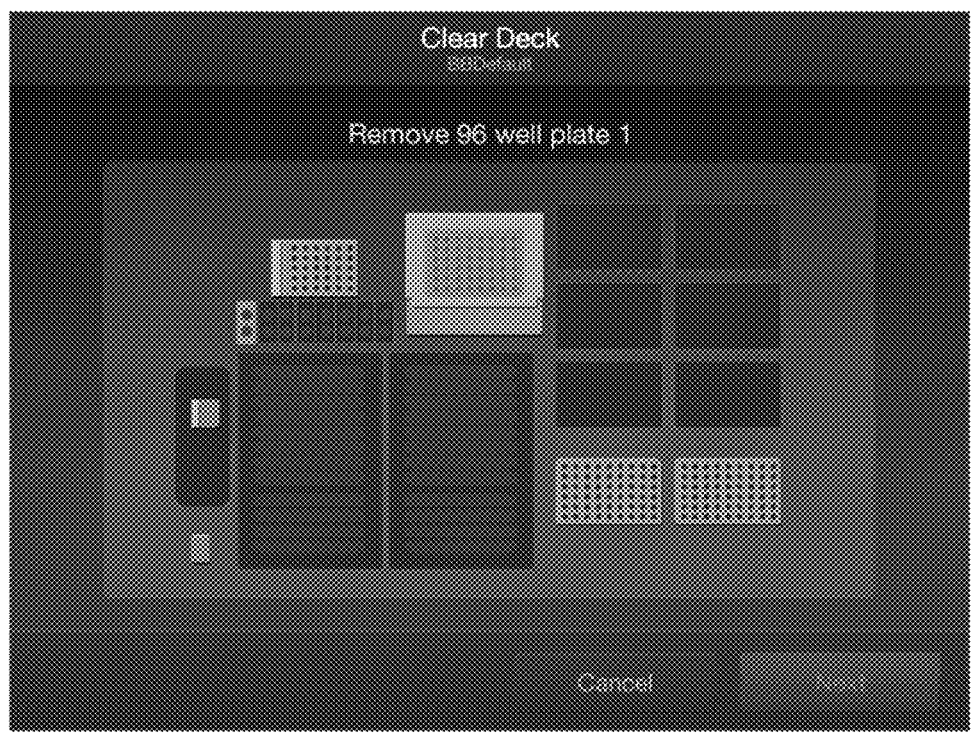
Figure 34:
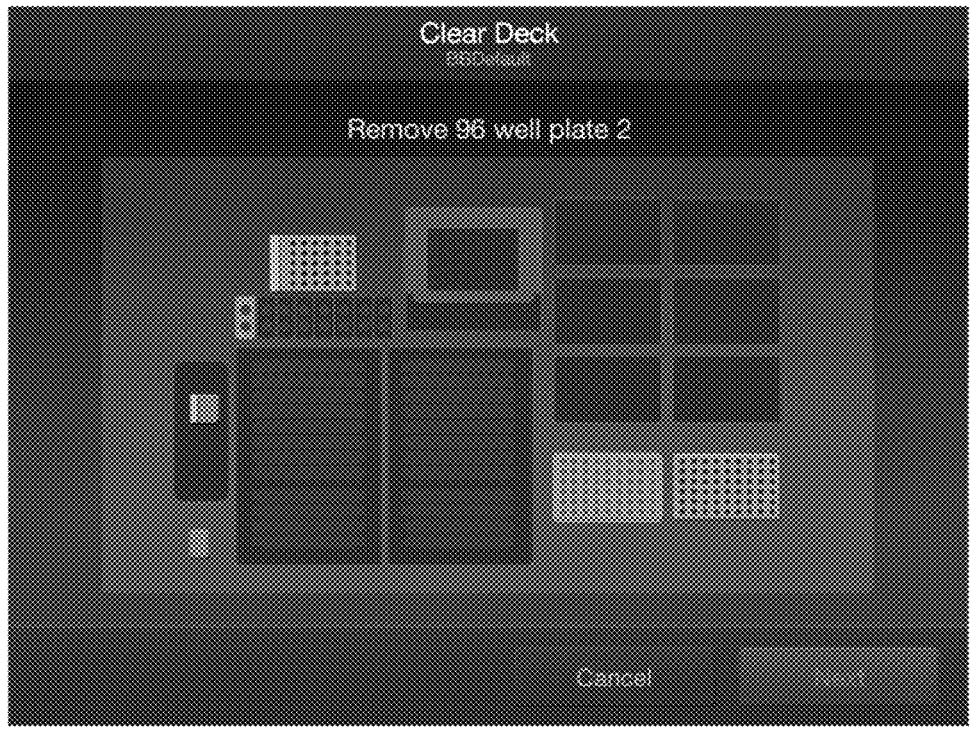
Figure 35:
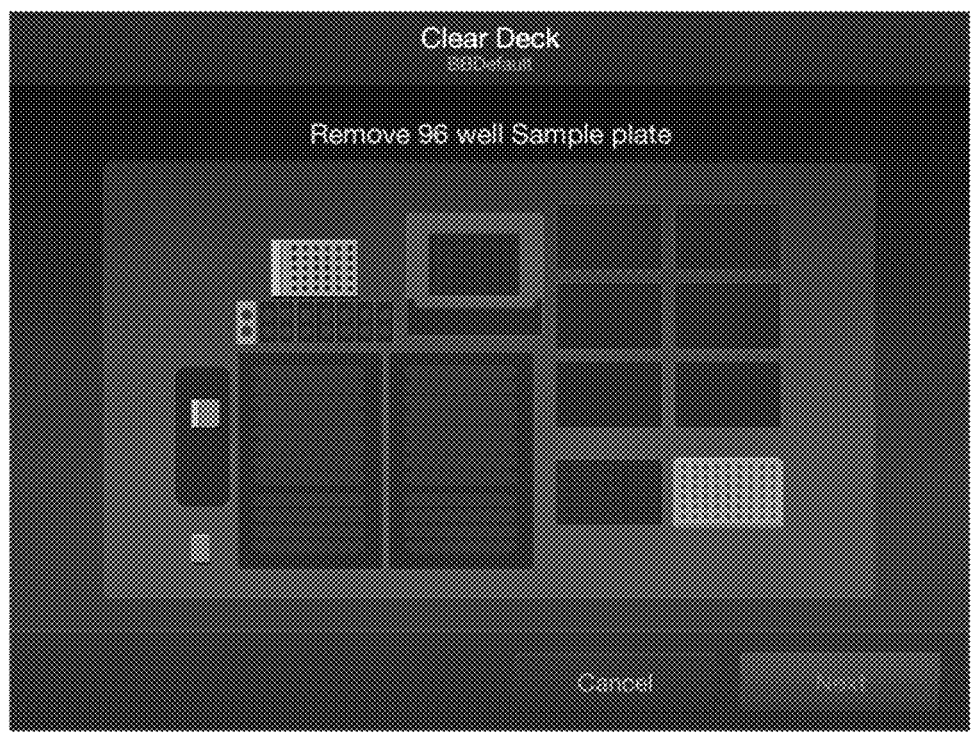
Figure 36:
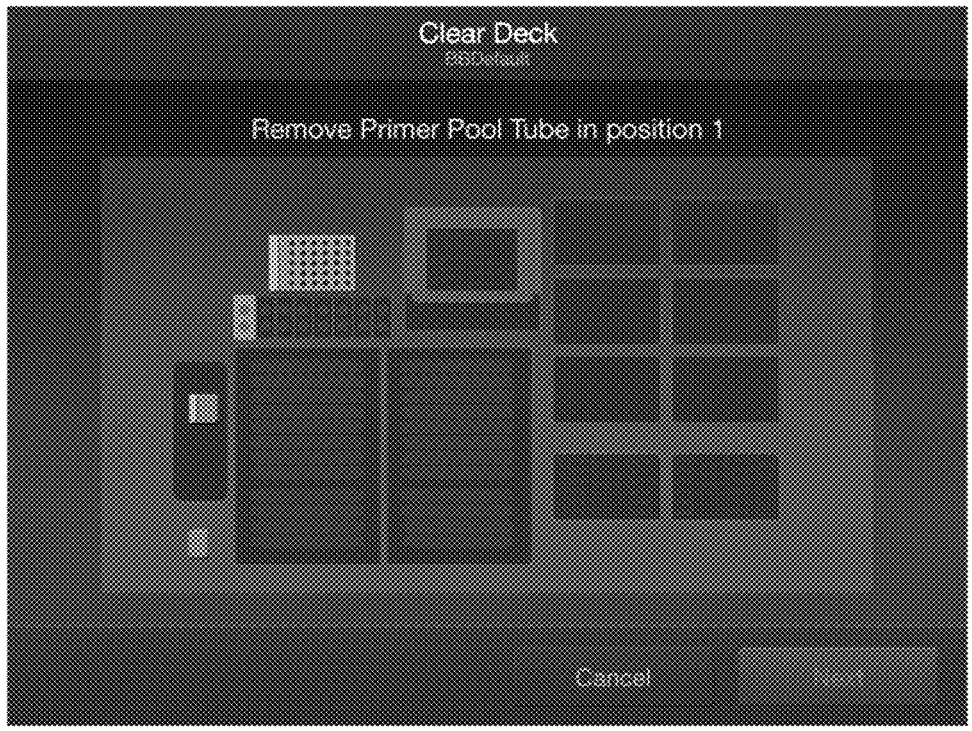
Figure 37:
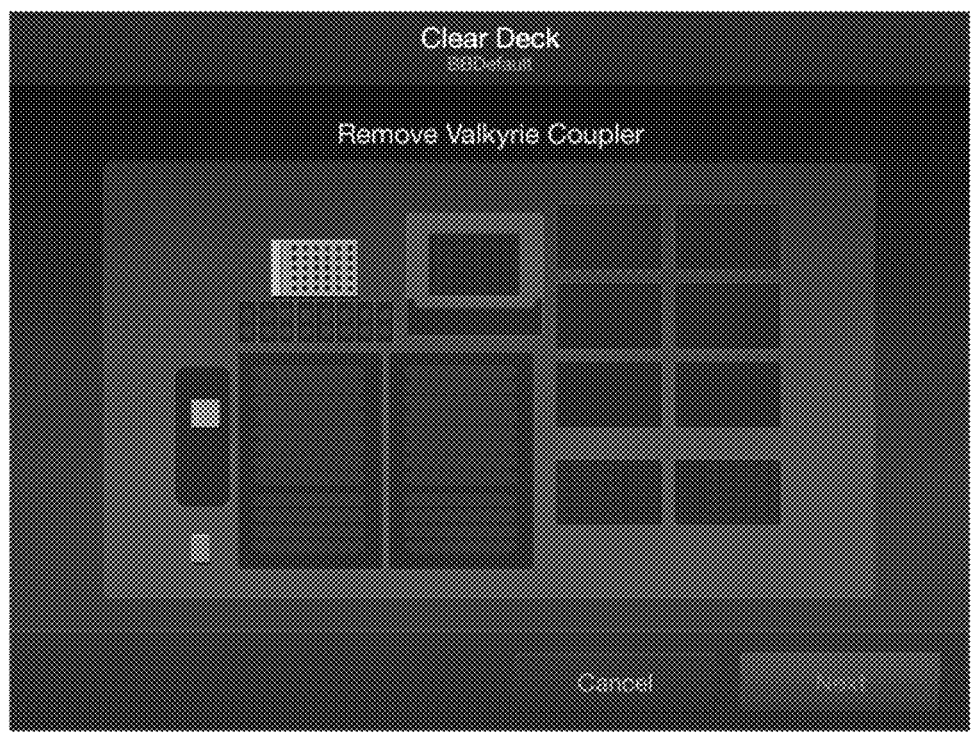
Figure 38:
Figure 39:
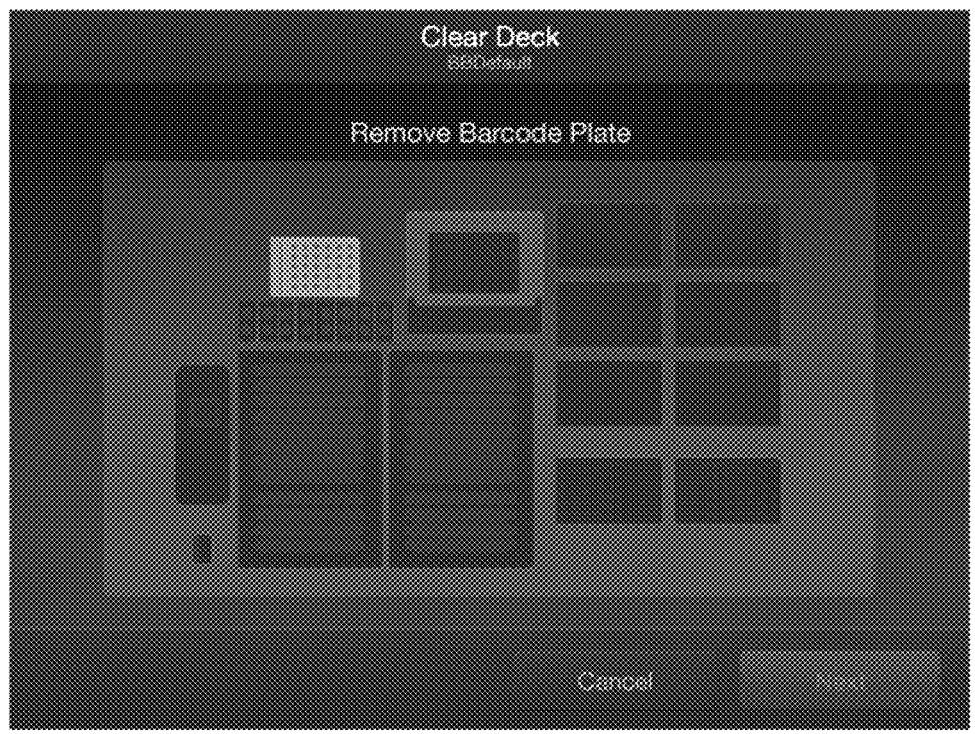
Figure 40:
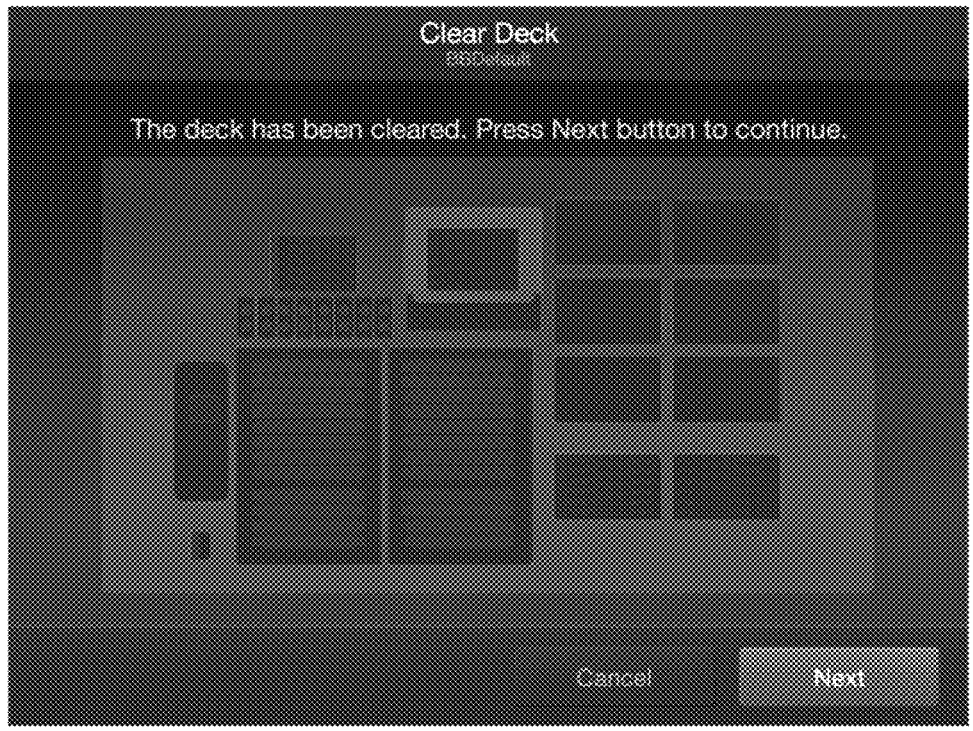

FIG. 26 illustrates an example of a graphical display of the deck of the top section including the top templating section, as shown in FIG. 2. In the event that no used consumables are detected by the vision system, the system indicates that the deck is clear.

In the event that the vision system detects used consumables, FIGS. 27 to 40 illustrate examples of graphical displays and instructions to the user for removing used components of the templating section. Each item to be removed is highlighted in the display for the particular step. Each display screen is displayed automatically in response to a detection of actions by a user or a human error in the procedure.

Figure 41:
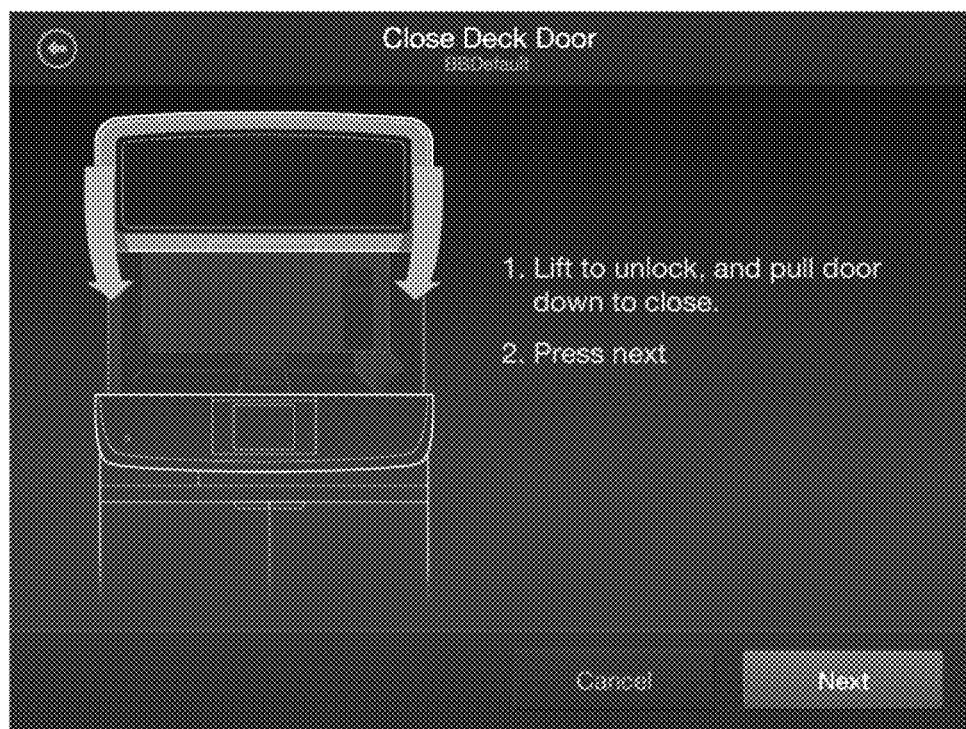
Figure 42:
Figure 43:

FIG. 41 illustrates an example of a graphical display that instructs the user to close the door of the deck. FIGS. 42 and 43 illustrate examples of graphical displays that inform the user about ultraviolet (UV) cleaning of the deck and when cleaning is complete.

Figure 44:
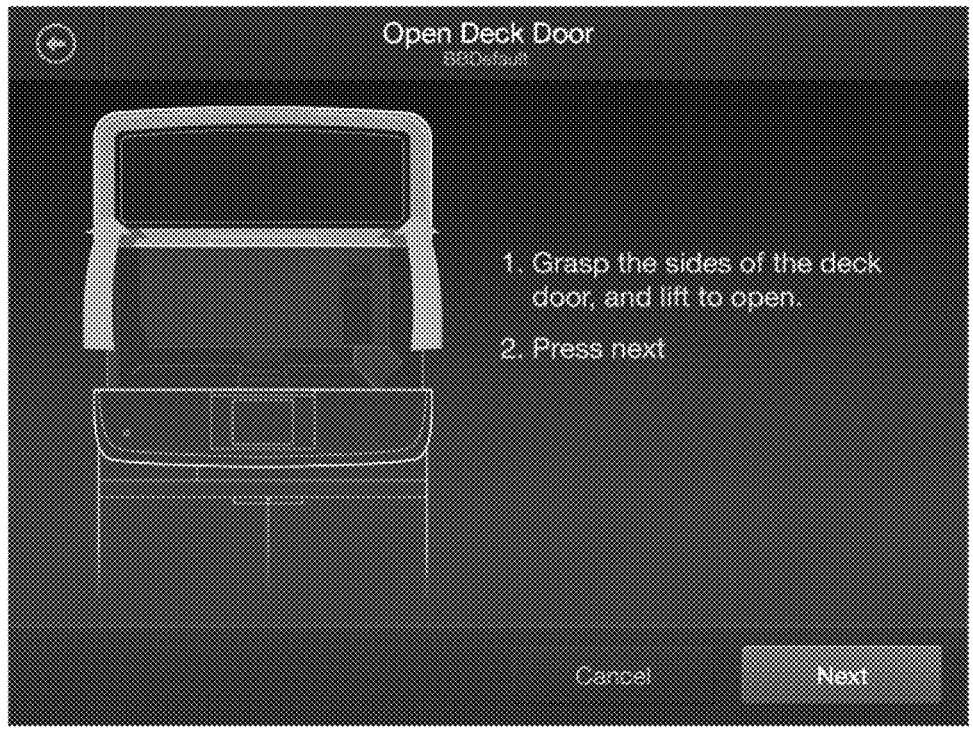
Figure 45:
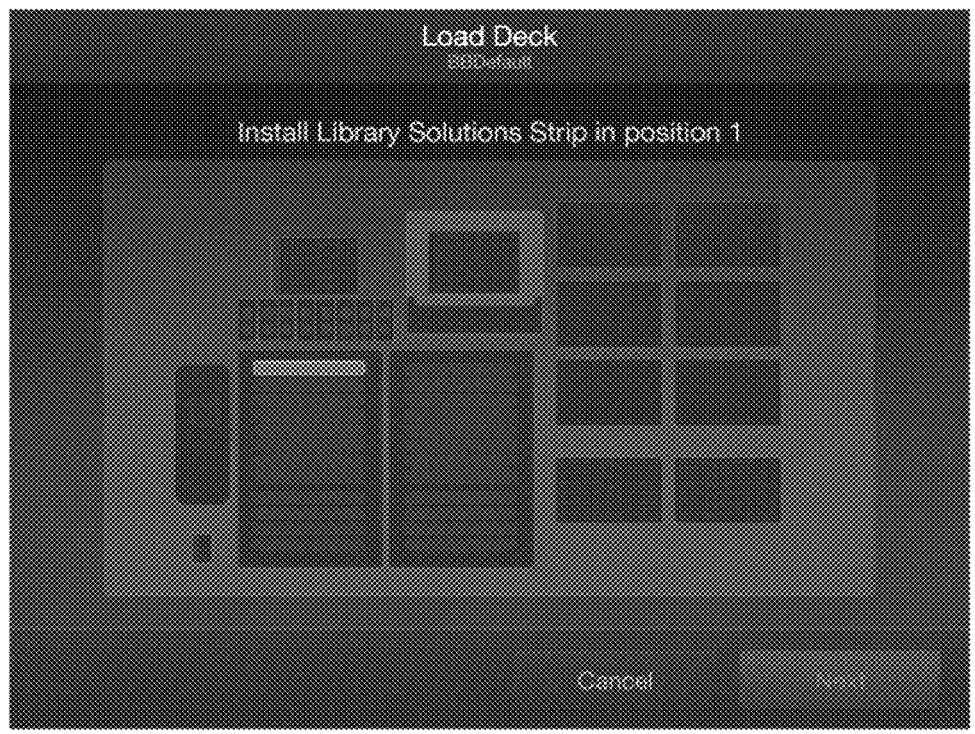
Figure 46:
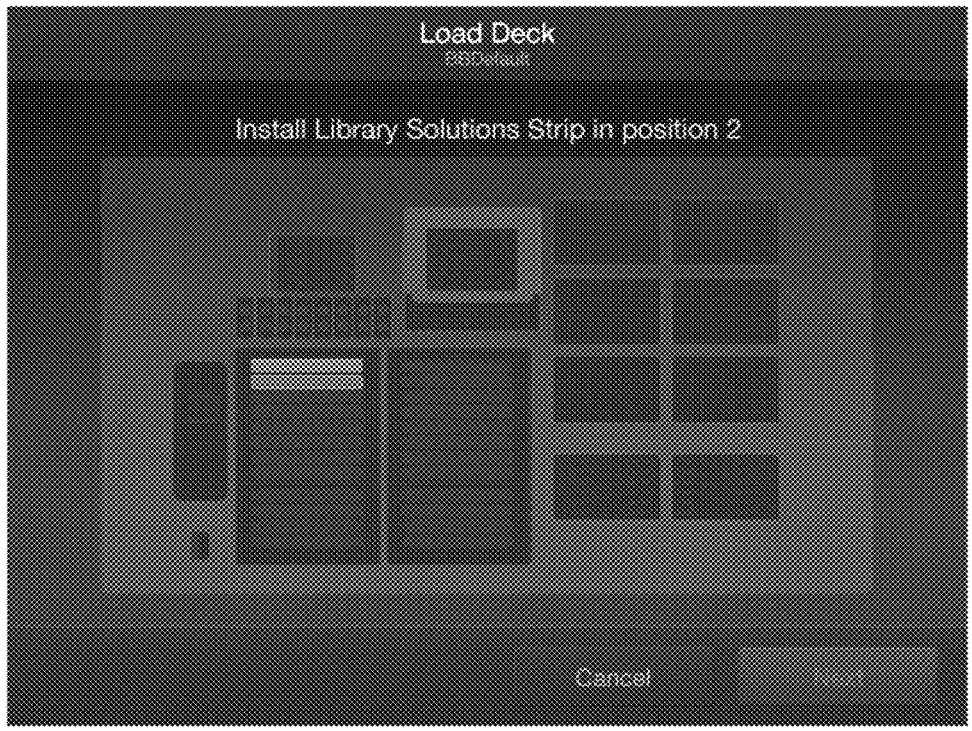
Figure 47:
Figure 48:
Figure 49:
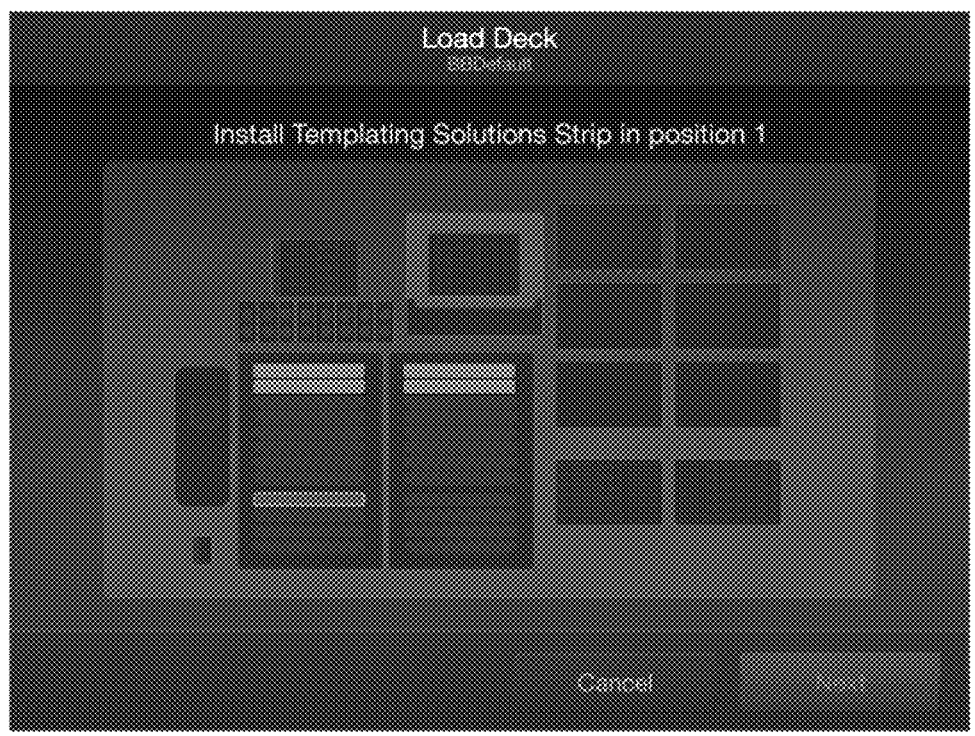
Figure 50:
Figure 51:
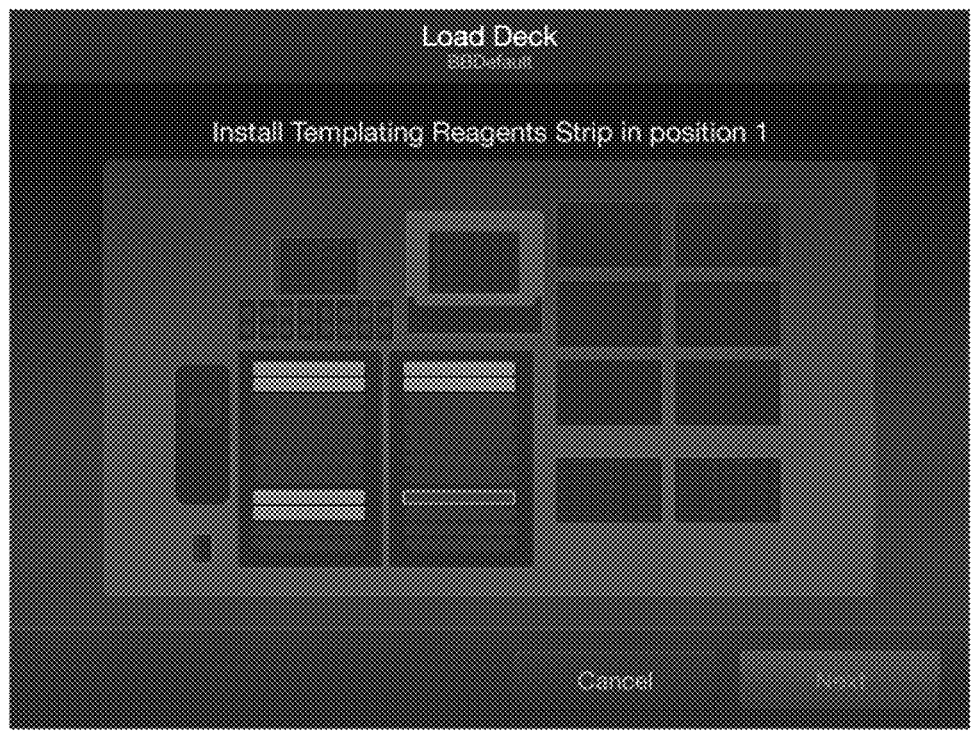
Figure 52:
Figure 53:
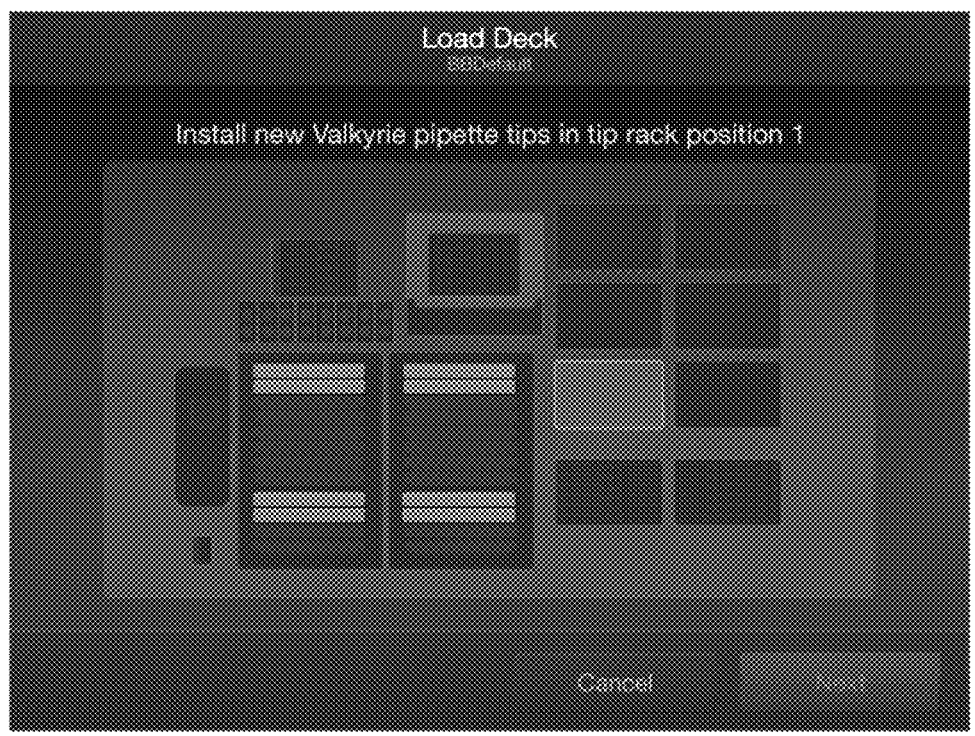
Figure 54:
Figure 55:
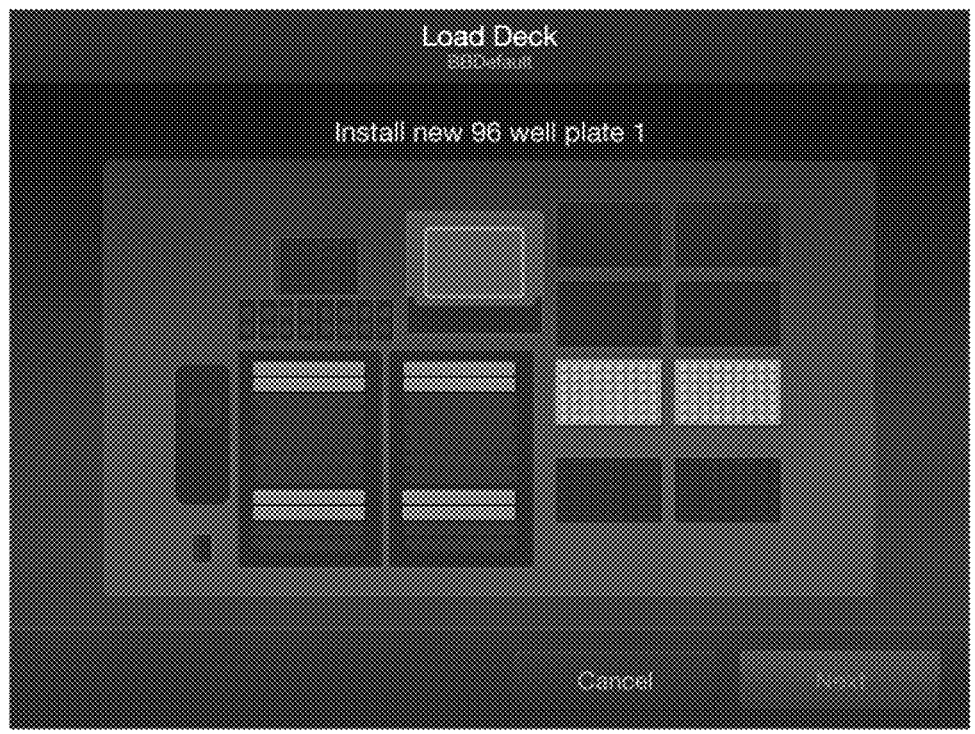
Figure 56:
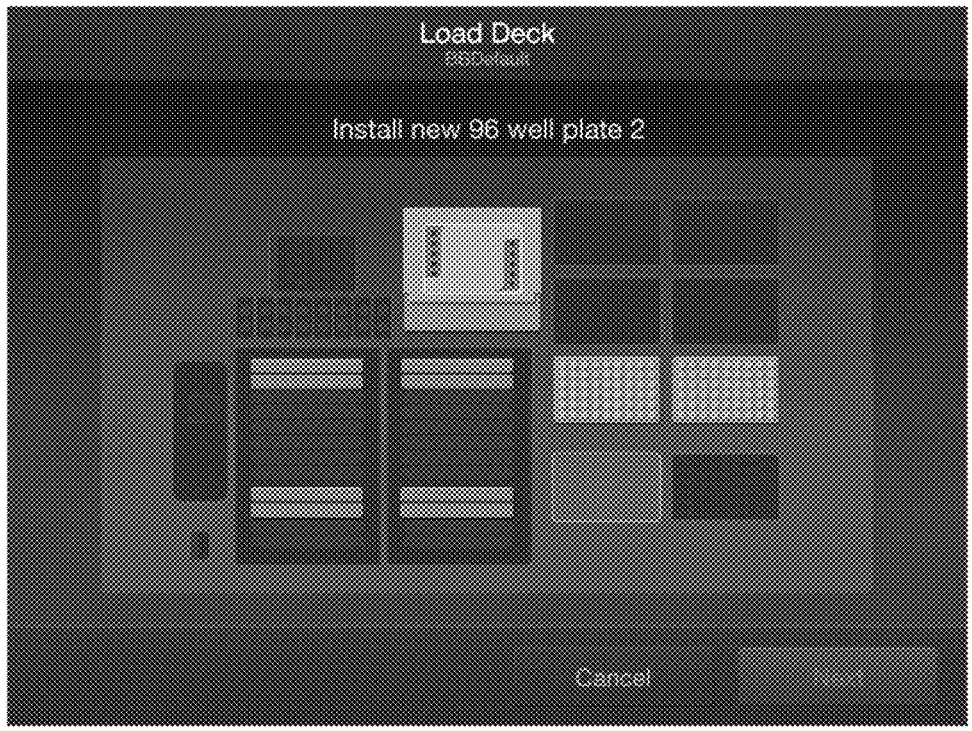
Figure 57:
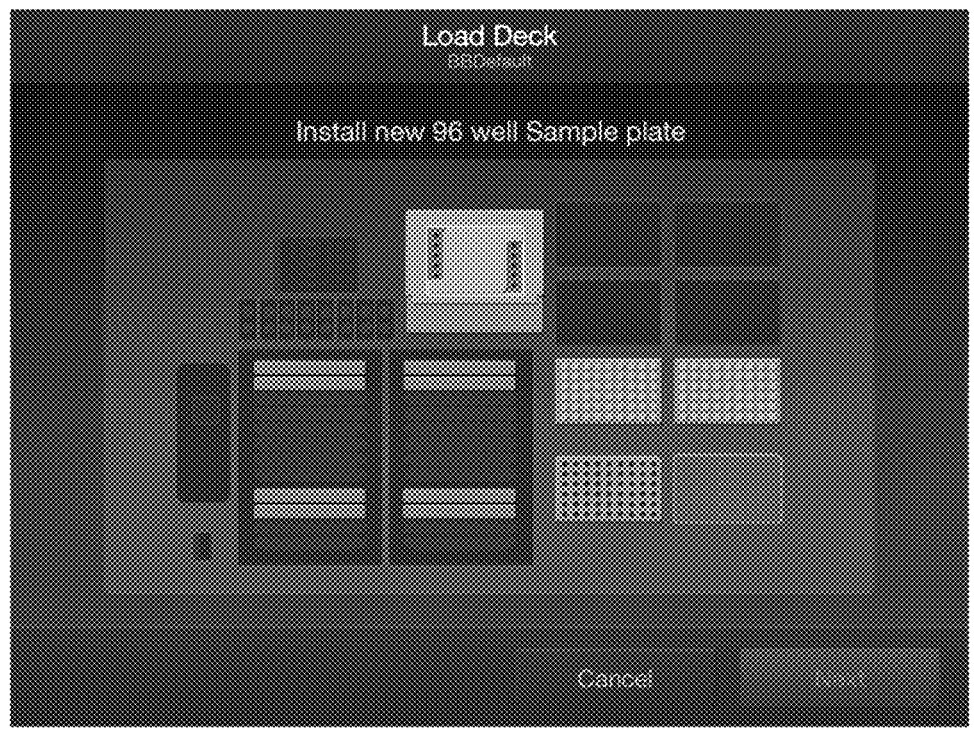
Figure 58:
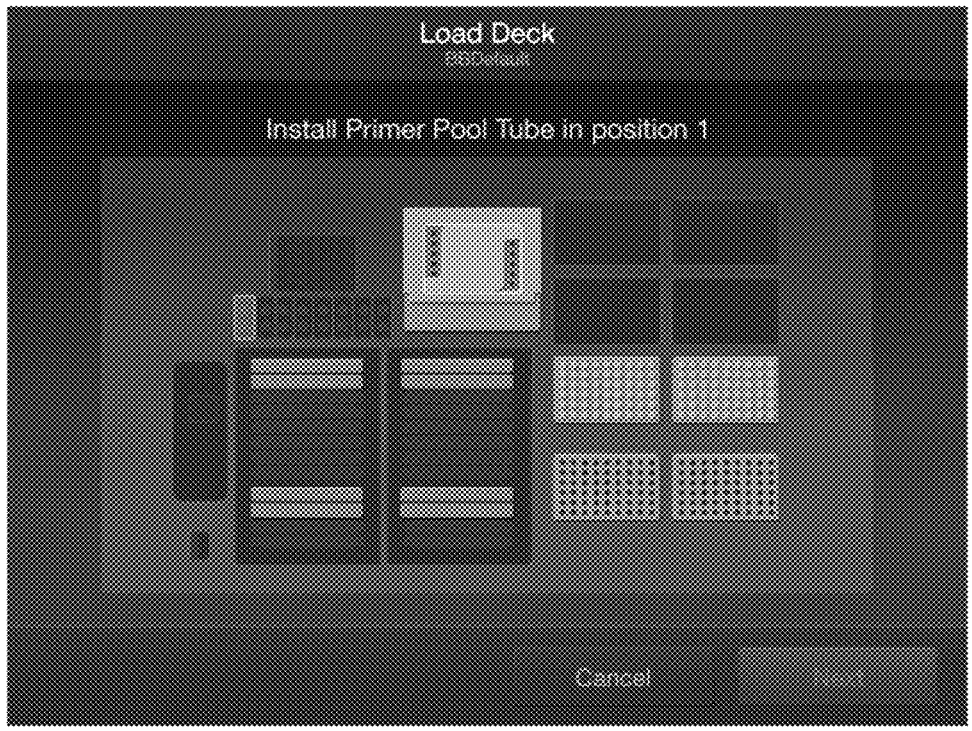
Figure 59:
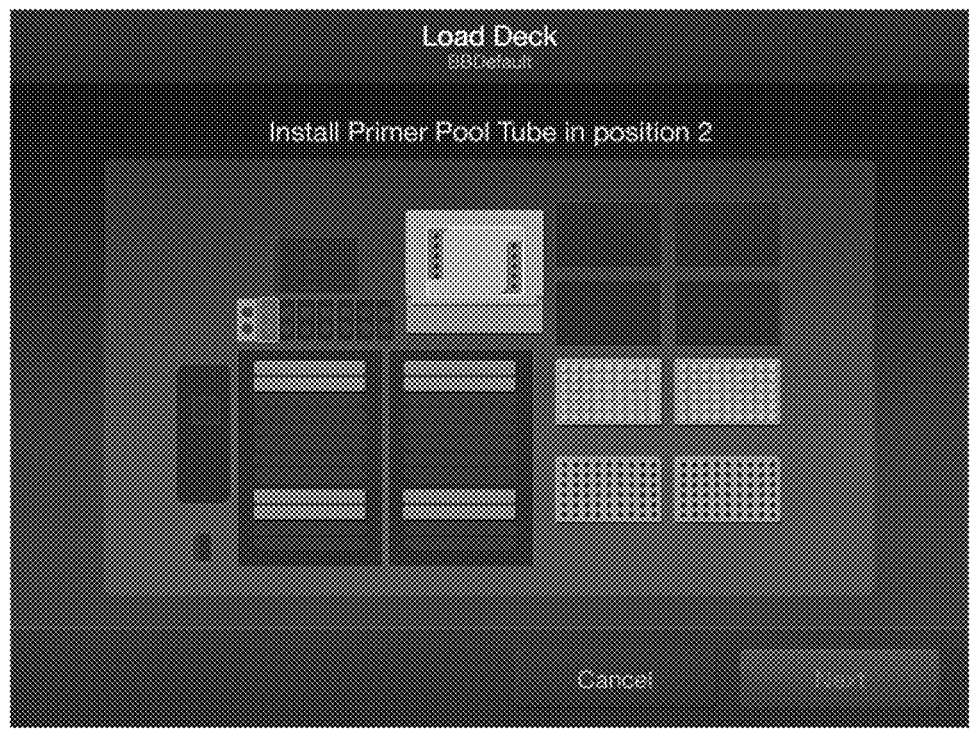
Figure 60:
Figure 61:
Figure 62:
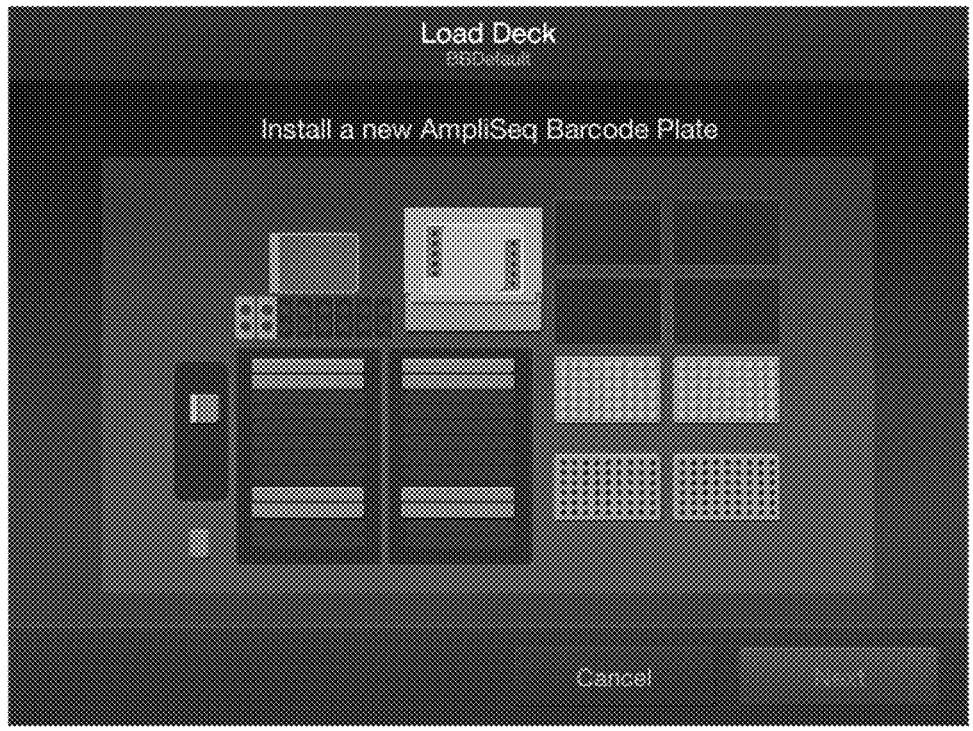

FIG. 44 illustrates an example of a graphical display that instructs the user to open the door of the deck. This begins the series of tasks to prepare the instrument for a new sequencing run.

Figure 63:
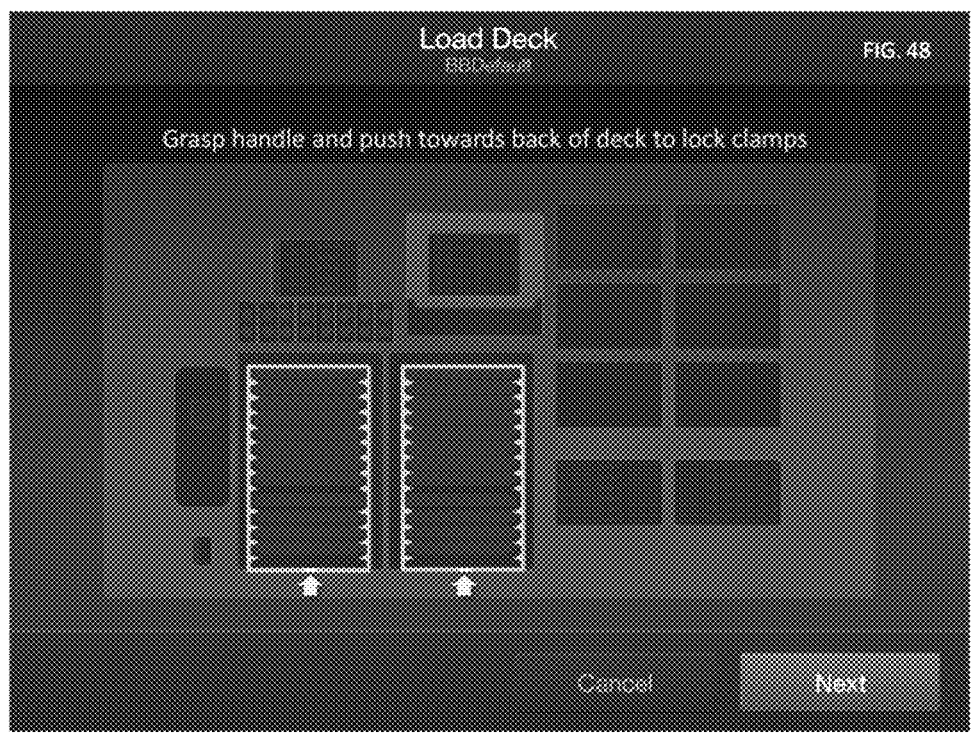

FIGS. 45 to 62 illustrate examples of graphical displays and instructions to the user to install components to the deck. Each item to be installed is highlighted in the display for the particular step. Each display screen is displayed automatically in response to a detection, using the vision system, of actions by a user or a human error in the procedure. FIG. 63 illustrates an interface directing a user to lock a consumable in place. The vision system can detect whether consumables are locked in placed based on detecting a position of the locking mechanisms or associated symbols.

Figure 64:
Figure 65:
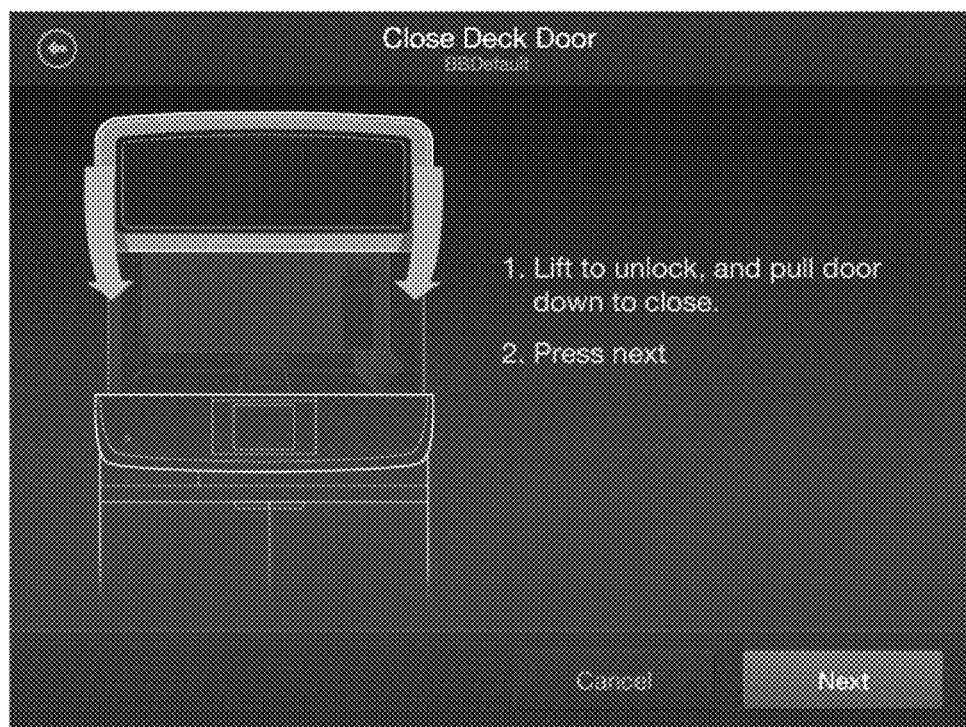

FIG. 64 illustrates an example of a graphical display that indicates to the user that the deck setup is complete. FIG. 65 illustrates an example of a graphical display that instructs the user to close the deck door.

Figure 66:
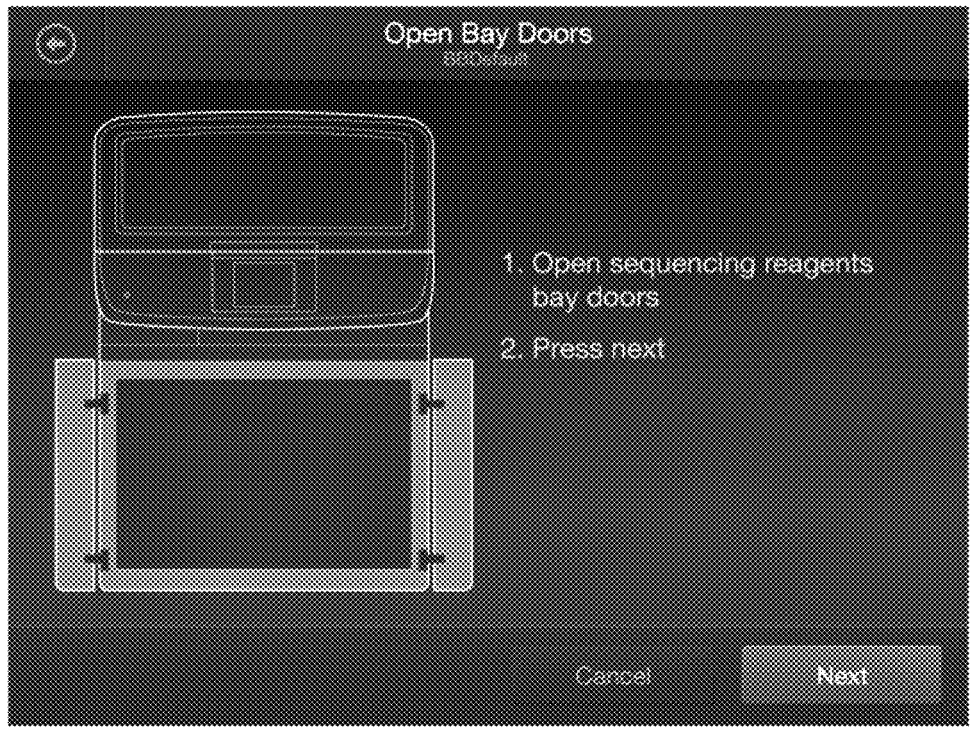
Figure 67:
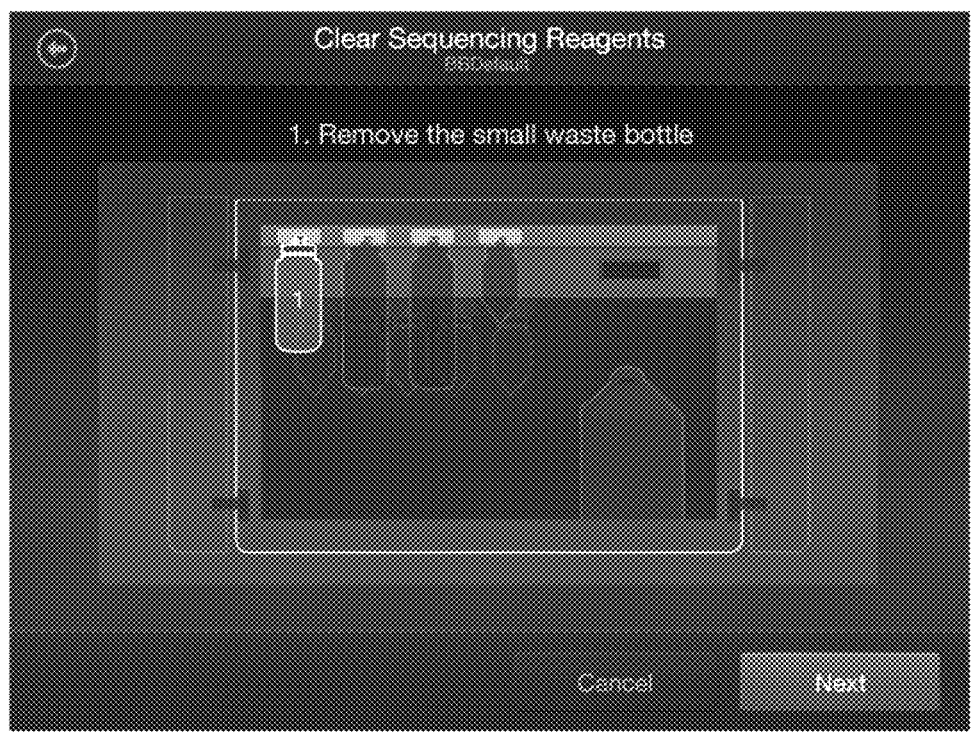
Figure 68:
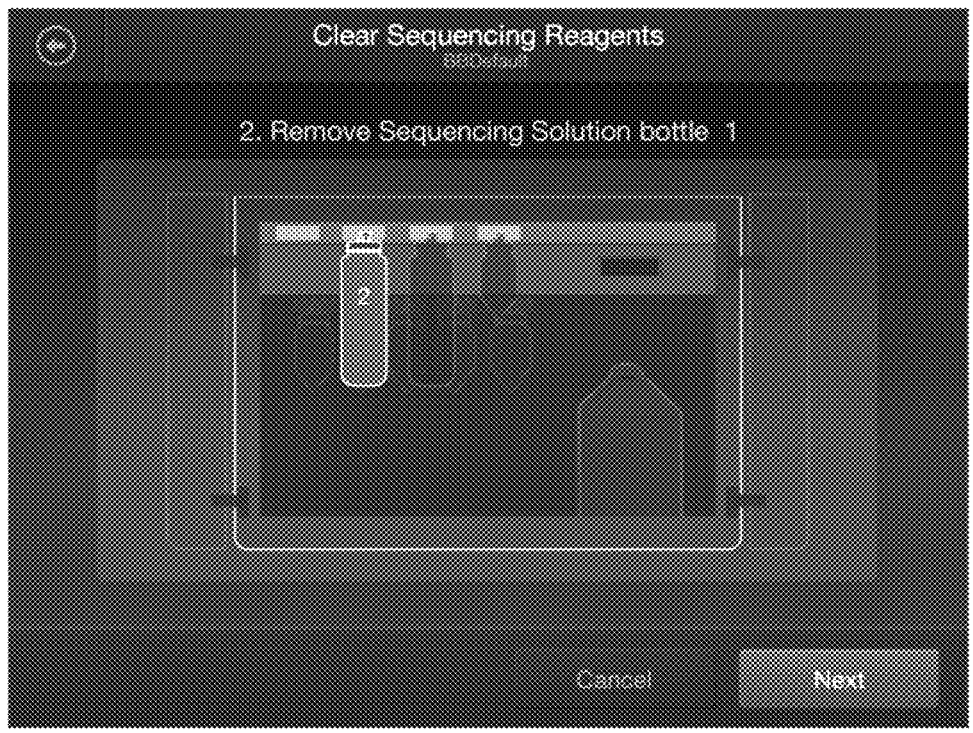
Figure 69:
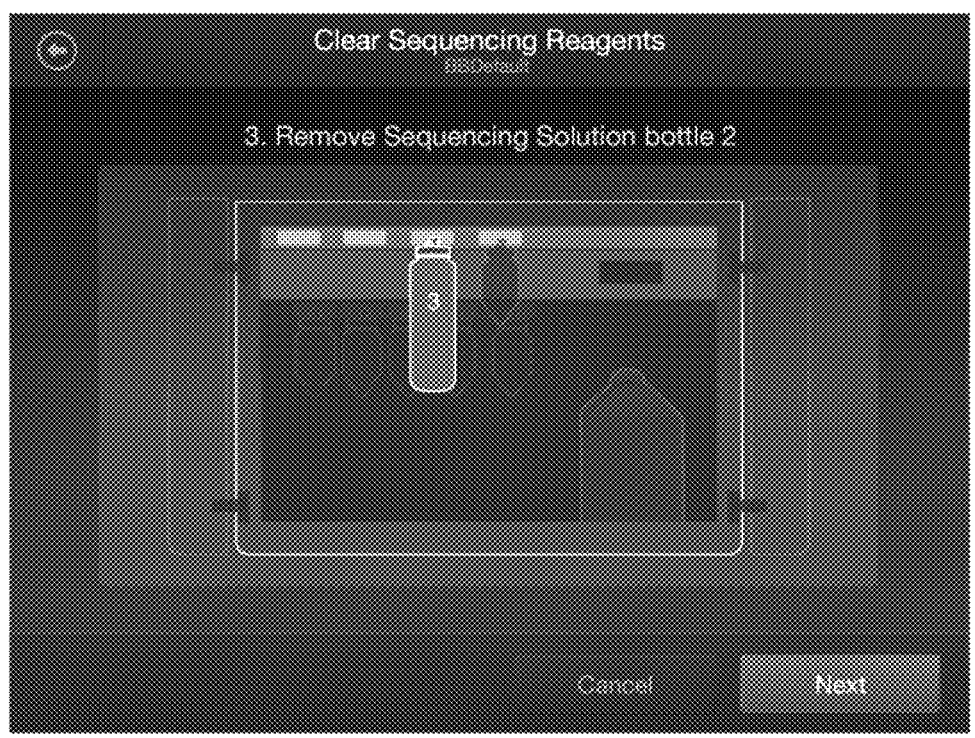
Figure 70:

FIG. 66 illustrates an example of a graphical display that instructs the user to open the sequencing reagent bay doors of the bottom section of the sequencing instrument, as shown in FIG. 3.

FIGS. 67 to 70 illustrate examples of graphical displays and instructions to the user for removing used bottles from the reagent storage bay. Each bottle to be removed is highlighted in the display for the particular step. Each display screen is displayed automatically in response to a detection of actions by a user or a human error in the procedure, for example using an RFID detection or a weight scale.

Figure 71:
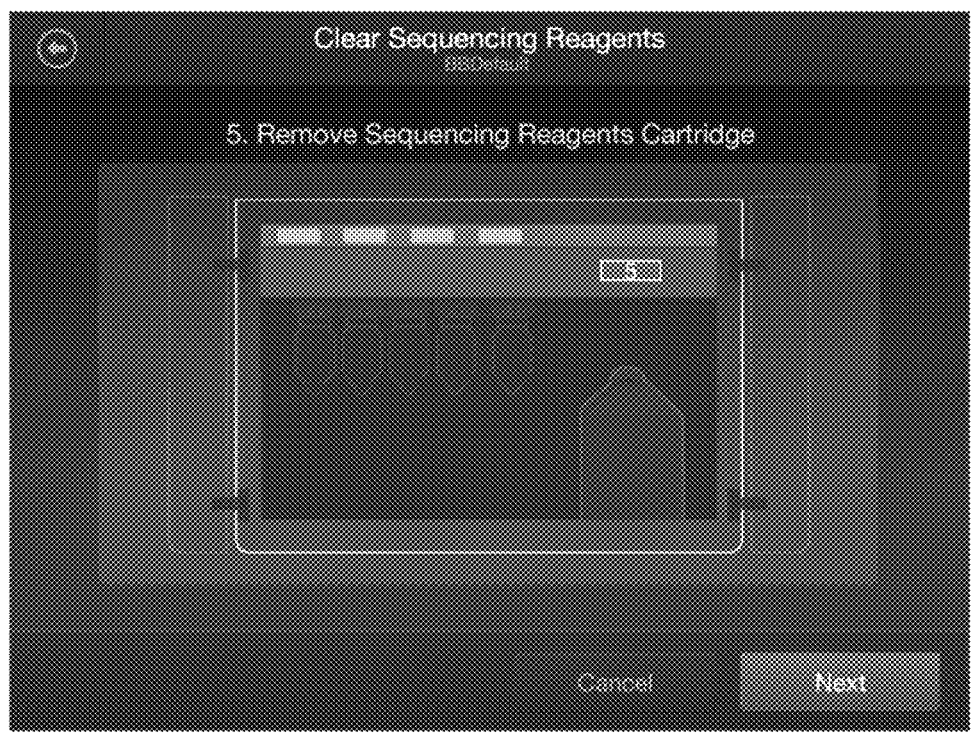

FIG. 71 illustrates an example of a graphical display that instructs the user to remove the used sequencing reagents cartridge, or nucleotide cartridge.

Figure 72:
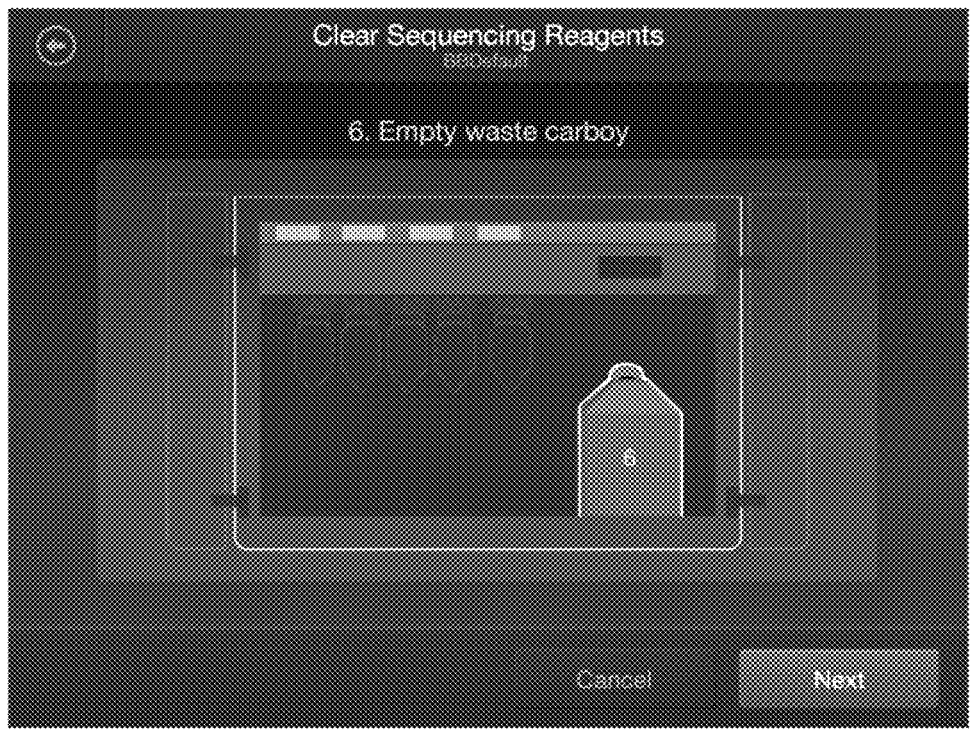
Figure 73:
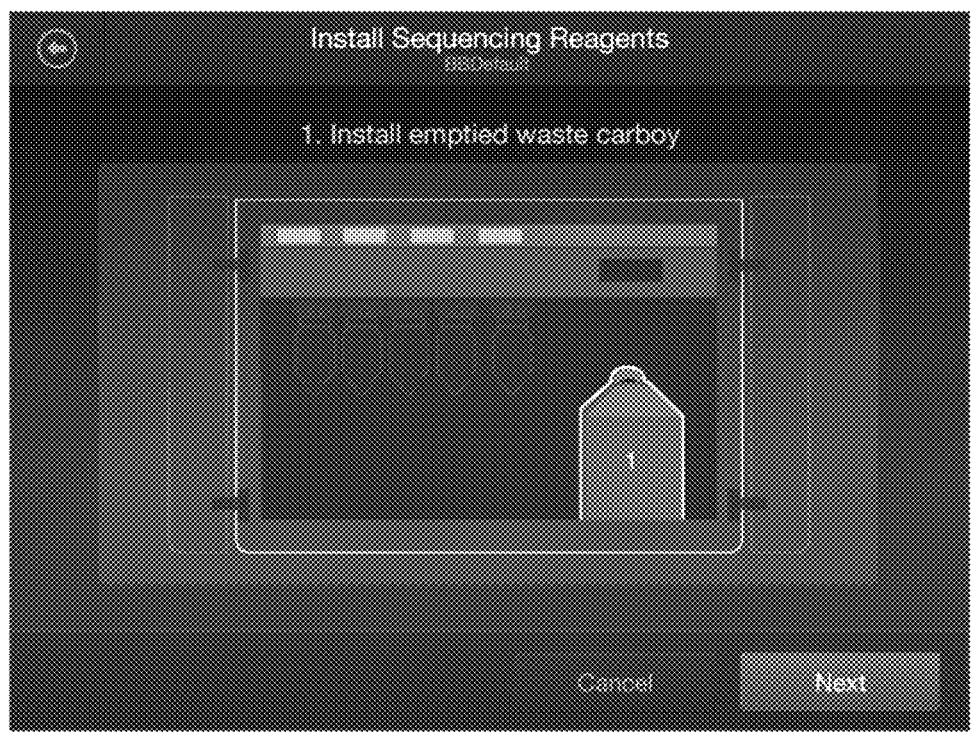
Figure 74:
Figure 75:
Figure 76:
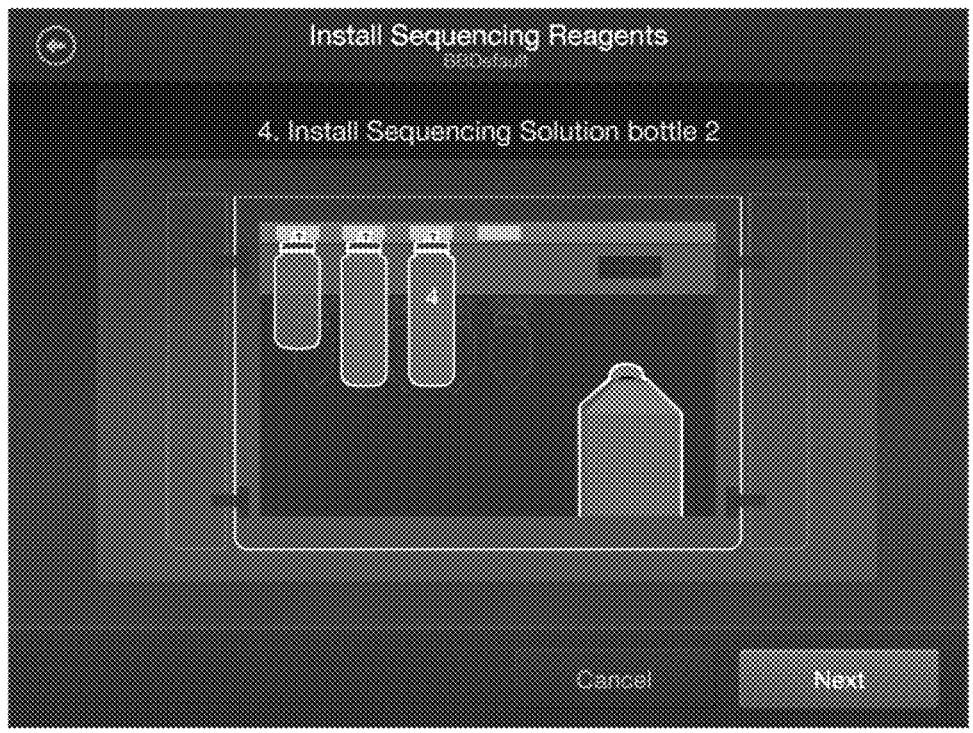
Figure 77:

FIG. 72 illustrates an example of a graphical display that instructs the user to empty the waste carboy located in the reagent bay.

FIGS. 73 to 77 illustrate examples of graphical displays and instructions to the user for installing the waste carboy and new reagent bottles into the reagent bay. Each new item to be installed is highlighted in the display for the particular step. Each display screen is displayed automatically in response to a detection, for example, by RFID, of actions by a user or a human error in the procedure.

Figure 78:
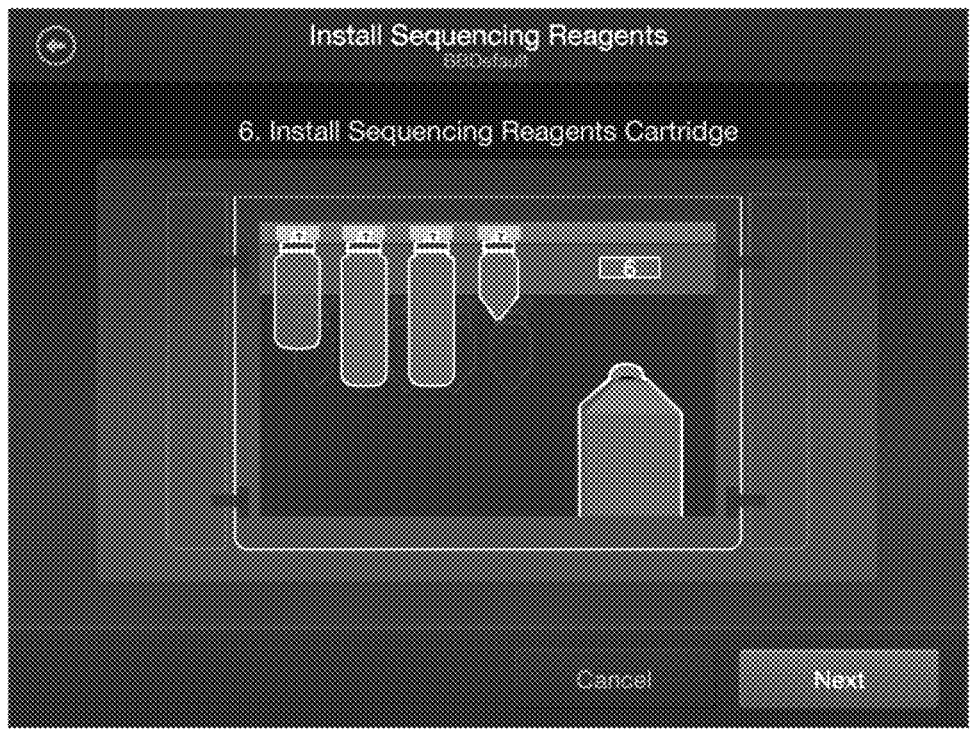

FIG. 78 illustrates an example of a graphical display that instructs the user to install a new sequencing reagents cartridge, or nucleotide cartridge. In some embodiments, the RFID labels on the installed bottles and nucleotide cartridge can be detected to verify that the correct reagents and nucleotide cartridge are present.

Figure 79:

FIG. 79 illustrates an example of a graphical display that informs the user that all reagents have been installed.

Figure 80:
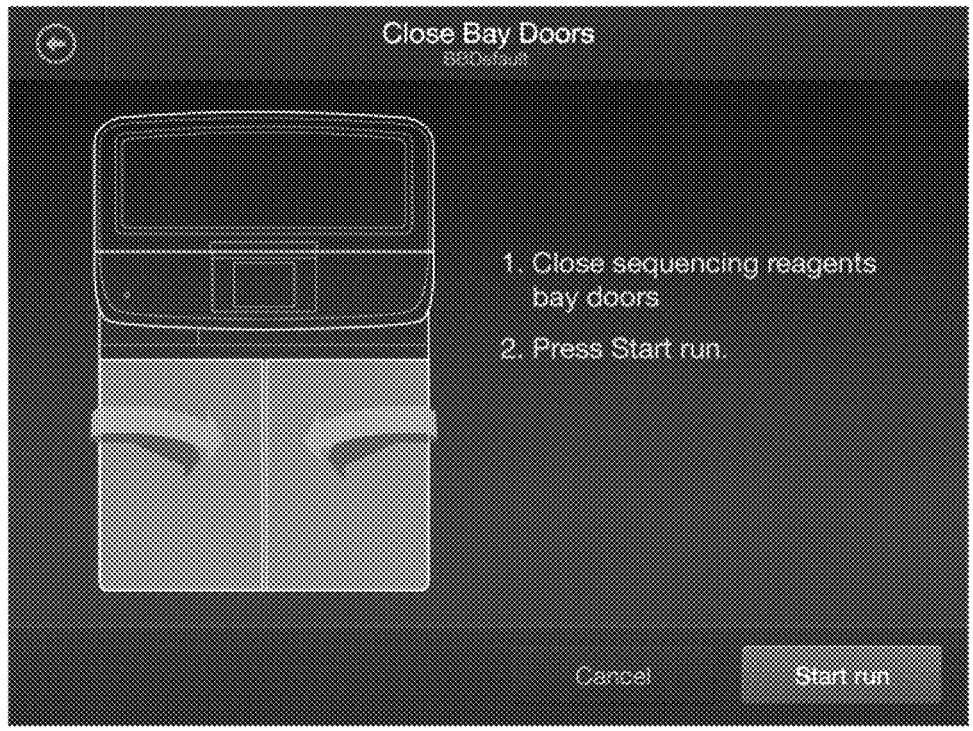

FIG. 80 illustrates an example of a graphical display that instructs the user to close the doors of the reagent bay and press the start run button.

Figure 81:
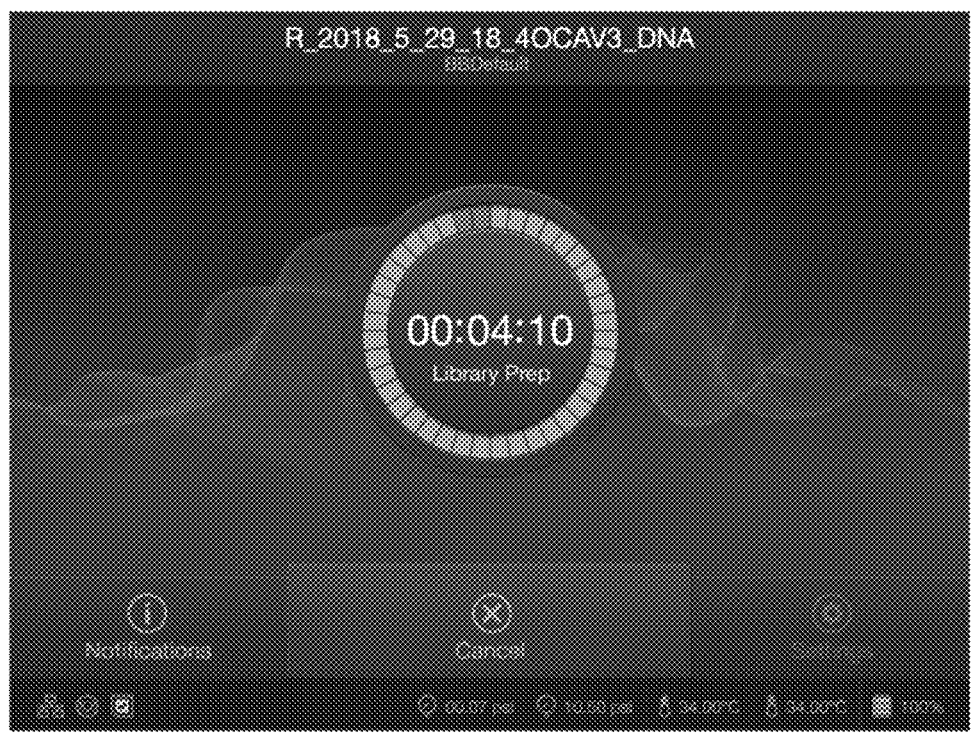
Figure 82:
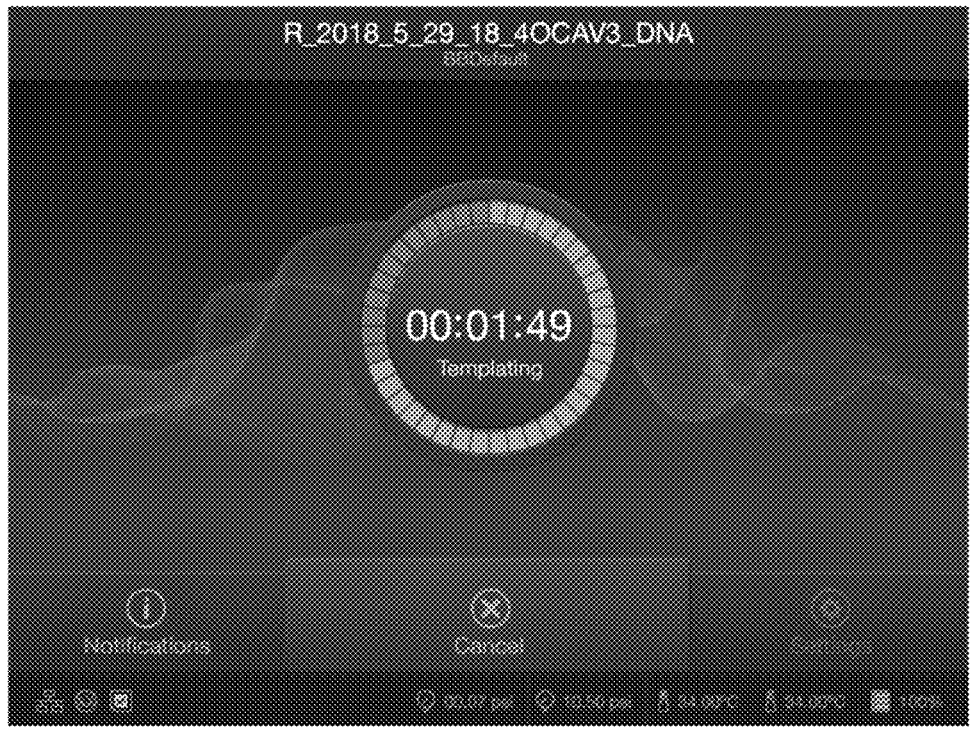
Figure 83:
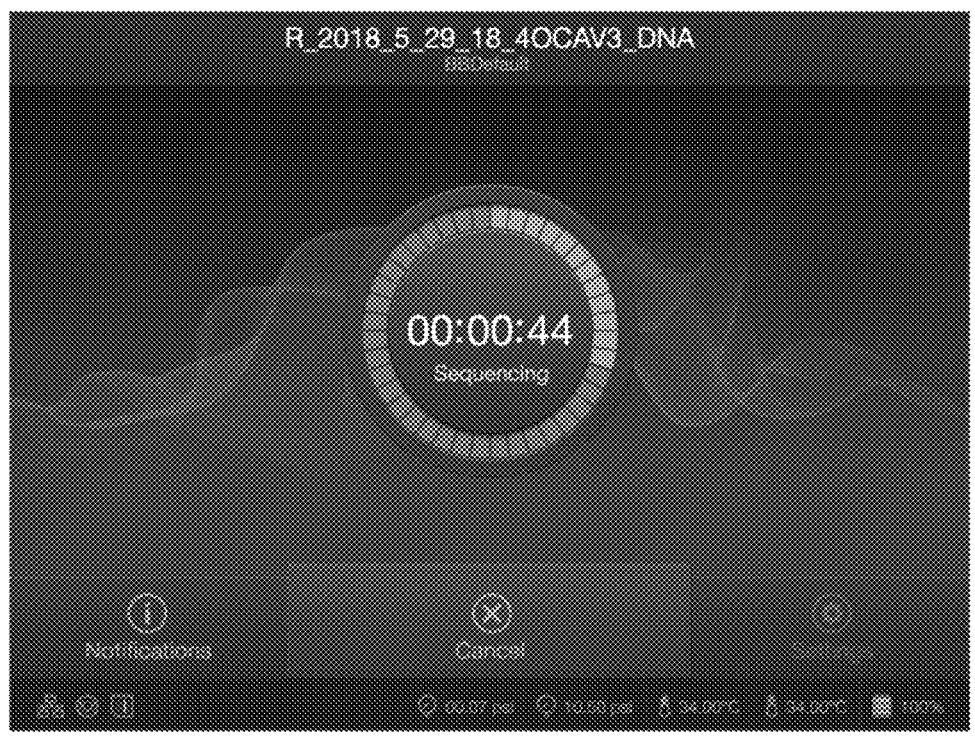
Figure 84:
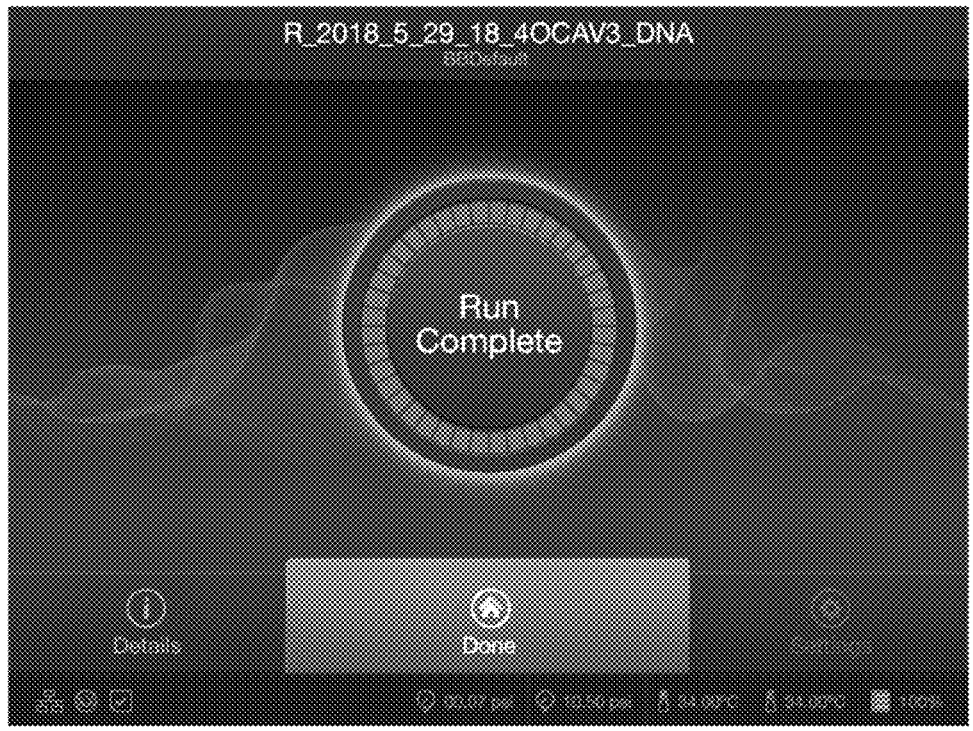

The display can be further used to indicate the progress of various steps of a run plan. For example, FIG. 81 illustrates an example of a graphical display that informs the user of the progress of library prep. FIG. 82 illustrates an example of a graphical display that informs the user of the progress of templating. FIG. 83 illustrates an example of a graphical display that informs the user of the progress of sequencing. Further, FIG. 84 illustrates an example of a graphical display that informs the user that sequencing run is complete.

Figure 85:

In another example, a method for loading and unloading reagent containers or consumables from a system can include monitoring which containers or device consumables are inserted and making suggestions as to which containers and device consumables are to be removed in which order. For example, FIGS. 85-93 illustrate an example method for following the progress of the system loading and unloading using machine vision. As illustrated in FIG. 85, the user interface instructions a user to open the door of the system.

Figure 86:
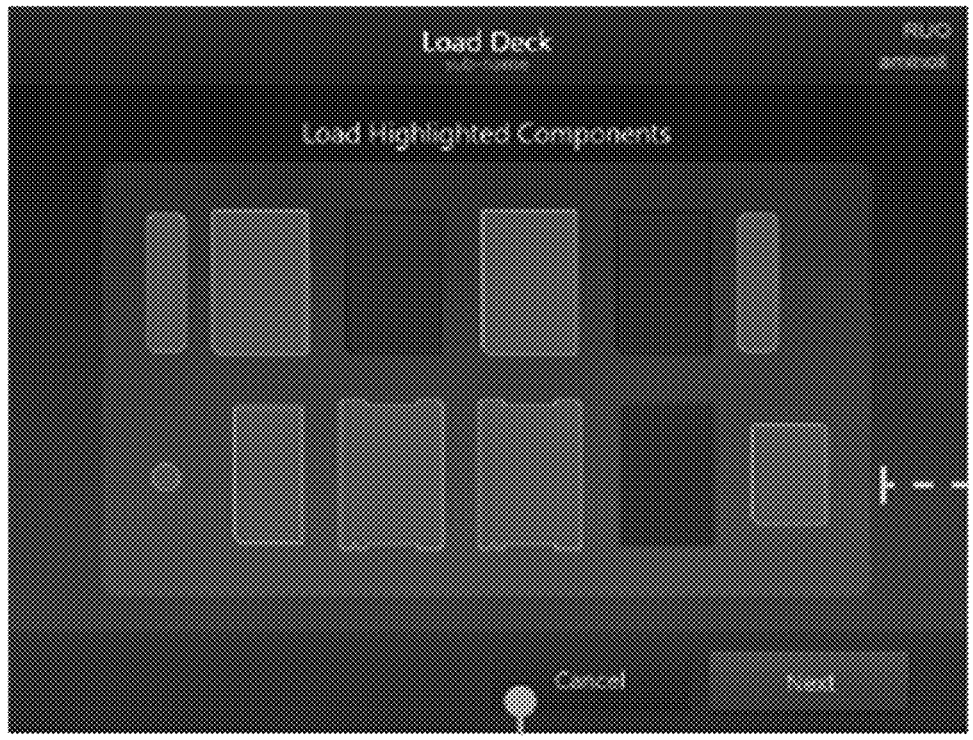
Figure 87:
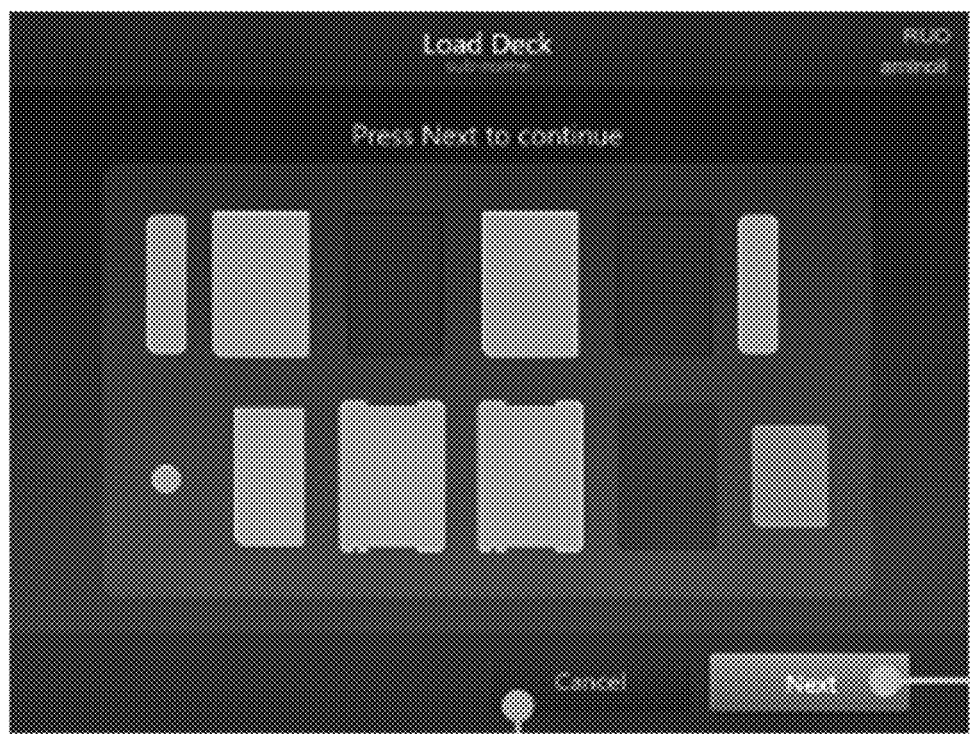

When it is detected that the door is open, the user can be instructed to load components, as illustrated in FIG. 86. For example, the system can highlight components that are to be loaded. As components are loaded, the system can illustrate which components are correctly loaded by changing the color, pattern, or other visual cue to indicate that the appropriate component or container has been loaded into the appropriate location, as illustrated in FIG. 87. In the event that a component is improperly loaded, the system can further indicate improper loading using a color, sound, or other cue to alert the user.

Figure 88:
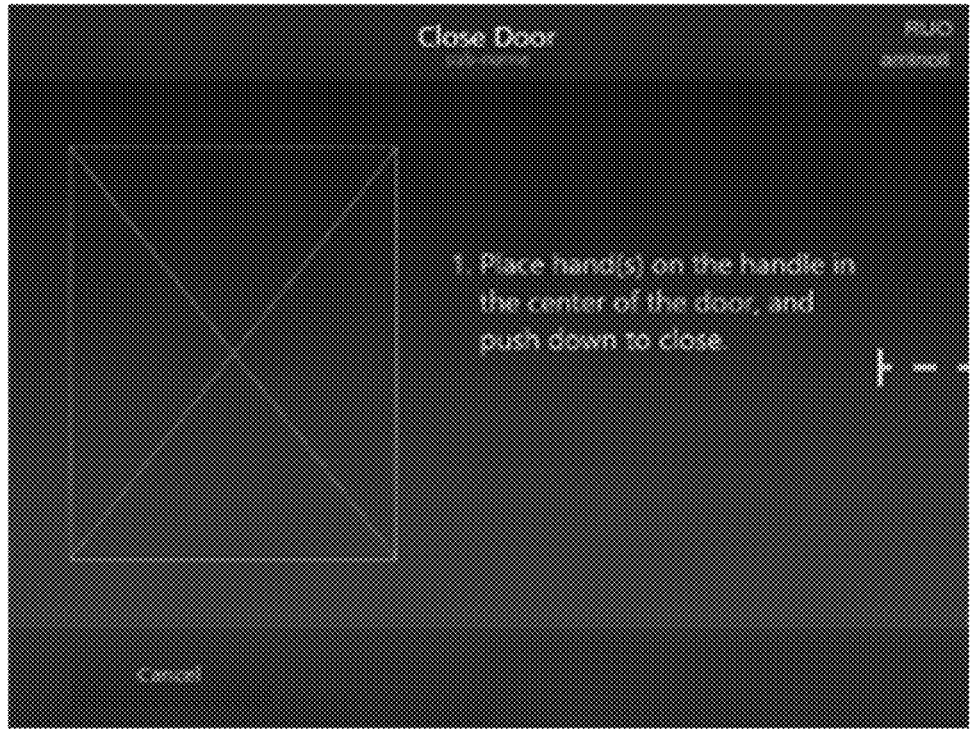

As illustrated in FIG. 88, once the components are properly loaded, the system can instruct the user to close the system door and initiate subsequent operational steps.

Figure 89:
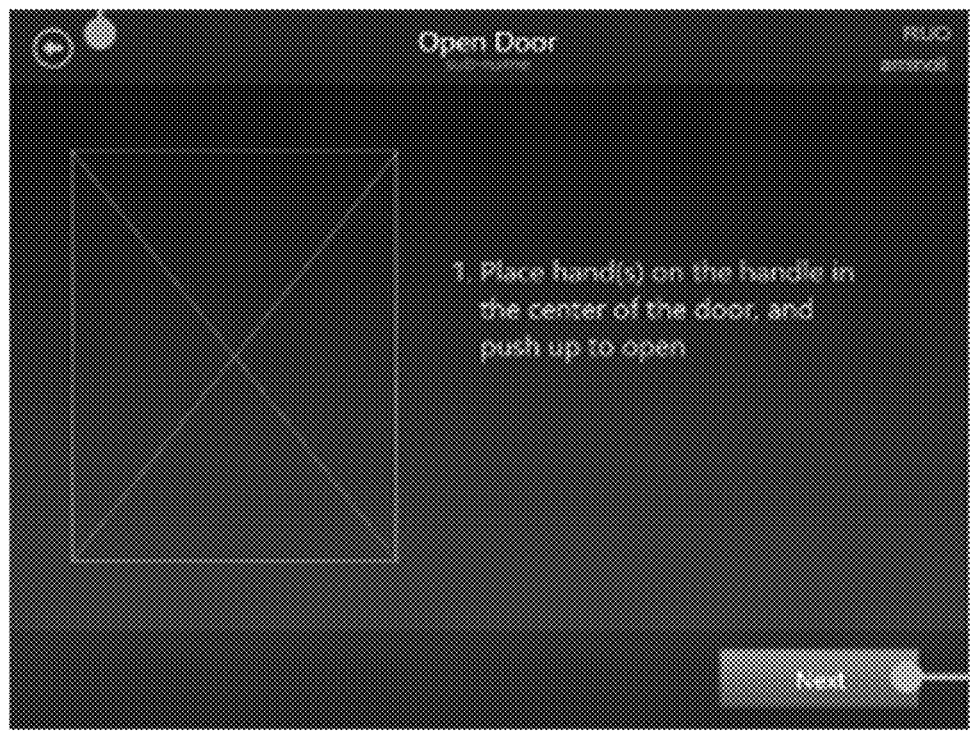
Figure 90:
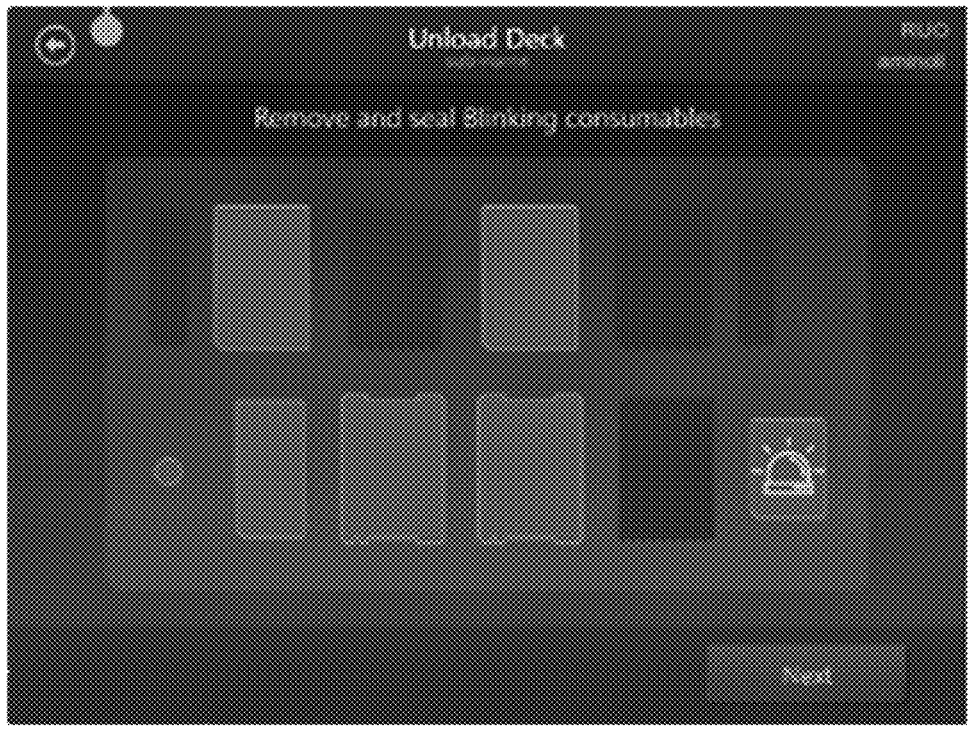

To unload the device once other operational steps have been completed, the system can instruct a user to open the door of the system, as illustrated in FIG. 89. As illustrated at FIG. 90, the system can indicate which containers and consumables to remove first. For example, the system can produce samples that are located in a particular compartment. The system can notify the user to remove those samples first and possibly seal the samples for use in other devices. As illustrated at FIG. 90, a sample to be removed can be highlighted with a particular color, blink, change color, or have an icon indicating that that sample is to be removed first.

Figure 91:
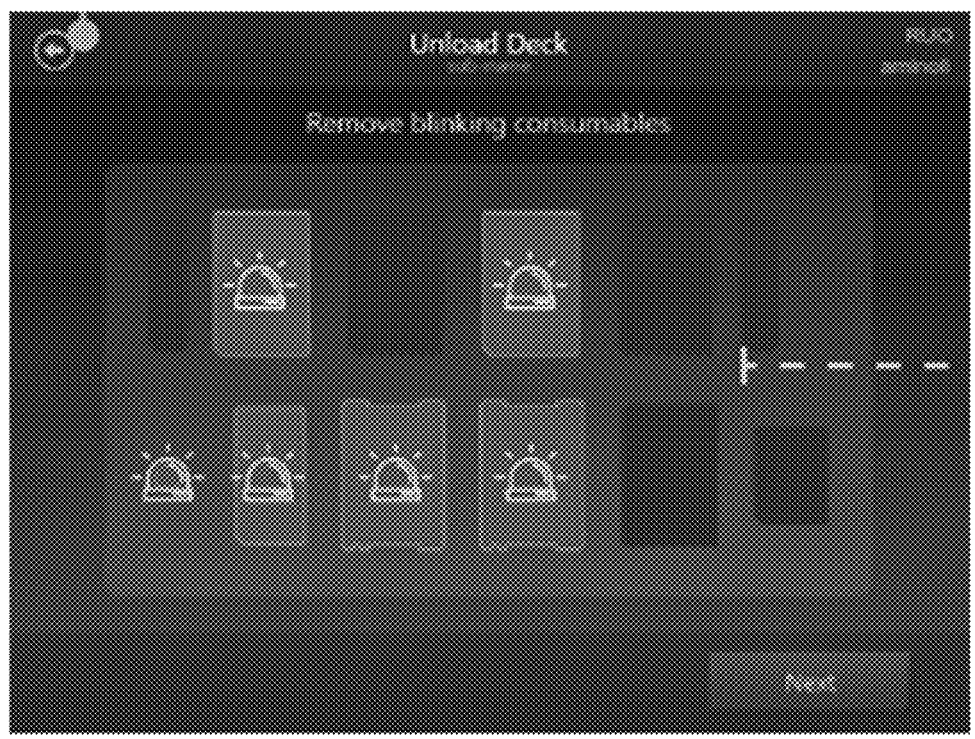

Once the sample is removed, other consumables or containers can be identified for removal, as illustrated at FIG. 91. In an example, flashing or blinking icons can be used indicate which consumables or containers are to be removed. Alternatively, changes in color, sounds, or other indicators can be used indicate which containers are to be removed.

Figure 92:
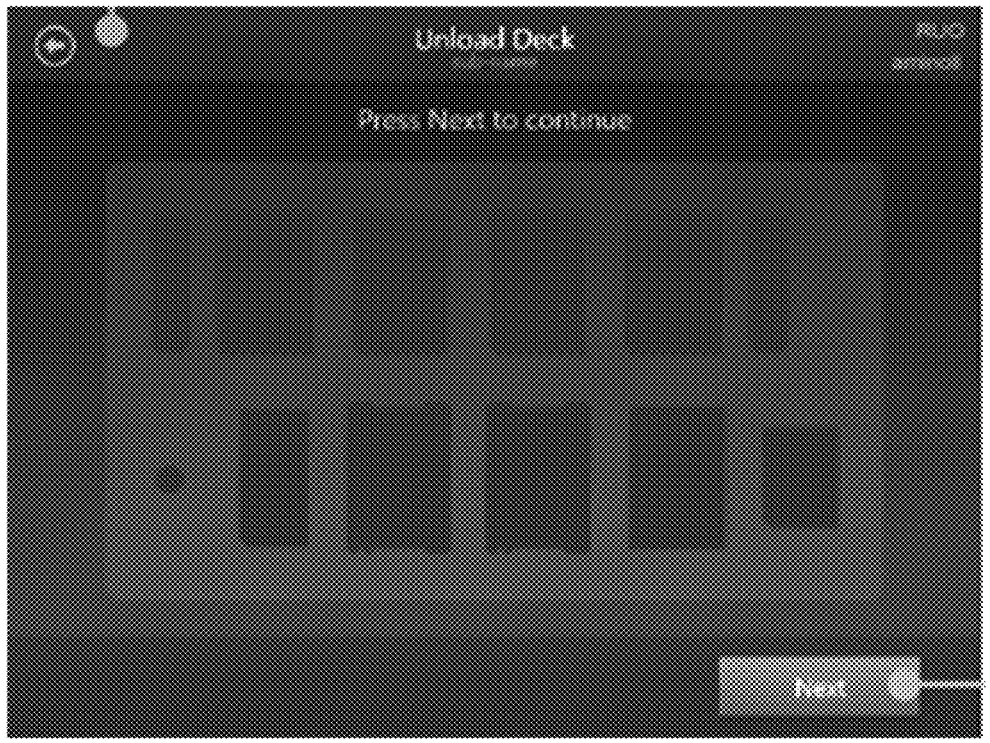

As illustrated at FIG. 92, when the containers or consumables are removed, the spaces graphically associated with the removed consumables can be illustrated as being empty. Once the device is empty, the user can be instructed to close the door, as illustrated at FIG. 93.

Figure 94:
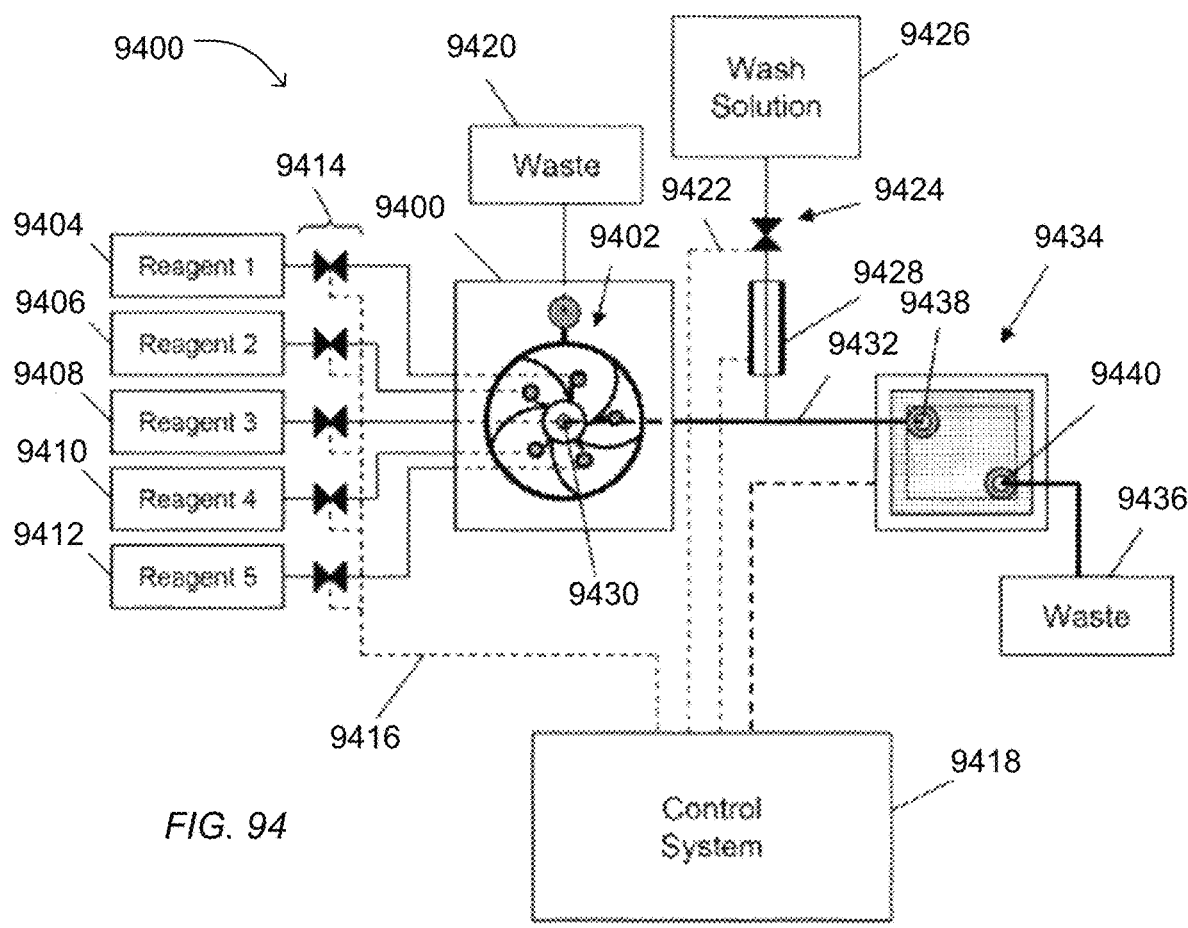
FIG. 94 includes an illustration of an example sequencing system.

The above methods and systems find particular use in initiating a sequencing instrument. An example sequencing instrument includes ion-based sequencing instruments or optical-based sequencing instruments. In a particular example illustrated in FIG. 94, a system 9400 containing fluidics circuit 9402 is connected by inlets to at least two reagent reservoirs (9404, 9406, 9408, 9410, or 9412), to waste reservoir 9420, and to biosensor 9434 by fluid pathway 9432 that connects fluidics node 9430 to inlet 9438 of biosensor 9434 for fluidic communication. Reagents from reservoirs (9404, 9406, 9408, 9410, or 9412) can be driven to fluidic circuit 9402 by a variety of methods including pressure, pumps, such as syringe pumps, gravity feed, and the like, and are selected by control of valves 9414. Reagents from the fluidics circuit 9402 can be driven through the valves 9414 receiving signals from control system 9418 to waste container 9420. Reagents from the fluidics circuit 9402 can also be driven through the biosensor 9434 to the waste container 9436. The control system 9418 includes controllers for valves, which generate signals for opening and closing via electrical connection 9416.

The control system 9418 also includes controllers for other components of the system, such as wash solution valve 9424 connected thereto by electrical connection 9422, and reference electrode 9428. Control system 9418 can also include control and data acquisition functions for biosensor 9434. In one mode of operation, fluidic circuit 9402 delivers a sequence of selected reagents 1, 2, 3, 4, or 5 to biosensor 9434 under programmed control of control system 9418, such that in between selected reagent flows, fluidics circuit 9402 is primed and washed, and biosensor 9434 is washed. Fluids entering biosensor 9434 exit through outlet 9440 and are deposited in waste container 9436 via control of pinch valve regulator 9444. The valve 9444 is in fluidic communication with the sensor fluid output 9440 of the biosensor 9434.

Figure 95:
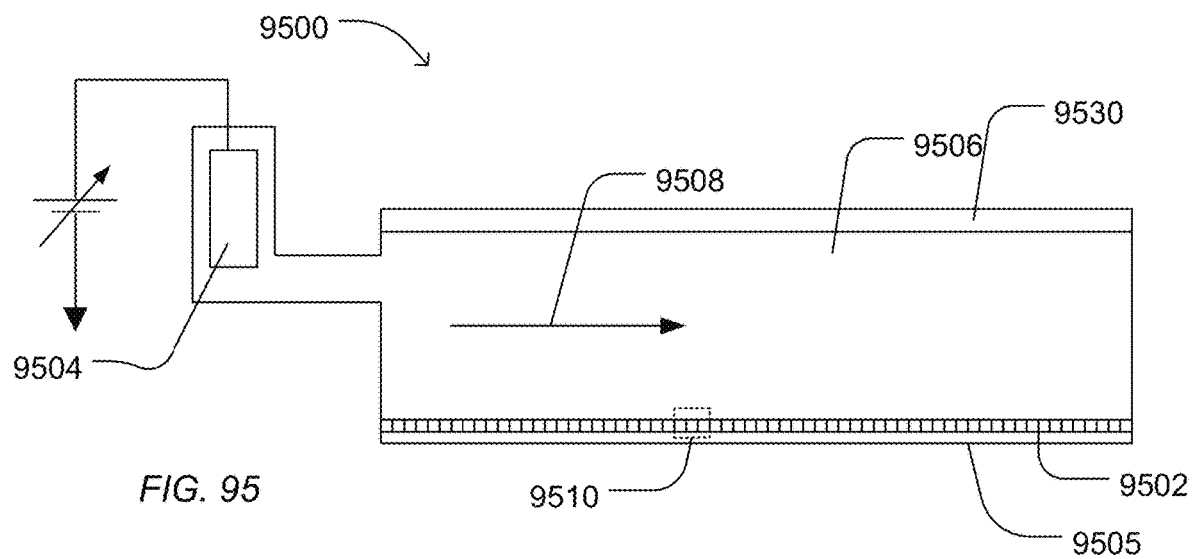
FIG. 95 includes an illustration of an example system including a sensor array.

The device including the dielectric layer defining the well formed from the first access and second access and exposing a sensor pad finds particular use in detecting chemical reactions and byproducts, such as detecting the release of hydrogen ions in response to nucleotide incorporation, useful in genetic sequencing, among other applications. In a particular embodiment, a sequencing system includes a flow cell in which a sensory array is disposed, includes communication circuitry in electronic communication with the sensory array, and includes containers and fluid controls in fluidic communication with the flow cell. In an example, FIG. 95 illustrates an expanded and cross-sectional view of a flow cell 9500 and illustrates a portion of a flow chamber 9506. A reagent flow 9508 flows across a surface of a well array 9502, in which the reagent flow 9508 flows over the open ends of wells of the well array 9502. The well array 9502 and a sensor array 9505 together may form an integrated unit forming a lower wall (or floor) of flow cell 9500. A reference electrode 9504 may be fluidly coupled to flow chamber 9506. Further, a flow cell cover 9530 encapsulates flow chamber 9506 to contain reagent flow 9508 within a confined region.

Figure 96:
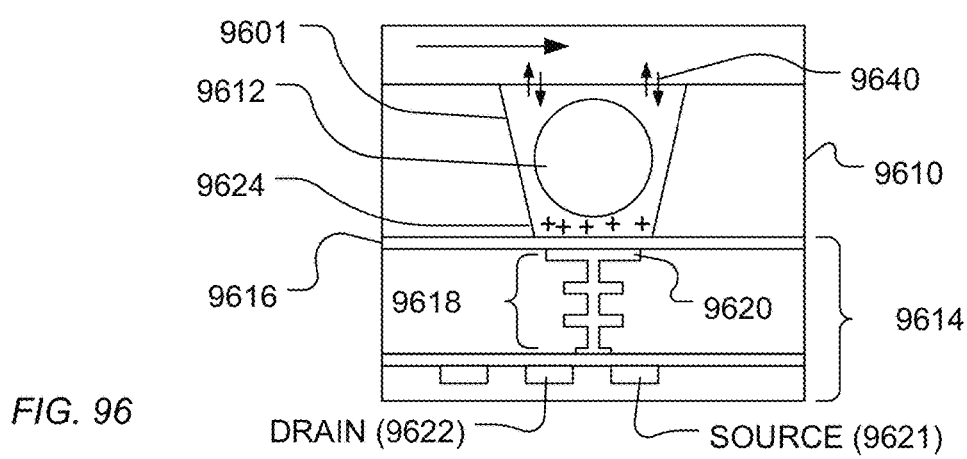
FIG. 96 includes an illustration of an example sensor and associated well.

FIG. 96 illustrates an expanded view of a well 9601 and a sensor 9614, as illustrated at 9510 of FIG. 95. The volume, shape, aspect ratio (such as base width-to-well depth ratio), and other dimensional characteristics of the wells may be selected based on the nature of the reaction taking place, as well as the reagents, byproducts, or labeling techniques (if any) that are employed. The sensor 9614 can be a chemical field-effect transistor (chemFET), more specifically an ion-sensitive FET (ISFET), with a floating gate 9618 having a sensor plate 9620 optionally separated from the well interior by a material layer 9616. The sensor 9614 can be responsive to (and generate an output signal related to) the amount of a charge 9624 present on the material layer 9616 opposite the sensor plate 9620. The material layer 9616 can be a ceramic layer, such as an oxide of zirconium, hafnium, tantalum, aluminum, or titanium, among others, or a nitride of titanium. Alternatively, the material layer 9616 can be formed of a metal, such as titanium, tungsten, gold, silver, platinum, aluminum, copper, or a combination thereof. In an example, the material layer 9616 can have a thickness in a range of 5 nm to 100 nm, such as a range of 10 nm to 70 nm, a range of 15 nm to 65 nm, or even a range of 20 nm to 50 nm.

While the material layer 9616 is illustrated as extending beyond the bounds of the illustrated FET component, the material layer 9616 can extend along the bottom of the well 9601 and optionally along the walls of the well 9601. The sensor 9614 can be responsive to (and generate an output signal related to) the amount of a charge 9624 present on the material layer 9616 opposite the sensor plate 9620. Changes in the charge 9624 can cause changes in a current between a source 9621 and a drain 9622 of the chemFET. In turn, the chemFET can be used directly to provide a current-based output signal or indirectly with additional circuitry to provide a voltage-based output signal. Reactants, wash solutions, and other reagents may move in and out of the wells by a diffusion mechanism 9640.

The well 9601 can be defined by a wall structure, which can be formed of one or more layers of material. In an example, the wall structure can have a thickness extending from the lower surface to the upper surface of the well in a range of 0.01 micrometers to 10 micrometers, such as a range of 0.05 micrometers to 10 micrometers, a range of 0.1 micrometers to 10 micrometers, a range of 0.3 micrometers to 10 micrometers, or a range of 0.5 micrometers to 6 micrometers. In particular, the thickness can be in a range of 0.01 micrometers to 1 micrometer, such as a range of 0.05 micrometers to 0.5 micrometers, or a range of 0.05 micrometers to 0.3 micrometers. The wells 9601 of array 9502 can have a characteristic diameter, defined as the square root of 4 times the cross-sectional area (A) divided by Pi (e.g., sqrt(4*A/π)), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers. In an example, the wells 9601 can have a characteristic diameter of at least 0.01 micrometers. In a further example, the well 9601 can define a volume in a range of 0.05 fL to 10 pL, such as a volume in a range of 0.05 fL to 1 pL, a range of 0.05 fL to 100 fL, a range of 0.05 fL to 10 fL, or even a range of 0.1 fL to 5 fL.

In an embodiment, reactions carried out in the well 9601 can be analytical reactions to identify or determine characteristics or properties of an analyte of interest. Such reactions can generate directly or indirectly byproducts that affect the amount of charge adjacent to the sensor plate 9620. If such byproducts are produced in small amounts or rapidly decay or react with other constituents, then multiple copies of the same analyte may be analyzed in the well 9601 at the same time in order to increase the output signal generated. In an embodiment, multiple copies of an analyte may be attached to a solid phase support 9612, either before or after deposition into the well 9601. The solid phase support 9612 may be microparticles, nanoparticles, beads, solid or porous comprising gels, or the like. For simplicity and ease of explanation, solid phase support 9612 is also referred herein as a particle or bead. For a nucleic acid analyte, multiple, connected copies may be made by rolling circle amplification (RCA), exponential RCA, or like techniques, to produce an amplicon without the need of a solid support.

In particular, the solid phase support, such a bead support, can include copies of polynucleotides. In a particular example illustrated in FIG. 97, polymeric particles can be used as a support for polynucleotides during sequencing techniques. For example, such hydrophilic particles can immobilize a polynucleotide for sequencing using fluorescent sequencing techniques. In another example, the hydrophilic particles can immobilize a plurality of copies of a polynucleotide for sequencing using ion-sensing techniques. Alternatively, the above described treatments can improve polymer matrix bonding to a surface of a sensor array. The polymer matrices can capture analytes, such as polynucleotides for sequencing.

A bead support may be composed of organic polymers such as polystyrene, polyethylene, polypropylene, polyfluoroethylene, polyethyleneoxy, and polyacrylamide, as well as co-polymers and grafts thereof. A support may also be inorganic, such as glass, silica, controlled-pore-glass (CPG), or reverse-phase silica. The configuration of a support may be in the form of beads, spheres, particles, granules, a gel, or a surface. Supports may be porous or non-porous, and may have swelling or non-swelling characteristics. In some embodiments, a support is an Ion Sphere Particle. Example bead supports are disclosed in U.S. Pat. No. 9,243,085, titled "Hydrophilic Polymeric Particles and Methods for Making and Using Same," and in U.S. Pat. No. 9,868,826, titled "Polymer Substrates Formed from Carboxy Functional Acrylamide," each of which is incorporated herein by reference.

In some embodiments, the solid support is a "microparticle," "bead," "microbead," etc., (optionally but not necessarily spherical in shape) having a smallest cross-sectional length (e.g., diameter) of 50 microns or less, preferably 10 microns or less, 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers). In an example, the support is at least 0.1 microns. Microparticles or bead supports may be made of a variety of inorganic or organic materials including, but not limited to, glass (e.g., controlled pore glass), silica, zirconia, cross-linked polystyrene, polyacrylate, polymethylmethacrylate, titanium dioxide, latex, polystyrene, etc. Magnetization can facilitate collection and concentration of the microparticle-attached reagents (e.g., polynucleotides or ligases) after amplification, and can also facilitate additional steps (e.g., washes, reagent removal, etc.). In certain embodiments, a population of microparticles having different shapes sizes or colors is used. The microparticles can optionally be encoded, e.g., with quantum dots such that each microparticle or group of microparticles can be individually or uniquely identified.

Magnetic beads (e.g., Dynabeads from Dynal, Oslo, Norway) can have a size in a range of 1 micron to 100 microns, such as 2 microns to 100 microns. The magnetic beads can be formed of inorganic or organic materials including, but not limited to, glass (e.g., controlled pore glass), silica, zirconia, cross-linked polystyrene, polystyrene, or a combination thereof.

In some embodiments, a bead support is functionalized for attaching a population of first primers. In some embodiments, a bead is any size that can fit into a reaction chamber. For example, one bead can fit in a reaction chamber. In some embodiments, more than one bead fit in a reaction chamber. In some embodiments, the smallest cross-sectional length of a bead (e.g., diameter) is about 50 microns or less, or about 10 microns or less, or about 3 microns or less, approximately 1 micron or less, approximately 0.5 microns or less, e.g., approximately 0.1, 0.2, 0.3, or 0.4 microns, or smaller (e.g., under 1 nanometer, about 1-10 nanometer, about 10-100 nanometers, or about 100-500 nanometers).

In general, the bead support can be treated to include a biomolecule, including nucleosides, nucleotides, nucleic acids (oligonucleotides and polynucleotides), polypeptides, saccharides, polysaccharides, lipids, or derivatives or analogs thereof. For example, a polymeric particle can bind or attach to a biomolecule. A terminal end or any internal portion of a biomolecule can bind or attach to a polymeric particle. A polymeric particle can bind or attach to a biomolecule using linking chemistries. A linking chemistry includes covalent or non-covalent bonds, including an ionic bond, hydrogen bond, affinity bond, dipole-dipole bond, van der Waals bond, and hydrophobic bond. A linking chemistry includes affinity between binding partners, for example between: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement.

Figure 97:
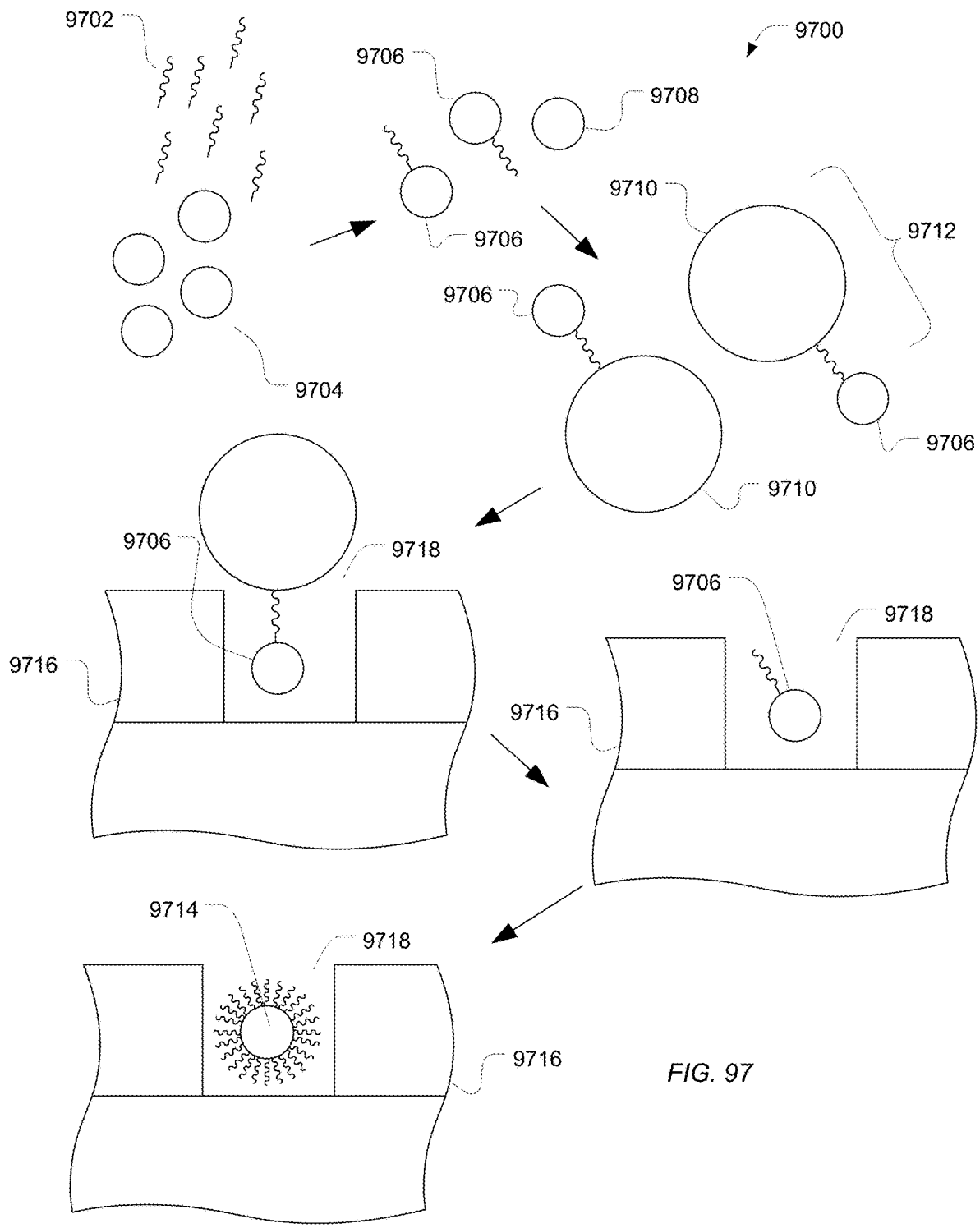
FIG. 97 includes an illustration of an example method for preparing a sequencing device.

As illustrated in FIG. 97, a plurality of bead supports 9704 can be placed in a solution along with a plurality of polynucleotides 9702 (target or template poylnucleotides). The plurality of bead supports 9704 can be activated or otherwise prepared to bind with the polynucleotides 9702. For example, the bead supports 9704 can include an oligonucleotide (capture primer) complementary to a portion of a polynucleotide of the plurality of polynucleotides 9702. In another example, the bead supports 9704 can be modified with target polynucleotides 9702 using techniques such as biotin-streptavidin binding.

In some embodiments, the template nucleic acid molecules (template polynucleotides or target polynucleotides) can be derived from a sample that can be from a natural or non-natural source. The nucleic acid molecules in the sample can be derived from a living organism or a cell. Any nucleic acid molecule can be used, for example, the sample can include genomic DNA covering a portion of or an entire genome, mRNA, or miRNA from the living organism or cell. In other embodiments, the template nucleic acid molecules can be synthetic or recombinant. In some embodiments, the sample contains nucleic acid molecules having substantially identical sequences or having a mixture of different sequences. Illustrative embodiments are typically performed using nucleic acid molecules that were generated within and by a living cell. Such nucleic acid molecules are typically isolated directly from a natural source such as a cell or a bodily fluid without any in vitro amplification. Accordingly, the sample nucleic acid molecules are used directly in subsequent steps. In some embodiments, the nucleic acid molecules in the sample can include two or more nucleic acid molecules with different sequences.

The methods can optionally include a target enrichment step before, during, or after the library preparation and before a pre-seeding reaction. Target nucleic acid molecules, including target loci or regions of interest, can be enriched, for example, through multiplex nucleic acid amplification or hybridization. A variety of methods can be used to perform multiplex nucleic acid amplification to generate amplicons, such as multiplex PCR, and can be used in an embodiment. Enrichment by any method can be followed by a universal amplification reaction before the template nucleic acid molecules are added to a pre-seeding reaction mixture. Any of the embodiments of the present teachings can include enriching a plurality of at least 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 400, 500, 600, 700, 800, 900, 1,000, 2,000, 3,000, 4,000, 5,000, 6,000, 7,000, 8,000, 9,000, or 10,000 target nucleic acid molecules, target loci, or regions of interest. In any of the disclosed embodiments, the target loci or regions of interest can be at least 1, 2, 3, 4, 5, 6, 7, 8, 9, 10, 11, 12, 13, 14, 15, 16, 17, 18, 19, 20, 25, 50, 75, 100, 125, 150, 200, 250, 300, 400, 500, 600, 700, 800, 900, or 1,000 nucleotides in length and include a portion of or the entirety of the template nucleic acid molecule. In other embodiments, the target loci or regions of interest can be between about 1 and 10,000 nucleotides in length, for example between about 2 and 5,000 nucleotides, between about 2 and 3,000 nucleotides, or between about 2 and 2,000 nucleotides in length. In any of the embodiments of the present teachings, the multiplex nucleic acid amplification can include generating at least 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 250, 300, 400, 500, 600, 700, 800, 900, 1,000, 2,000, 3,000, 4,000, 5,000, 6,000, 7,000, 8,000, 9,000, or 10,000 copies of each target nucleic acid molecule, target locus, or region of interest.

In some embodiments, after the library preparation and optional enrichment step, the library of template nucleic acid molecules can be templated onto one or more supports. The one or more supports can be templated in two reactions, a seeding reaction to generate pre-seeded solid supports and a templating reaction using the one or more pre-seeded supports to further amplify the attached template nucleic acid molecules. The pre-seeding reaction is typically an amplification reaction and can be performed using a variety of methods. For example, the pre-seeding reaction can be performed in an RPA reaction, a template walking reaction, or a PCR. In an RPA reaction, template nucleic acid molecules are amplified using a recombinase, polymerase, and optionally a recombinase accessory protein in the presence of primers and nucleotides. The recombinase and optionally the recombinase accessory protein can dissociate at least a portion of a double stranded template nucleic acid molecules to allow primers to hybridize that the polymerase can then bind to initiate replication. In some embodiments, the recombinase accessory protein can be a single-stranded binding protein (SSB) that prevents the re-hybridization of dissociated template nucleic acid molecules. Typically, RPA reactions can be performed at isothermal temperatures. In a template walking reaction, template nucleic acid molecules are amplified using a polymerase in the presence of primers and nucleotides in reaction conditions that allow at least a portion of double-stranded template nucleic acid molecules to dissociate such that primers can hybridize and the polymerase can then bind to initiate replication. In PCR, the double-stranded template nucleic acid molecules are dissociated by thermal cycling. After cooling, primers bind to complementary sequences and can be used for replication by the polymerase. In any of the aspects of the present teachings, the pre-seeding reaction can be performed in a pre-seeding reaction mixture, which is formed with the components necessary for amplification of the template nucleic acid molecules. In any of the disclosed aspects, the pre-seeding reaction mixture can include some or all of the following: a population of template nucleic acid molecules, a polymerase, one or more solid supports with a population of attached first primers, nucleotides, and a cofactor such as a divalent cation. In some embodiments, the pre-seeding reaction mixture can further include a second primer and optionally a diffusion-limiting agent. In some embodiments, the population of template nucleic acid molecules comprise template nucleic acid molecules joined to at least one adaptor sequence which can hybridize to the first or second primers. In some embodiments, the reaction mixture can form an emulsion, as in emulsion RPA or emulsion PCR. In pre-seeding reactions carried out by RPA reactions, the pre-seeding reaction mixture can include a recombinase and optionally a recombinase accessory protein. The various components of the reaction mixture are discussed in further detail herein.

In a particular embodiment of seeding, the hydrophilic particles and polynucleotides are subjected to polymerase chain reaction (PCR) amplification or recombinase polymerase amplification (RPA). In an example, the particles 9704 include a capture primer complementary to a portion of the template polynucleotide 9702. The template polynucleotide can hybridize to the capture primer. The capture primer can be extended to form beads 9706 that include a target polynucleotide attached thereto. Other beads may remain unattached to a target nucleic acid and other template polynucleotide can be free floating in solution.

In an example, the bead support 9706 including a target polynucleotide can be attached to a magnetic bead 9710 to form a bead assembly 9712. In particular, the magnetic bead 9710 is attached to the bead support 9706 by a double stranded polynucleotide linkage. In an example, a further probe including a linker moiety can hybridize to a portion of the target polynucleotide on the bead support 9706. The linker moiety can be attached to a complementary linker moiety on the magnetic bead 9710. In another example, the template polynucleotide used to form the target nucleic acid attached to beads 9706 can include a linker moiety that attaches to the magnetic bead 9710. In another example, template polynucleotide complementary to target polynucleotide attached to the bead support 9706 can be generated from a primer that is modified with a linker that attaches to the magnetic bead 9710.

The linker moiety attached to the polynucleotide and the linker moiety attached to the magnetic bead can be complementary to and attach to each other. In an example, the linker moieties have affinity and can include: an avidin moiety and a biotin moiety; an antigenic epitope and an antibody or immunologically reactive fragment thereof; an antibody and a hapten; a digoxigen moiety and an anti-digoxigen antibody; a fluorescein moiety and an anti-fluorescein antibody; an operator and a repressor; a nuclease and a nucleotide; a lectin and a polysaccharide; a steroid and a steroid-binding protein; an active compound and an active compound receptor; a hormone and a hormone receptor; an enzyme and a substrate; an immunoglobulin and protein A; or an oligonucleotide or polynucleotide and its corresponding complement. In a particular example, the linker moiety attached to the polynucleotide includes biotin and the linker moiety attached to the magnetic bead includes streptavidin.

The bead assemblies 9712 can be applied over a substrate 9716 of a sequencing device that includes wells 9718. In an example, a magnetic field can be applied to the substrate 9716 to draw the magnetic beads 9710 of the bead assembly 9712 towards the wells 9718. The bead support 9706 enters the well 9718. For example, a magnet can be moved in parallel to a surface of the substrate 9716 resulting in the deposition of the bead support 9706 in the wells 9718.

The bead assembly 9712 can be denatured to remove the magnetic bead 9710 leaving the bead support 9706 in the well 9718. For example, hybridized double-stranded DNA of the bead assembly 9712 can be denatured using thermal cycling or ionic solutions to release the magnetic bead 9710 and template polynucleotides having a linker moiety attached to the magnetic bead 9710. For example, the double-stranded DNA can be treated with low ion-content aqueous solutions, such as deionized water, to denature and separate the strands. In an example, a foam wash can be used to remove the magnetic beads.

Optionally, the target polynucleotides 9706 can be amplified, referred to herein as templating, while in the well 9718, to provide a bead support 9714 with multiple copies of the target polynucleotides. In particular, the bead 9714 has a monoclonal population of target polynucleotides. Such an amplification reactions can be performed using polymerase chain reaction (PCR) amplification, recombination polymerase amplification (RPA) or a combination thereof. Alternatively, amplification can be performed prior to depositing the bead support 9714 in the well.

In a particular embodiment, an enzyme such as a polymerase is present, bound to, or is in close proximity to the particles or beads. In an example, a polymerase is present in solution or in the well to facilitate duplication of the polynucleotide. A variety of nucleic acid polymerase may be used in the methods described herein. In an example embodiment, the polymerase can include an enzyme, fragment or subunit thereof, which can catalyze duplication of the polynucleotide. In another embodiment, the polymerase can be a naturally occurring polymerase, recombinant polymerase, mutant polymerase, variant polymerase, fusion or otherwise engineered polymerase, chemically modified polymerase, synthetic molecules, or analog, derivative or fragment thereof. Example enzymes, solutions, compositions, and amplification methods can be found in WO2019/094,524, titled "METHODS AND COMPOSITIONS FOR MANIPULATING NUCLEIC ACIDS", which is incorporated herein by reference in its entirety.

While the polynucleotides of bead support 9714 are illustrated as being on a surface, the polynucleotides can extend within the bead support 9714. Hydrogel and hydrophilic particles having a low concentration of polymer relative to water can include polynucleotide segments on the interior of and throughout the bead support 9714 or polynucleotides can reside in pores and other openings. In particular, the bead support 9714 can permit diffusion of enzymes, nucleotides, primers and reaction products used to monitor the reaction. A high number of polynucleotides per particle produces a better signal.

In an example embodiment, the bead support 9714 can be utilized in a sequencing device. For example, a sequencing device 9716 can include an array of wells 9718.

In an example, a sequencing primer can be added to the wells 9718 or the bead support 9714 can be pre-exposed to the primer prior to placement in the well 9718. In particular, the bead support 9714 can include bound sequencing primer. The sequencing primer and polynucleotide form a nucleic acid duplex including the polynucleotide (e.g., a template nucleic acid) hybridized to the sequencing primer. The nucleic acid duplex is an at least partially double-stranded polynucleotide. Enzymes and nucleotides can be provided to the well 9718 to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system 9716 and can migrate to the well 9718. Excitation energy can be also provided to the well 9718. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well 9718 can change. Such a change in pH can be detected by ion sensitive field effect transistors (ISFET). As such, a change in pH can be used to generate a signal indicating the order of nucleotides complementary to the polynucleotide of the particle 9710.

In particular, a sequencing system can include a well, or a plurality of wells, disposed over a sensor pad of an ionic sensor, such as a field effect transistor (FET). In embodiments, a system includes one or more polymeric particles loaded into a well which is disposed over a sensor pad of an ionic sensor (e.g., FET), or one or more polymeric particles loaded into a plurality of wells which are disposed over sensor pads of ionic sensors (e.g., FET). In embodiments, an FET can be a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, can be used for measuring ion concentrations in solution; when the ion concentration (such as H+) changes, the current through the transistor changes accordingly.

In embodiments, the FET may be a FET array. As used herein, an "array" is a planar arrangement of elements such as sensors or wells. The array may be one or two dimensional. A one-dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In embodiments, one or more microfluidic structures can be fabricated above the FET sensor array to provide for containment or confinement of a biological or chemical reaction. For example, in one implementation, the microfluidic structure(s) can be configured as one or more wells (or wells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FET sensors and reaction wells.

Returning to FIG. 97, in another example, a well 9718 of the array of wells can be operatively connected to measuring devices. For example, for fluorescent emission methods, a well 9718 can be operatively coupled to a light detection device. In the case of ionic detection, the lower surface of the well 9718 may be disposed over a sensor pad of an ionic sensor, such as a field effect transistor.

One example system involving sequencing via detection of ionic byproducts of nucleotide incorporation is the Ion Torrent PGM™, Proton™ or S5™ sequencer (Thermo Fisher Scientific), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™, Proton™, or S5™ sequencer detects the nucleotide incorporations by detecting the hydrogen ion byproducts of the nucleotide incorporations. The Ion Torrent PGM™, Proton™ or S5™ sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously.

In an embodiment, the systems monitors the location and type of consumable items, determines a next step in the procedure, and displays a notice indicating the next location and type of consumable to place in or remove from the instrument. Monitoring is performed by images from a camera or by radio frequency identification. Consumable items include sample preparation supplies, reagent strips or bottles, or sequencing chips and adaptors. In particular, the system can track setup and cleanup of the instrument to ensure proper cleaning and setup for subsequent sequencing runs.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, R, Pascal, Basic, Fortran, Cobol, Perl, Java, and Ada.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In a first embodiment, a method for user guided initiating of an instrument includes receiving a run plan via a user interface of the instrument; indicating on the user interface, based on the run plan, a consumable to be provided to the instrument; detecting the presence of the consumable using a vision system; and indicating the presence of the consumable via the user interface.

In an example of the first embodiment, the method further includes repeating: indicating a consumable to be provided; detecting the presence of the consumable; and indicating the presence of the consumable.

In another example of the first embodiment and the above examples, the instrument is a nucleic acid sequencing instrument.

In a further example of the first embodiment and the above examples, the method further includes: determining with the vision system the presence of a used consumable and indicating to a user via the user interface the location and presence of the used consumable. For example, determining the presence of the used consumable includes determining with the vision system a number of unused reagent containers of a set of reagent containers and determining whether the number of unused reagent containers is sufficient to perform the run plan. In an example, determining a number of unused reagent containers includes determining a number of used reagent containers by detecting foil piercings of the used reagent containers with the vision system. In another example, the method further includes indicating through the user interface the set of reagent containers is to be replaced when the number of unused reagent containers is insufficient to implement the run plan. For example, the method further includes detecting a position of a latch associated with the set of reagent containers with the vision system. In an example, detecting the position includes detecting a set of indicators with the vision system. In another example, the method further includes detecting a locked state of the latch with the vision system. For example, detecting the locked state includes detecting a change in indicators associated with the latch in a closed position.

In an additional example of the first embodiment and the above examples, the method further includes reading a code of the consumable with the vision system and indicating the presence of the consumable via the user interface when the code is correct.

In another example of the first embodiment and the above examples, the method further includes determining with an RFID system the presence of a consumable and indicating via the user interface the presence of the consumable.

In a further example of the first embodiment and the above examples, the method further includes detecting with the vision system a lid disposed on the consumable and indicating via the user interface the presence of the lid.

In a second embodiment, a method for initiating an instrument includes determining with a vision module in communication with a camera of the instrument a number of unused reagent containers of a set of reagent containers; receiving at an interface of the instrument a run plan; and determining whether the number of unused reagent containers is sufficient to perform the run plan.

In an example of the second embodiment, determining the number of unused reagent containers includes detecting a number of used reagent containers.

In a third embodiment, a method for preparing an instrument vision system includes detecting a location of an instrument feature within a video stream of an instrument deck taken by a camera; determining a location within frames of the video stream at which the instrument feature is to appear; illustrating the location of the instrument feature and the location at which the instrument feature is to appear in the video stream as displayed on a user interface; and aligning the location of the instrument feature and the location at which the instrument feature is to appear by adjusting the camera.

In an example of the third embodiment, the locations are indicated by circles and aligning includes causing the circles to overlap.

In a fourth embodiment, an instrument includes a management system to receive a run plan; a vision system include a vision module and a set of cameras, the vision module in communication with the management system; and a user interface in communication with the management module; wherein the vision system is to detect the presence or absence of a set of consumables associated with the run plan; wherein the management system is to display a series of interfaces on the user interface indicating the presence or absence of consumables of the set of consumables.

In an example of the fourth embodiment, the instrument further includes an RFID module in communication with the management module and an RFID antenna to detect consumables of a second set of consumables.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method for user guided initiating of an instrument, the method comprising:
    receiving a run plan via a user interface of the instrument, the run plan identifying a test to be performed by the instrument and parameters associated with the test, the test to utilize a set of consumables;
    indicating on the user interface, based on the run plan, the set of consumables to be used by the instrument when implementing the run plan;
    detecting the presence of a consumable of the set of consumables using a vision system including a camera;
    determining with the vision system that the consumable is a used consumable, the used consumable including a set of reagent containers;
    determining with the vision system a number of unused reagent containers of the set of reagent containers, wherein determining a number of unused reagent containers includes determining a number of used reagent containers by detecting foil piercings of the used reagent containers with the vision system based on a comparison of pixel values of an image acquired by the vision system with the camera to expected values;
    determining whether the number of unused reagent containers is sufficient to perform the run plan;
    indicating the presence of the used consumable via the user interface; and
    detecting a position of a latch with the vision system, the latch to hold an associated reagent container of the set of reagent containers in place when in a locked position, wherein detecting the locked position includes detecting a set of indicators on the outer surface of the associated latch with the vision system.

2. The method of claim 1, further comprising:
    indicating another consumable to be provided;
    detecting the presence of the other consumable; and
    indicating the presence of the other consumable.

3. The method of claim 1, wherein the instrument is a nucleic acid sequencing instrument.

4. The method of claim 1, further comprising indicating through the user interface the used consumable is to be replaced when the number of unused reagent containers is insufficient to implement the run plan.

5. The method of claim 1, wherein detecting the locked position includes detecting a change in how many of the visual indicators of the latch are detected.

6. The method of claim 1, further comprising reading a code of a second consumable of the set of consumables with the vision system and indicating the presence of the second consumable via the user interface when the code is correct.

7. The method of claim 1, further comprising determining with an RFID system the presence of a second consumable and indicating via the user interface the presence of the second consumable.

8. The method of claim 1, further comprising detecting with the vision system a lid disposed on the consumable and indicating via the user interface the presence of the lid.

9. The method of claim 1, wherein the set of consumables includes a reagent strip, a tray of pipette tips, and a microwell array.

10. The method of claim 9, wherein the instrument includes an instrument deck on to which consumables of the set of consumables are to be located.

11. The method of claim 10, wherein the instrument includes a reagent storage cabinet to store another consumable of the set of consumables.

12. The method of claim 10, wherein the instrument includes a three-axis pipetting robot having access to the instrument deck.

13. The method of claim 10, wherein the camera acquires images of an area of the instrument deck.

* * * * *